(12) United States Patent
Hayes et al.

(10) Patent No.: US 9,585,387 B1
(45) Date of Patent: Mar. 7, 2017

(54) PEHAM DENDRIMERS FOR USE IN AGRICULTURE

(71) Applicants: Starpharma Pty Ltd, Preston (AU); Dendritic Nanotechnologies, Inc., Midland, MI (US)

(72) Inventors: Ryan T. Hayes, Berrien Springs, MI (US); David James Owen, Abbotsford (AU); Abhay Singh Chauhan, Wauwatosa, WI (US); Veera Reddy Pulgam, Ann Arbor, MI (US); Harsh Vardhan, Glen Waverley (AU)

(73) Assignee: STARPHARMA PTY LTD, Abbotsford (AU)

( * ) Notice: Subject to any disclaimer, the term of this patent is extended or adjusted under 35 U.S.C. 154(b) by 0 days.

(21) Appl. No.: 14/623,268

(22) Filed: Feb. 16, 2015

Related U.S. Application Data

(63) Continuation-in-part of application No. 13/101,098, filed on May 4, 2011, now abandoned, which is a continuation-in-part of application No. PCT/US2010/054164, filed on Oct. 26, 2010.

(60) Provisional application No. 61/256,951, filed on Oct. 31, 2009, provisional application No. 61/254,985, filed on Oct. 26, 2009.

(51) Int. Cl.
*A01N 57/20* (2006.01)
*A01N 33/18* (2006.01)
*A01N 43/40* (2006.01)
*A01P 7/04* (2006.01)
*A01P 13/00* (2006.01)
*A01N 25/32* (2006.01)
*A01N 25/00* (2006.01)
*A01N 43/50* (2006.01)

(52) U.S. Cl.
CPC ............ *A01N 25/32* (2013.01); *A01N 25/00* (2013.01); *A01N 33/18* (2013.01); *A01N 43/50* (2013.01); *A01N 57/20* (2013.01)

(58) Field of Classification Search
CPC ...... A01N 33/18; A01N 43/54; A01N 43/653; A01N 47/02; A01N 47/20; A01N 59/20; A01N 25/22; A01N 25/24; A01N 25/30; C08L 101/005
See application file for complete search history.

(56) References Cited

U.S. PATENT DOCUMENTS

| | | | |
|---|---|---|---|
| 5,834,020 A | 11/1998 | Margerum et al. | |
| 6,638,994 B2 | 10/2003 | Crooks et al. | |
| 6,939,831 B1 | 9/2005 | Caminade et al. | |
| 7,981,444 B2 | 7/2011 | Tomalia et al. | |
| 7,985,424 B2 * | 7/2011 | Tomalia et al. | 424/486 |
| 2006/0039891 A1 | 2/2006 | Malik et al. | |
| 2007/0244296 A1 | 10/2007 | Tomalia et al. | |
| 2007/0298006 A1 * | 12/2007 | Tomalia et al. | 424/78.03 |
| 2009/0137667 A1 | 5/2009 | Kabanov et al. | |

OTHER PUBLICATIONS

Hartzler (Which glyphosate product is the best? Weed Science Iowa State University, http://www.weeds.iastate.edu/mgmt/2001/glyphosateformulations03.htm (1996-2003).*
Baker, Edward A., et al., "Physicochemical Properties of Agrochemicals: Their Effects on Foliar Penetration" Pestic. Sci. 34, 167-182 (1992).
Stevens, Peter, J. G., et al. "Adhesion of Spray Droplets to Foliage: The Role of Dynamic Surface Tension and Advantages of Organosilicone Surfactants": Pestic. Sci. 38, 237-245 (1993).
Reddy, N. P., et al., Pest Manag. Sci. 64, 909-915 (2008).
Large, E. C. et al., Annals of Applied Biol., 33(1), 54-63 (1945).
Hislop, E. C. et al., Ann. Appl. Biol. 66, 89-101 (1970).
Baker, Edward A., Pestic. Sci. 29, 187-196 (1990).
Reddy, Krishna N., et al., Pestic. Sci. 48, 179-187 (1996).
Tufteland, Megan L. et al., Pest Manag. Sci. 65, 624-628 (2009).
Scrano, Laura et al., Pestic. Sci. 55, 995-961 (1999).
Sur, Nivedita et al., Pest Manag. Sci. 56, 289-292 (2000).
Chattopadhyaya S. et al., Pestic. Sci. 31, 163-173 (1991).
Walia, S. et al., Pestic. Sci. 25, 1-9 (1989).
Saha, Tapas et al., Pest Manag. Sci. 58, 179-182 (2001).
Kwon, Jeong-Wook, et al., Pest Manag. Sci. 60, 939-943 (2004).
Si, You-Bin, et al., Pest Manag. Sci. 60, 286-290 (2003).
Marsella, Adam, et al., Pest Manag. Sci. 56, 789-794 (2000).
Schick, Bernhard et al., Pestic. Sci. 55, 1116-1122 (1999).
Li, Zhu-Zhu et al., Pest Manag. Sci. 63, 241-246 (2007).

(Continued)

*Primary Examiner* — Anna Falkowitz

(74) *Attorney, Agent, or Firm* — Glenn Foulds; Carol L. Francis; Bozicevic, Field & Francis LLP

(57) ABSTRACT

PEHAM dendrimers of the formula:

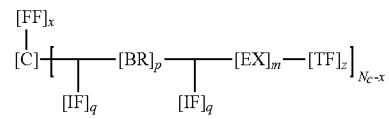

Specific PEHAM dendrimers are used in a formulation with an active agent for agricultural purposes. In particular, the PEHAM dendrimers may be used for increasing the efficacy of the active agent in various ways, such as by improving solubility of the active agent in the formulation, by improving adhesion and penetration of the active agent to plant surfaces, or by improving the water-fastness of the active agent to the plant or seed. The PEHAM dendrimers may also increase the efficacy of the active agent by increasing soil penetration of the active agent to reach the plant roots or under soil parts, by reducing soil adhesion of the active agent to reach the plant roots or under soil parts, or by reducing enzymatic degradation of the active agent by the plant or seed or microorganisms in the soil.

5 Claims, 11 Drawing Sheets

(56) References Cited

OTHER PUBLICATIONS

Hussain, Manzoor et al, Pestic. Sci. 28, 345-355 (1990).
Kocher, Helmut et al., Pestic. Sci. 37, 155-158 (1993).
Schwack, Wolfgang et al., Pestic. Sci. 40, 279-284 (1994).
Eds. J.M.J. Frechet, D. A. Tomalia, Dendrimers and other Dendritic Polymers, pub. John Wiley and Sons, (2001).
Michael Malkoch et al., J.Am.Chem.Soc. 127, 14942-14949 (2005).

* cited by examiner

PEHAM DENDRIMERS FOR USE IN AGRICULTURE

CROSS REFERENCE

This present application is a continuation-in-part of and claims priority to U.S. patent application Ser. No. 13/101,098, filed May 4, 2011, which claims priority to PCT/US2010/054164, filed Oct. 26, 2010, which claims priority to U.S. Provisional Application 61/256,951, filed Oct. 31, 2009 and U.S. Provisional Application 61/254,985, filed Oct. 26, 2009, the specification(s) of which is/are incorporated herein in their entirety by reference.

FIELD OF THE INVENTION

This invention relates broadly to the use of PEHAM dendrimers in agricultural applications, but more specifically for the protection and treatment of plants and seeds with specific PEHAM dendrimers.

BACKGROUND OF THE INVENTION

Dendrimers are highly branched, often spherical molecules in which branches may terminate at charged amino groups that radiate from a central core molecule. Amine-terminated dendrimers have a high density of positively charged amine groups on the surface, such as with PAMAM dendrimers. Due to controlled chemical synthesis, dendrimers have a very precise size and defined shape.

PEH wherein:
(C) means a core selected from the group consisting of PETGE, PETriGE and TMPTGE;
(FF) means a focal point functionality component of the core selected from the group consisting of Et, OH, SH, $NH_2$, $CO_2H$, carboxylate esters, straight- or branch chain $C_1$-$C_{18}$ alkyl, aryl, aryl heterocyclic moieties, $C_1$-$C_3$ alkoxy, triazole, $C_1$-$C_{18}$ alkyl esters, polyethyleneglycol and polyfluorinated moieties;
x is independently 0 or 1;
(BR) means a branch cell, which if p is greater than 1, then (BR) may be the same or a different moiety, selected from the group consisting of DBA, DEA, DEIDA, DETA, DIA, IDA, IDADS, PETriGE, TREN, TRIS, bis(2-methoxyethyl)amine, methylacrylate, N,N-di-Hexylamino, proparyl alcohol and trimethylamine
p is the total number of branch cells (BR) in the dendrimer and is an integer derived by the following equation $$p = \text{Total \# of } [BR] = \left(\frac{N_b^1}{N_b} + \frac{N_b^2}{N_b} + \frac{N_b^3}{N_b} + \ldots \frac{N_b^G}{N_b}\right)[N_c] = \left(\sum_{i=0}^{i=G-1} N_b^i\right)[N_c]$$

where: G is number of concentric branch cell shells (generation) surrounding the core which is 0, 1, 2 or 3;
i is final generation G;
$N_b$ is branch cell multiplicity; and
$N_c$ is core multiplicity and is an integer from 1 to 4;
with the proviso that when x is 1, $N_c$-x must be an integer from 1 to 3;
(IF) means interior functionality, which is OH;
q is independently 0 or an integer from 1 to 64;
(EX) means an extender, which, if m is greater than 1, then (EX) may be the same or a different moiety, selected from the group consisting of amino acids such as lysine, poly(amino acids) such as polylysine, oligoethyleneglycols, EDA, diethylenetetraamine and higher amine analogs, oligoalkylenamines protected as 5-membered imidazolidyl derivatives, fatty acids with di- or greater heterogeneous or homogenous functionality, unsaturated aliphatic and aromatic difunctional or polyfunctional moieties, EA, morpholine, dicarboxylic acids, EPC, IMAE, aryl dimercaptans, dimercaptoalkanes, triazoles, DMI, diazides, diacetylenes, pyrrolidone, pyrrolidone esters, aminoalkyl imidazolines, imidazolidines, poly(alkyleneimidazolidines), mercaptoalkylamines, hydroxyalkylamines or heterogeneous unsaturated aliphatic and aromatic difunctional or polyfunctional moieties;
m is independently 0 or an integer from 1 to 64;
when both q and m are greater then 1, (BR) and (EX) may occur alternately with the other moiety or sequentially with multiple groups of (BR) or (EX) occurring in succession;
(TF) means a terminal functionality, which, if z is greater than 1, then (TF) may be the same or a different moiety selected from the group consisting of amino, methylamino, ethylamino, hydroxyethylamino, benzylamino, mercaptoethylamino, dimethylamino, diethylamino, bis(hydroxymethyl)amino, N-alkylated amino derivatives, N-acylated amino derivatives, N-arylated amino derivatives, $CO_2$—N($C_1$-$C_6$ alkyl), hydroxyl, mercapto, carboxyl, carboxylate salts, carboxy $C_1$-$C_{18}$ alkyl, straight- or branch chain $C_2$-$C_{18}$ alkenyl, methalkyl, amido, halo, urea, oxiranyl, aziridinyl, oxazolinyl, imidazolinyl, pyrrolidone, benzyl, phenyl, sulfonato, phosphonate, isocyanate, isothiocyanato, piperazinyl, ethyl piperazinyl, acrylate, methacrylate, acrylamides, azide, epoxide, ethyl imines, straight- or branch chain $C_1$-$C_{18}$ alkyl, $C_1$-$C_3$ alkoxy, $C_1$-$C_{18}$ alkyl esters, cyclic ethers, fatty amines, thiorane, morpholinyl, protected DETA, polyethyleneglycol, polyfluorinated moieties, and dendrons;
z means the number of surface groups from 1 to the theoretical number possible for (C) and (BR) for a given generation G and is derived by the following equation $$z = N_c N_b^G;$$

where: G, $N_b$ and $N_c$ are defined as above; and
with the proviso that at least one of (EX) or (IF) is present;
associated with at least one agriculturally active entity; and
at least one agriculturally-acceptable diluent or carrier; and
wherein the efficacy or duration of activity of the agriculturally active entity is increased.

These specific PEHAM dendrimers of Formula (I) are used in a formulation with at least one agriculturally active entity for agricultural purposes, particularly for increasing the efficacy of the agriculturally active entity in various ways. Especially these formulations are useful by improving solubility of the agriculturally active entity in the formulation, by improving adhesion and penetration of the agriculturally active entity to plant surfaces, by improving the water-fastness of the agriculturally active entity to the plant or seed, by increasing soil penetration of the agriculturally active entity to reach the plant roots or under soil parts, or by reducing soil adhesion of the agriculturally active entity to reach the plant roots or under soil parts, or reducing enzymatic degradation of the agriculturally active entity by the plant or seed or microorganisms in the soil. These improvements in the formulation enable lower amounts of the agriculturally active entity to be applied or reduce the number of repeat applications of the formulation, which reduces the environmental impact of the formulation and agriculturally active entity.

DETAILED DESCRIPTION OF THE INVENTION

Glossary

Figure 1:
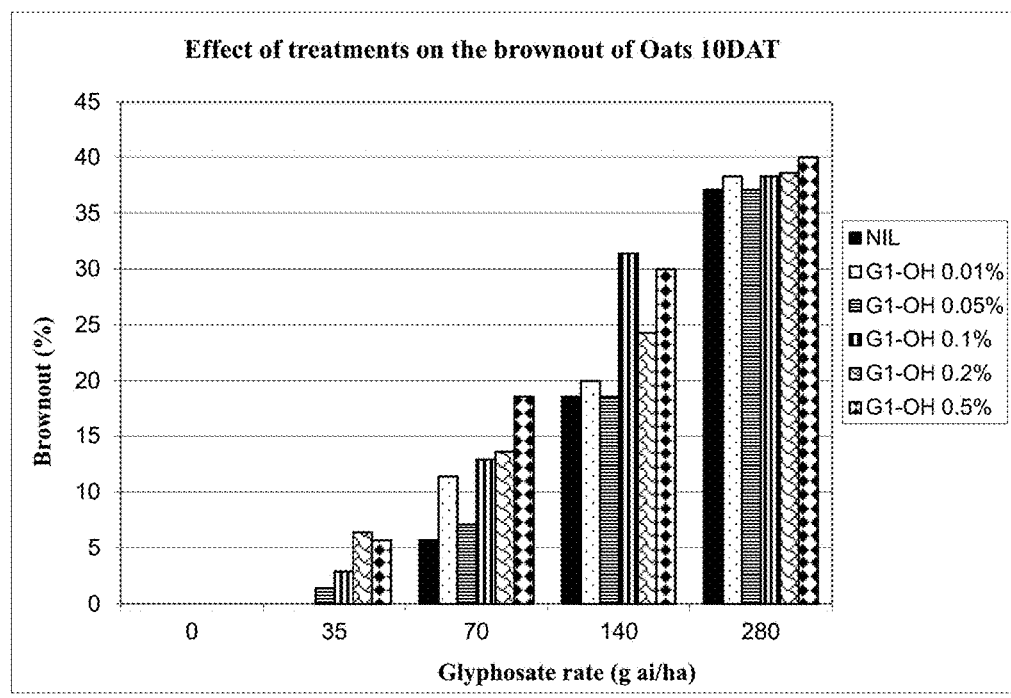
FIG. 1 shows a bar graph of the results of the brownout effects after treatment on *Avena sativa* 10DAT from Example 21.

The following terms as used in this application are to be defined as stated below and for these terms, the singular includes the plural.

ACC means 1-aminocyclopropanecarboxylate
ai means active ingredient
amu means atomic mass units
Bn means benzene
BR or (BR) means a branch cell
C or (C) means a core of a dendrimer or dendron
CDEA means 2-chloro-N,N-diethylacetamide
CEPC means 2-chloroethyl 3-chlorocarbanilate
4-CPA means 4-chlorophenoxyacetic acid
4-CPB means 4-(4-chlorophenoxy)butyric acid
m-CPBA means meta-chloroperoxy benzoic acid
CPMF means (EZ)-1-chloro-$N^2$-(3,4-dichlorophenyl)-$N^1$,$N^1$-dimethylformamidine
4-CPP means (RS)-2-(4-chlorophenoxy)propionic acid
CPPC means (RS)-2-chloro-1-methylethyl 3-chlorocarbanilate
2,4-D means (2,4-dichlorophenoxy)acetic acid
2,4-DB means 4-(2,4-dichlorophenoxy)butyric acid
DBA means dibenzylamine
DBCP means (RS)-1,2-dibromo-3-chloropropane
2,4-DEP means tris[2-(2,4-dichlorophenoxy)ethyl] phosphite
DCM means dichloromethane
pp'-DDT means 1,1,1-trichloro-2,2-bis(4-chlorophenyl)ethane
DEA means diethanolamine
DEIDA means diethyliminodiacetate
DETA means diethylenetriamine
DI means deionized water
DIA means diiminoamine
DMI means dimethylitaconate
DMPA means (RS)—(O-2,4-dichlorophenyl-O-methyl isopropylphosphoramidothioate)
DMSO means dimethylsulfoxide
DNOC means 4,6-dinitro-O-cresol
3,4-DP means (RS)-2-(3,4-dichlorophenoxy)propionic acid
DSMA means disodium methylarsonate
EA means ethanolamine
EBEP means ethyl bis(2-ethylhexyl)phosphinate
EC means emulsifiable concentrate
EDA means ethylenediamine
EPC means ethyl-N-piperazinecarboxylate
EPI means epichlorohydrin, usually further distilled prior to use
Et means ethyl
EtOH means ethanol
EX or (EX) means an extender
FF or (FF) means a focal point functionality component of a core
G means dendrimer generation, which is indicated by the number of concentric branch cell shells surrounding the core (usually counted sequentially from the core)
g means gram(s)
GC means gas chromatography
h means hour(s)
ha means hectare
HPLC means high pressure liquid chromatography
IAA means indole-3-acetic acid
IBA means indole-3-butyric acid
IDADS means iminodiacetic acid disodium salt
IDA means iminodiacetic acid
IF or (IF) means interior functionality
IMAE means 2-imidazolidyl-1-aminoethane
2iP means 6-(gamma,gamma-dimethylallylamino)purine or 6-(γ,γ-dimethylallylamino)purine
IR (or FTIR) means infrared spectrometry
L means liter(s)
MAA means methylarsonic acid
MAMA means ammonium hydrogen methylarsonate
MCPA means 2-(4-chloro-2-methylphenoxy)acetic acid
MCPB means 4-(4-chloro-2-methylphenoxy)butanoic acid
MeOH means methanol
mg means milligram(s)
min means minute(s)
mL means milliliter(s)
MSMA means sodium hydrogen methylarsonate
MWA means microwave assisted
N-SIS means nanoscale sterically induced stoichiometry
OD means oil dispersion.
PAMAM means poly(amidoamine), including linear and branched polymers or dendrimers with primary amine terminal groups
PEHAM means poly(etherhydroxylamine) dendrimer
PETAE means pentaerythritol tetraallyl ether
PETAZ means pentaerythritol tetraazide
PETGE means pentaerythritol tetraglycidyl ether
PETriGE means pentaerythritol triglycidyl ether
Percent or % means by weight unless stated otherwise such a weight/volume (w/v) etc
RT means ambient temperature or room temperature, about 20-25° C.
SC means suspension concentrate
SEC means size exclusion chromatography
SIS means sterically induced stoichiometry
2,4,5-T means (2,4,5-trichlorophenoxy)acetic acid
2,4,5-TB means 4-(2,4,5-trichlorophenoxy)butyric acid
2,3,6-TBA means 2,3,6-trichlorobenzoic acid
TCA means trichloroacetic acid
TCMTB means 2-thio-cyanato-methyl-thio-benzothiazole
TDE means 1,1-dichloro-2,2-bis(4-chlorophenyl)ethane
TEPP means tetraethyl pyrophosphate
TF means a terminal functionality
TLC means thin layer chromatography
TMPTGE means trimethylolpropane triglycidyl ether
TREN means tris(2-aminoethyl)amine
TRIS means tris(hydroxymethyl)aminomethane
UF means ultrafiltration separation
UV means ultraviolet wave length
UV-vis means ultraviolet and visible spectroscopy
WG means water dispersible granule Bioavailability of agrochemicals often needs a specific optimization to ensure best biological efficacy at the lowest possible application rate and the lowest impact on the environment. The application of the formulation must still have even distribution on the crop, easy dilution with water (the preferred solvent for farmers), optimal biological performance, easy and safe handling for the workers, and lowest possible environmental impact. This has proven to be difficult to achieve as the climate, crops, pests, and soil varies widely over the growing regions.

Formulations used in agriculture comprise: an active ingredient (where its properties greatly influence what form the formulation can be, such as solubility, lipophilicity, hydrolytic stability, photodegradation, etc.), other ingredients such as surfactants, carriers, excipients (the role of the present dendrimer is as a carrier for the active but it also does more than this function). The formulation type is dependent on the intended biological target and the method of application needed. Usual formulations types are: WG; SC; EC; and OD.

Figure 2:
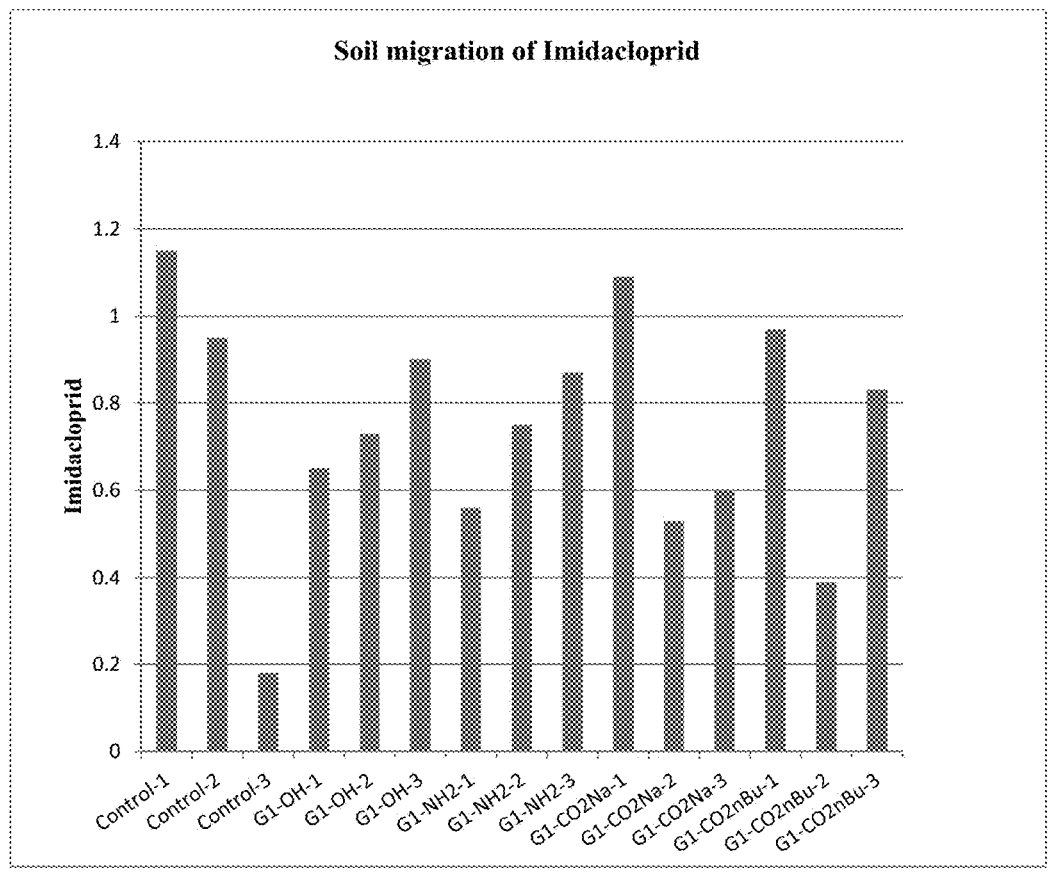
FIG. 2 shows a graph of the results obtained in Example 24.
Figure 3:
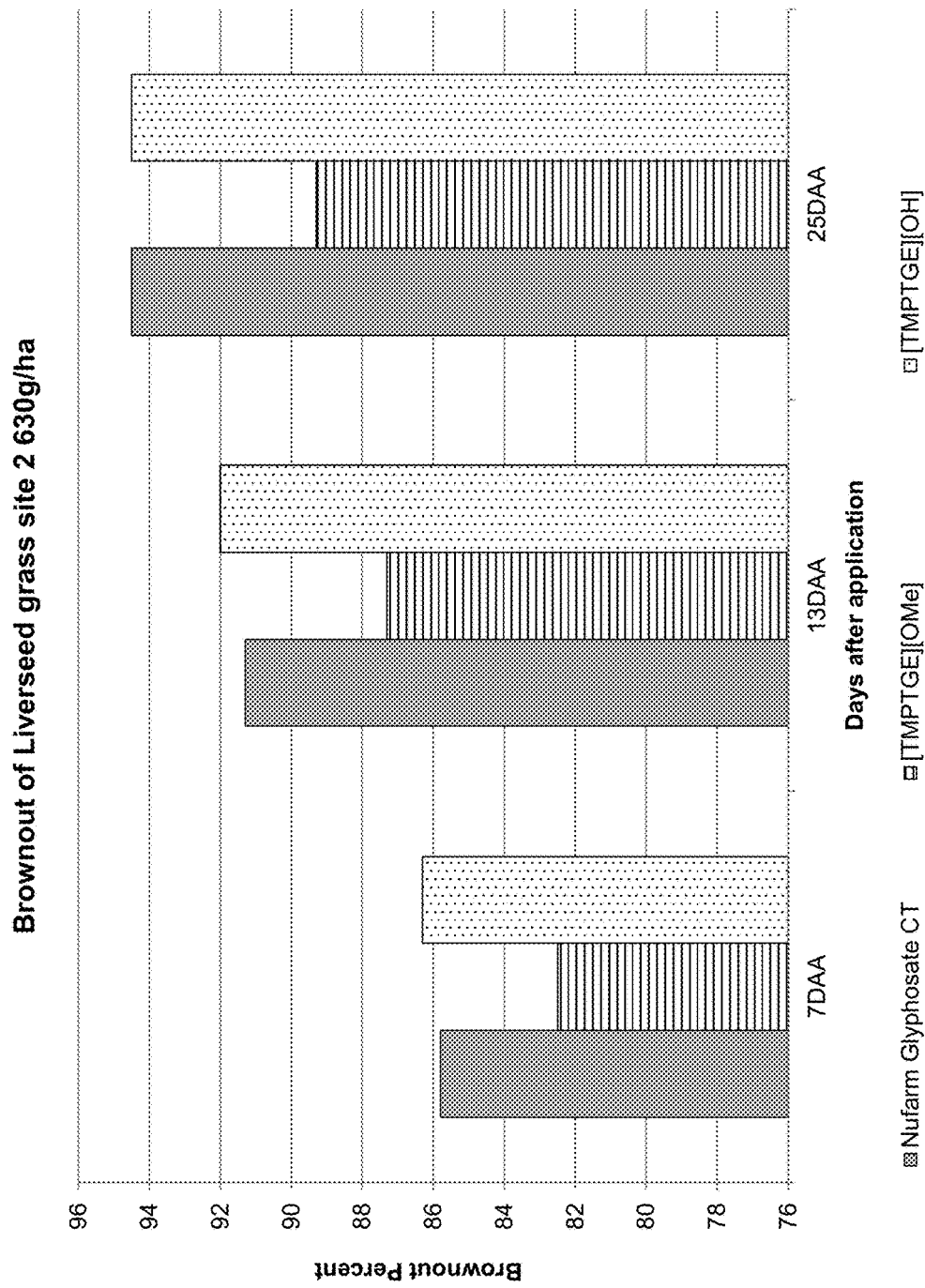
FIG. 3 shows a graph of the brownout effects on Liverseed grass.
Figure 4:
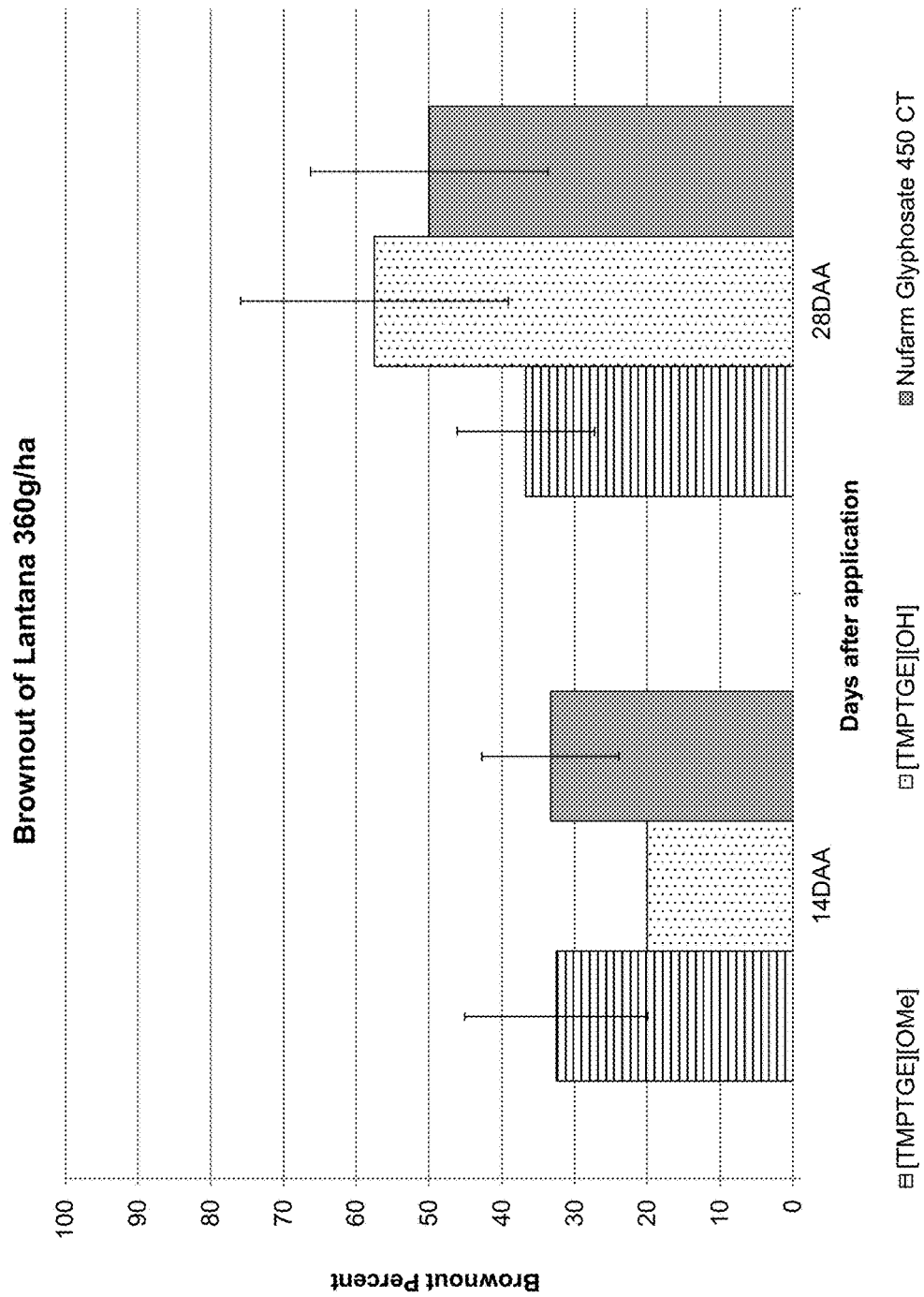
FIG. 4 shows a graph of the brownout effects on Lantana.
Figure 5:
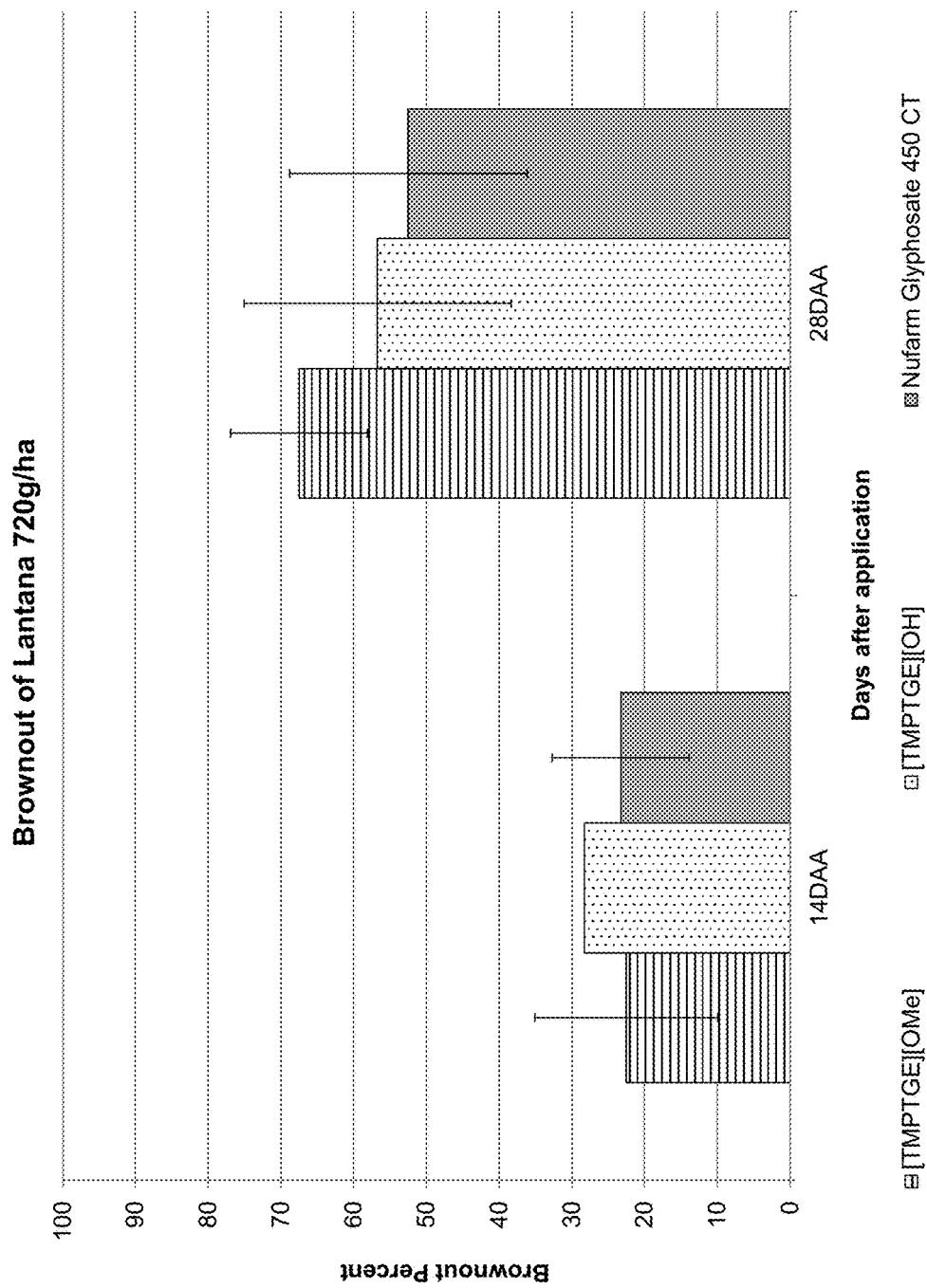
FIG. 5 shows a graph of the brownout effects on Lantana.
Figure 6:
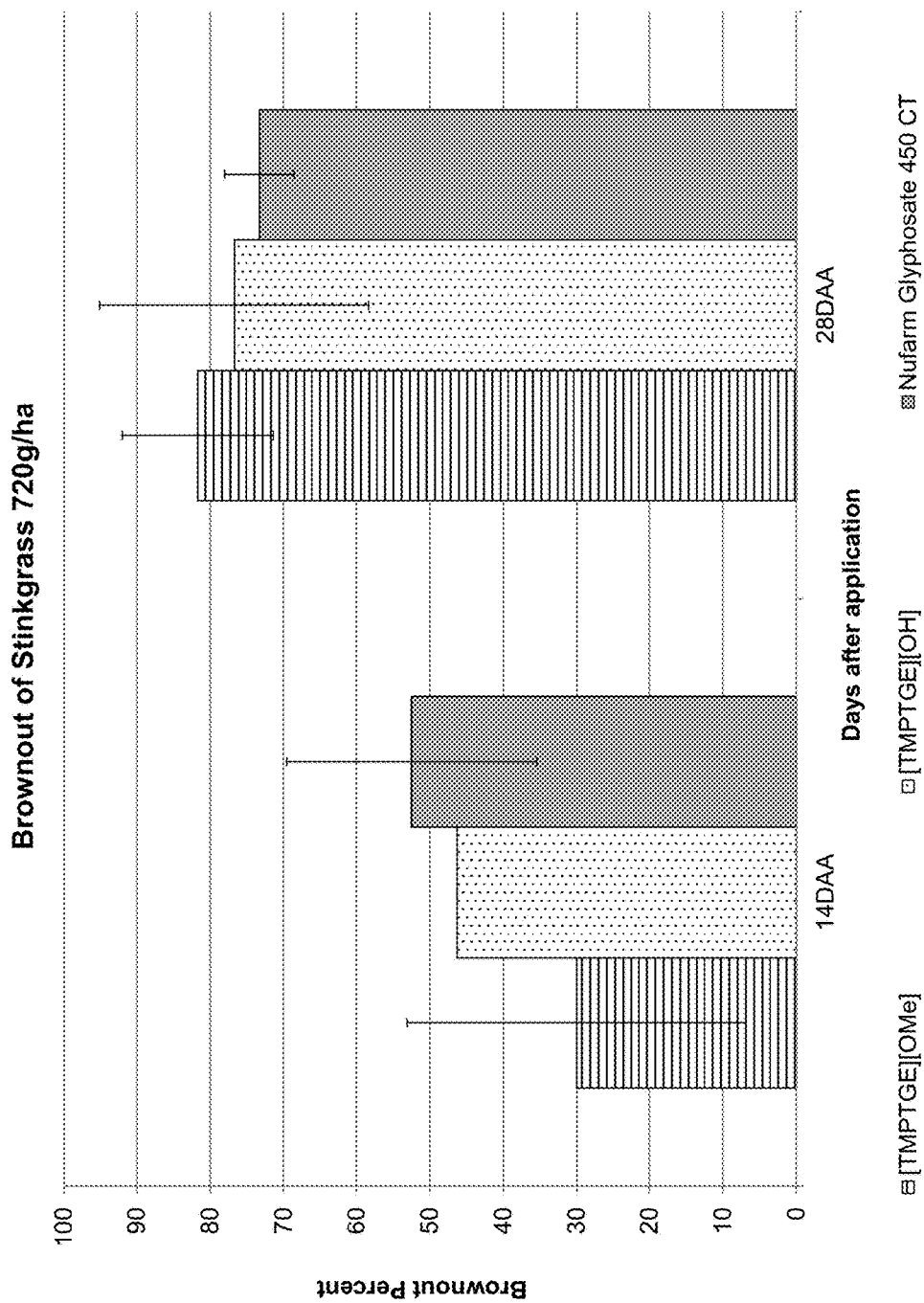
FIG. 6 shows a graph of the brownout effects on Stinkgrass.
Figure 7:
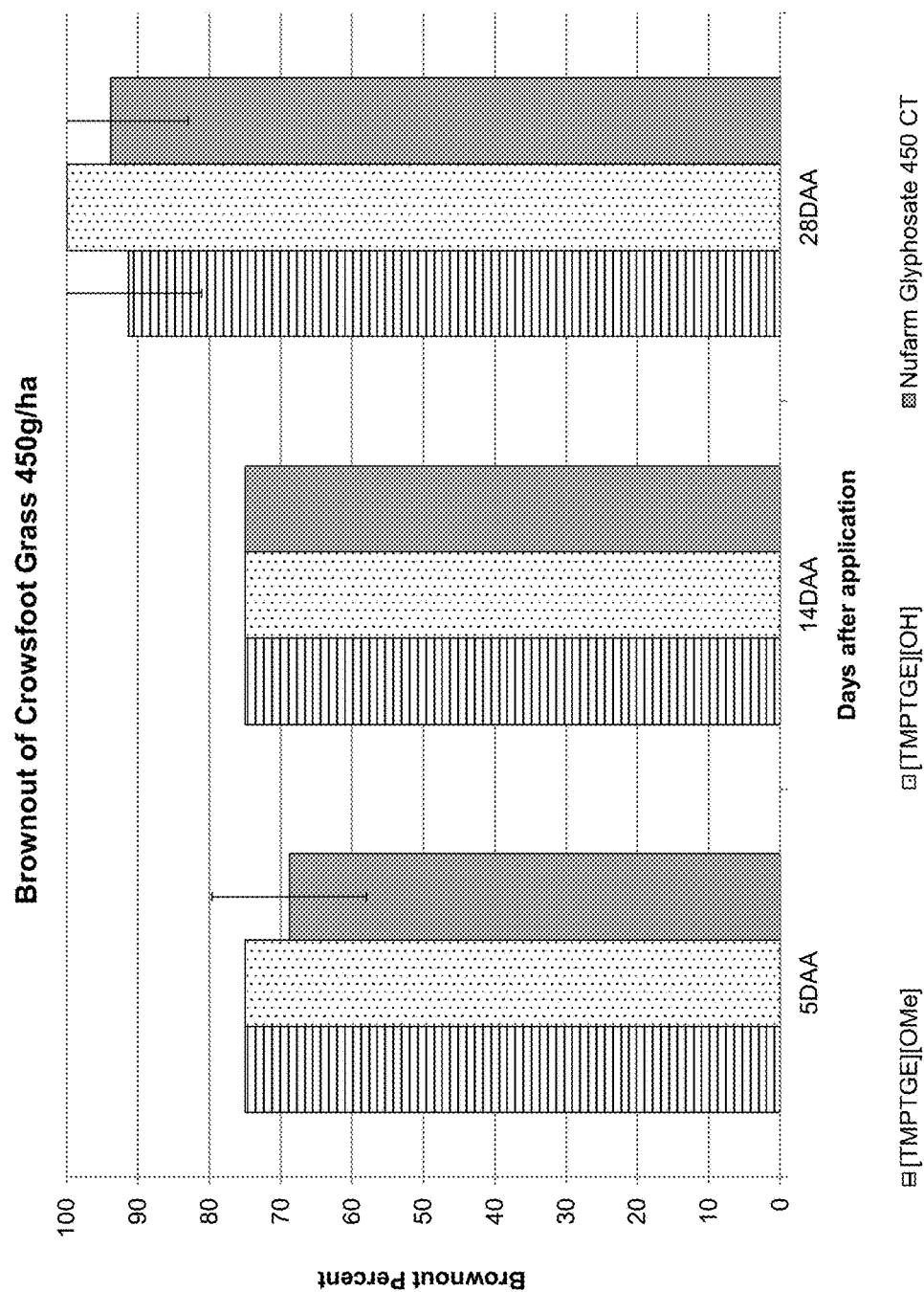
FIG. 7 shows a graph of the brownout effects on Crowsfoot Grass.
Figure 8:
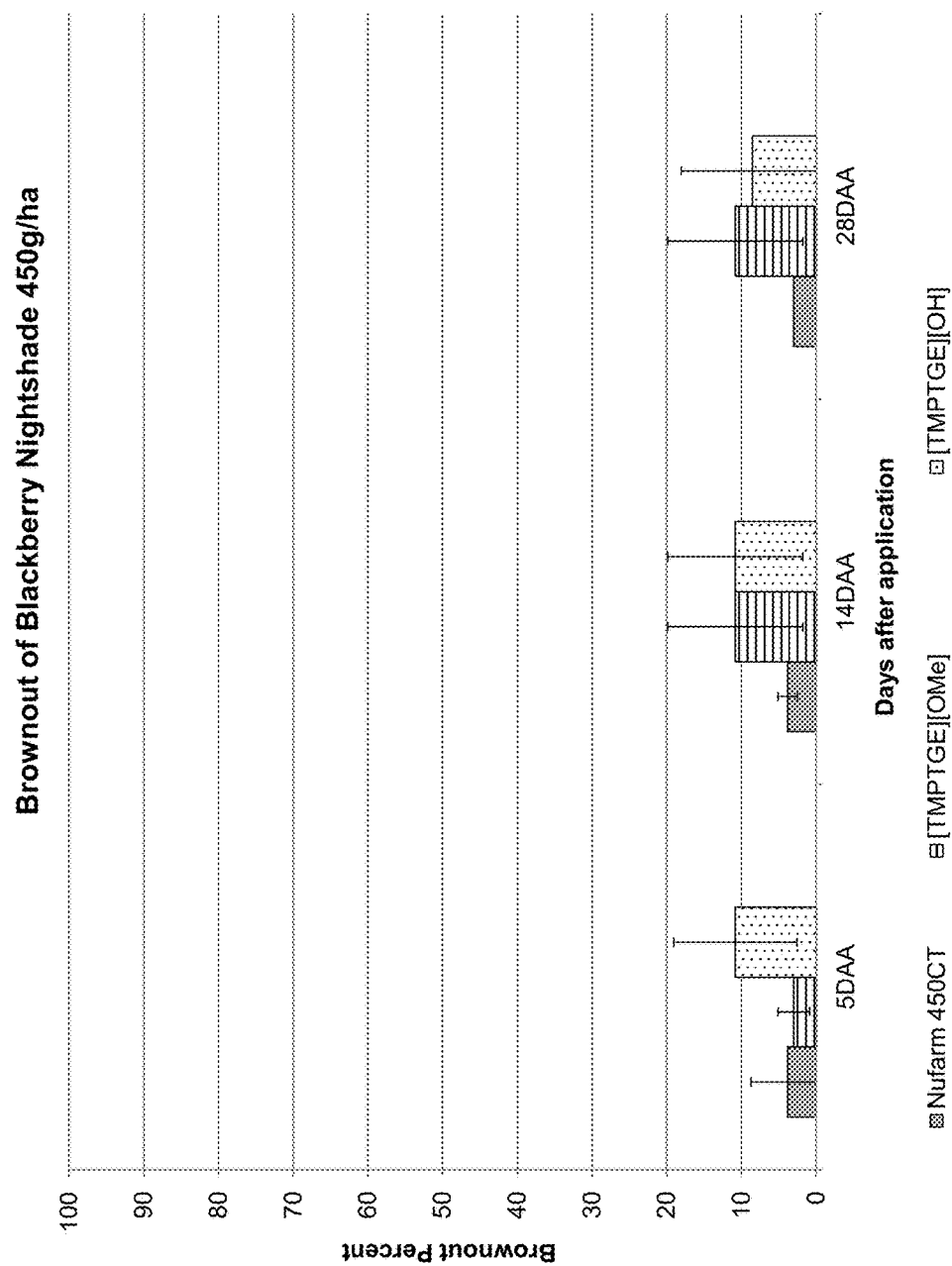
FIG. 8 shows a graph of the brownout effects on Blackberry Nightshade.
Figure 9:
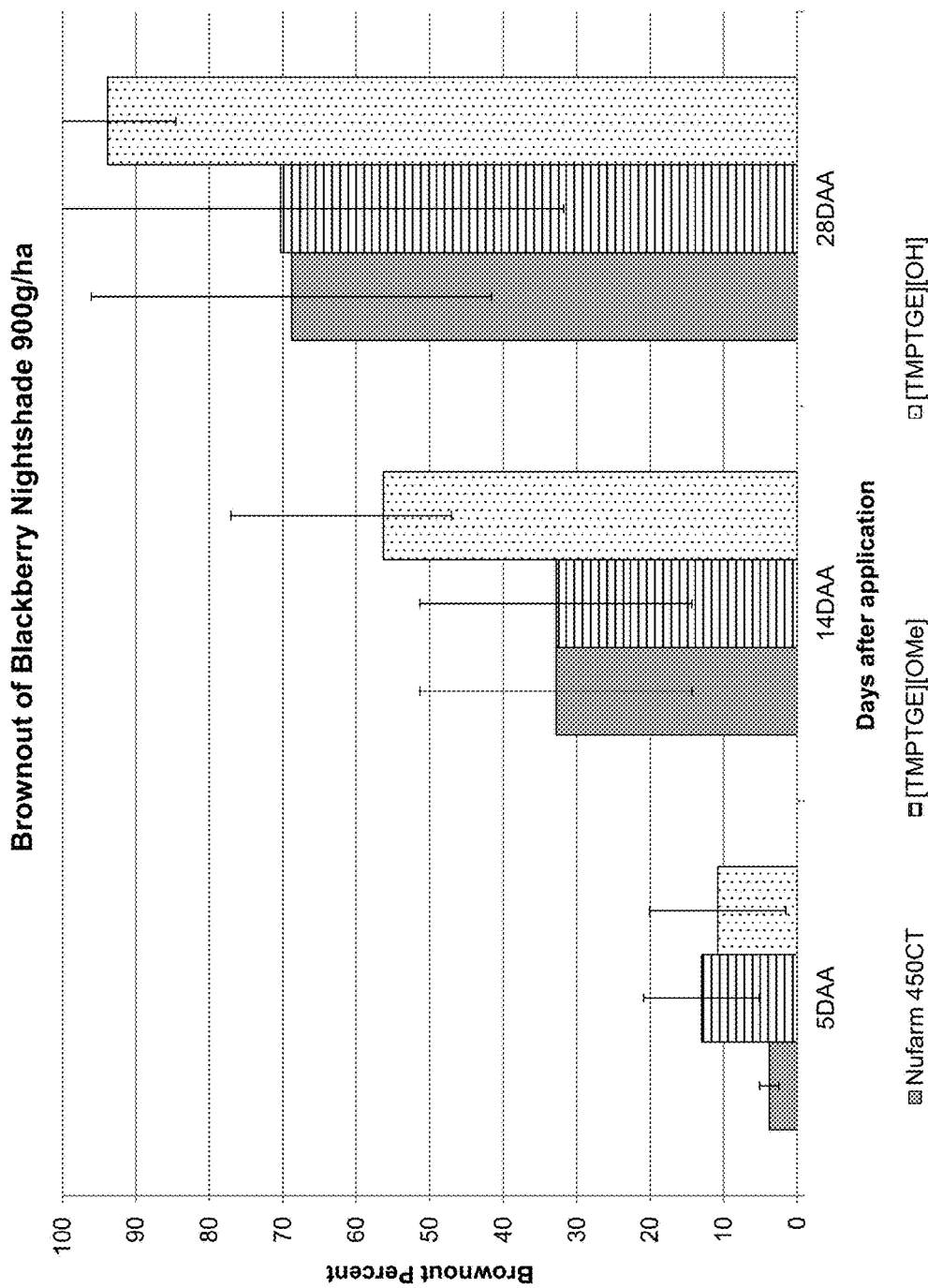
FIG. 9 shows a graph of the brownout effects on Blackberry Nightshade.
Figure 10:
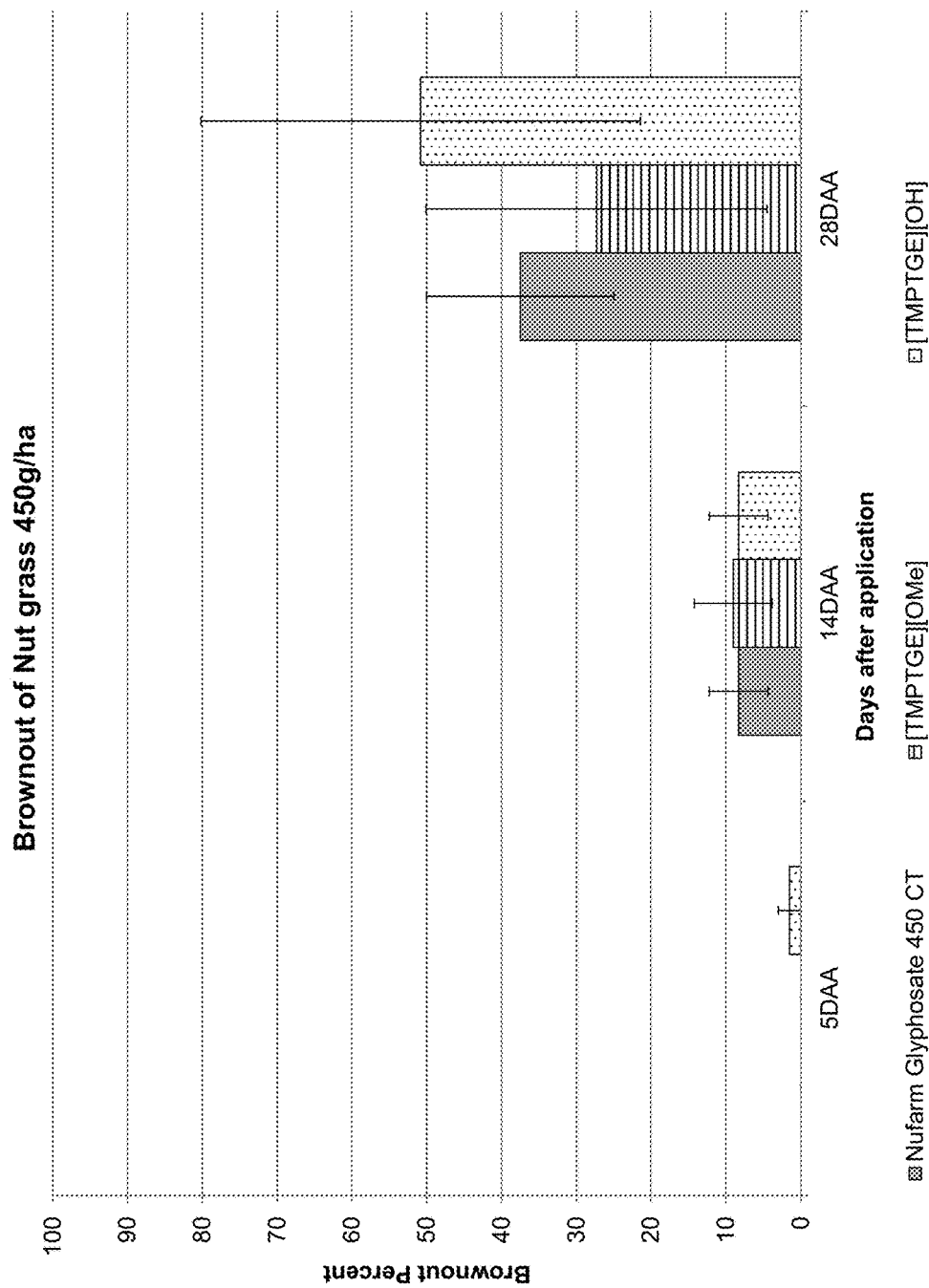
FIG. 10 shows a graph of the brownout effects on Nut grass.
Figure 11:
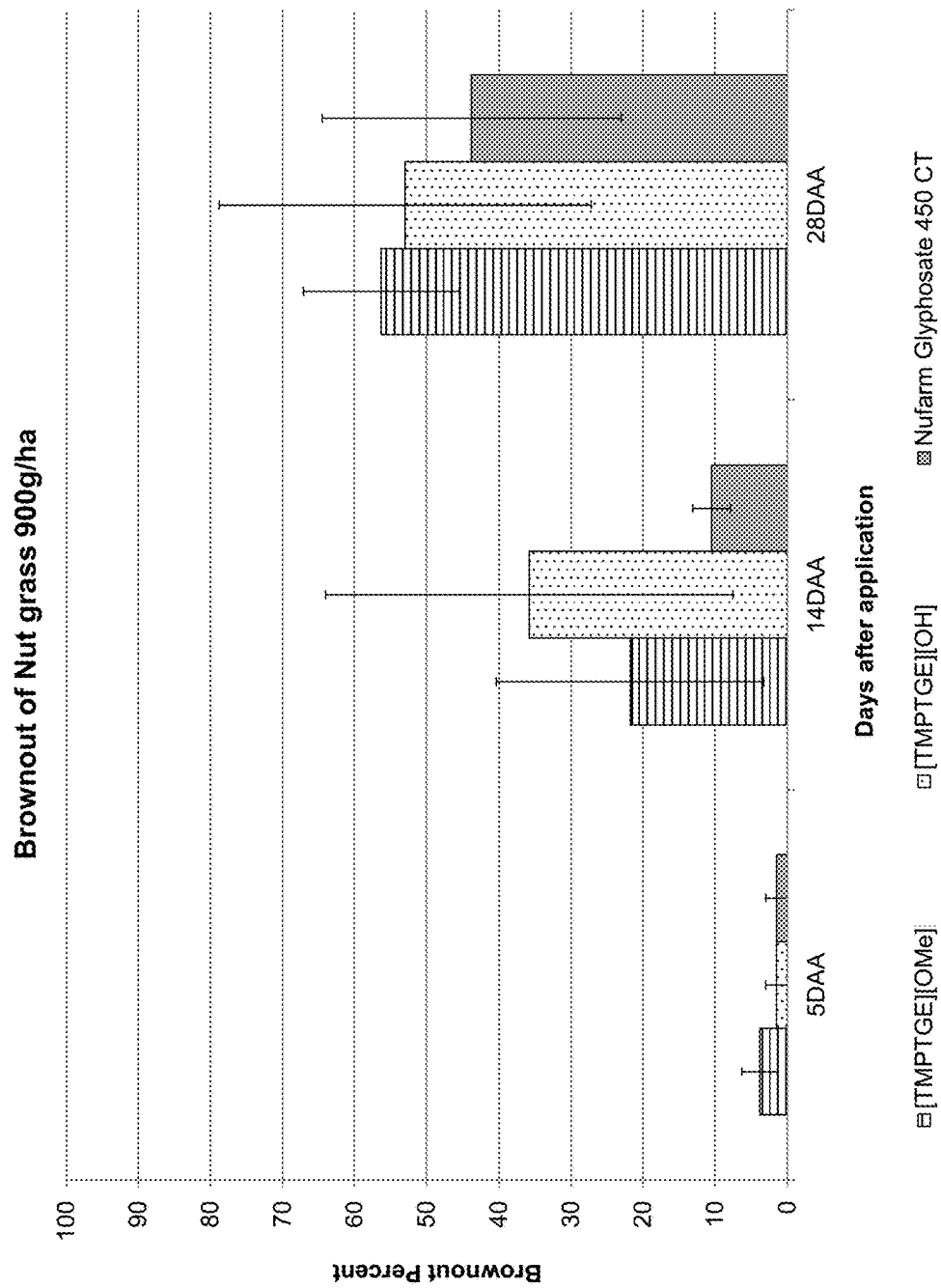
FIG. 11 shows a graph of the brownout effects on Nut grass.

Referring now to FIGS. 1-11, this invention describes PEHAM dendrimer formulations that are useful in agricultural applications such as regulating and controlling the development of plants, seeds, insects, microbes or animal pests.

Some aspects of this invention concern increasing the efficacy of the agriculturally active entity in various ways, such as by improving solubility of the agriculturally active entity in the formulation, by improving adhesion of the agriculturally active entity to plant surfaces, by improving the water-fastness (including rain-fastness to the active entity being washed off the plant by rain) of the agriculturally active entity to the plant or seed, by improving the penetration (absorption) of the agriculturally active entity into plant tissues, by increasing soil penetration of the agriculturally active entity to reach the plant roots or under soil parts, or by reducing soil adhesion of the agriculturally active entity to reach the plant roots or under soil parts, or reducing enzymatic degradation of the agriculturally active entity by the plant or seed or microorganisms in the soil.

Chemical Structures of PEHAM Dendritic Polymers

PEHAM dendritic polymer structures may be dendrimers, dendrons, dendrigrafts, tecto(dendritic) polymers or other dendritic architectures. There are numerous examples of such dendritic polymers in the literature, such as those described in *Dendrimers and other Dendritic Polymers*, eds. J. M. J. Fréchet, D. A. Tomalia, pub. John Wiley and Sons, (2001) and other such sources.

These PEHAM dendritic polymers can be any physical shape, such as for example spheres, rods, tubes, or any other shape possible. The interior structure may have an internal cleavable bond (such as a disulfide), void volume for encapsulation, or an internal functionality (IF) such as a hydroxide or other group to associate with an active ingredient. Additionally, the PEHAM dendritic polymer can be a dendron. This dendron can have any dendritic polymer constituents desired.

The dendritic polymers of this invention are PEHAM dendrimers including PEHAM dendrons. These PEHAM dendrimers have the structures as discussed above and further described below. These PEHAM dendrimers are a narrowed class (selection invention) of prior PEHAM dendrimers (cited above) with regard to the various (C), (FF), (IF), (BR), (EX) moieties that have been found to particularly useful in the present formulations and methods of use. Surprisingly, this subclass of Formula (I) defined herein, when associated with an agriculturally active entity behave in an unexpected manner by increasing the efficacy of the agriculturally active entity in various ways, such as by improving solubility of the agriculturally active entity in the formulation, by improving adhesion of the agriculturally active entity to plant surfaces, by improving the water-fastness (including rain-fastness to the active entity being washed off the plant by rain) of the agriculturally active entity to the plant or seed, by improving the penetration (absorption) of the agriculturally active entity into plant tissues, by increasing soil penetration of the agriculturally active entity to reach the plant roots or under soil parts, or by reducing soil adhesion of the agriculturally active entity to reach the plant roots or under soil parts, or reducing enzymatic degradation of the agriculturally active entity by the plant or seed or microorganisms in the soil. Also environmental impact is reduced as fewer applications of the formulation are needed and/or lower doses are required.

General Syntheses Used to Prepare PEHAM Dendritic Polymers

PEHAM dendritic polymers of the present invention are a formulation for use in agriculture comprising at least one PEHAM dendrimer of the formula:

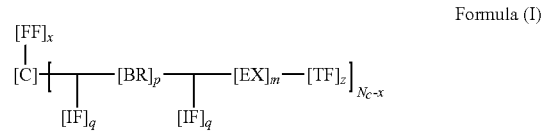

Formula (I)

wherein:
(C) means a core selected from the group consisting of PETGE, PETriGE and TMPTGE;
(FF) means a focal point functionality component of the core selected from the group consisting of Et, OH, SH, $NH_2$, $CO_2H$, carboxylate esters, straight- or branch chain $C_1$-$C_{18}$ alkyl, aryl, aryl heterocyclic moieties, $C_1$-$C_3$ alkoxy, triazole, $C_1$-$C_{18}$ alkyl esters, polyethyleneglycol and polyfluorinated moieties;
x is independently 0 or 1;
(BR) means a branch cell, which if p is greater than 1, then (BR) may be the same or a different moiety, selected from the group consisting of DBA, DEA, DEIDA, DETA, DIA, IDA, IDADS, PETriGE, TREN, TRIS, bis(2-methoxyethyl)amine, methylacrylate, N,N-di-Hexylamino, proparyl alcohol and trimethylamino;
p is the total number of branch cells (BR) in the dendrimer and is an integer derived by the following equation $$p = \text{Total \# of } [BR] = \left(\frac{N_b^1}{N_b} + \frac{N_b^2}{N_b} + \frac{N_b^3}{N_b} + \ldots \frac{N_b^G}{N_b}\right)[N_c] = \left(\sum_{i=0}^{i=G-1} N_b^i\right)[N_c]$$

where: G is number of concentric branch cell shells (generation) surrounding the core which is 0, 1, 2 or 3;
i is final generation G;
$N_b$ is branch cell multiplicity; and
$N_c$ is core multiplicity and is an integer from 1 to 4;
with the proviso that when x is 1, $N_c$-x must be an integer from 1 to 3;
(IF) means interior functionality, which is OH;
q is independently 0 or an integer from 1 to 64;
(EX) means an extender, which, if m is greater than 1, then (EX) may be the same or a different moiety, selected from the group consisting of amino acids such as lysine, poly(amino acids) such as polylysine, oligoethyleneglycols, EDA, diethylenetetraamine and higher amine analogs, oligoalkylenamines protected as 5-membered imidazolidyl derivatives, fatty acids with di- or greater heterogeneous or homogenous functionality, unsaturated aliphatic and aromatic difunctional or polyfunctional moieties, EA, morpholine, dicarboxylic acids, EPC, IMAE, aryl dimercaptans, dimercaptoalkanes, triazoles, DMI, diazides, diacetylenes, pyrrolidone, pyrrolidone esters, aminoalkyl imidazolines, imidazolidines, poly(alkyleneimidazolidines), mercaptoalkylamines, hydroxyalkylamines or heterogeneous unsaturated aliphatic and aromatic difunctional or polyfunctional moieties;

m is independently 0 or an integer from 1 to 64;

when both q and m are greater then 1, (BR) and (EX) may occur alternately with the other moiety or sequentially with multiple groups of (BR) or (EX) occurring in succession;

(TF) means a terminal functionality, which, if z is greater than 1, then (TF) may be the same or a different moiety selected from the group consisting of amino, methylamino, ethylamino, hydroxyethylamino, benzylamino, mercaptoethylamino, dimethylamino, diethylamino, bis(hydroxymethyl)amino, N-alkylated amino derivatives, N-arylated amino derivatives, N-acylated amino derivatives, $CO_2$—$N(C_1$-$C_6$ alkyl), hydroxyl, mercapto, carboxyl, carboxylate salts, carboxy $C_1$-$C_{18}$ alkyl, straight- or branch chain $C_2$-$C_{18}$ alkenyl, methalkyl, amido, halo, urea, oxiranyl, aziridinyl, oxazolinyl, imidazolinyl, pyrrolidone, benzyl, phenyl, sulfonato, phosphonate, isocyanate, isothiocyanato, piperazinyl, ethyl piperazinyl, acrylate, methacrylate, acrylamides, azide, epoxide, ethyl imines, straight- or branch chain $C_1$-$C_{18}$ alkyl, $C_1$-$C_3$ alkoxy, $C_1$-$C_{18}$ alkyl esters, cyclic ethers, fatty amines, thiorane, morpholinyl, protected DETA, polyethyleneglycol, polyfluorinated moieties, and dendrons;

z means the number of surface groups from 1 to the theoretical number possible for (C) and (BR) for a given generation G and is derived by the following equation $$z = N_c N_b^G;$$

where: G, $N_b$ and $N_c$ are defined as above; and
with the proviso that at least one of (EX) or (IF) is present;
associated with at least one agriculturally active entity; and
at least one agriculturally-acceptable diluent or carrier; and
wherein the efficacy or duration of activity of the agriculturally active entity is increased.

In some embodiments, m is 0 and (EX) is absent. In some embodiments, q is an integer from 1 to 64 and (IF) is present.

In some embodiments, the agriculturally active entity is an insecticide, herbicide, fungicide, or plant hormone. In some embodiments, the agriculturally active entity is abamectin, acephate, acetochlor, acifluorfen, alachlor, atrazine, benefin, benomyl, bentazon, captan, carbofuran, chloropicrin, carbaryl, chlorothalanil, chlorothalonil, chlorpyrifos, chlorsulfuron cyanazine, copper hydroxide, copper sulfate, cyhexatin, cypermithrin, dalapon, 2,4-dichlorophenoxyacetic acid (2,4-D), DCPA, diazinon, dicamba, diclofop methyl, dimethenamid, diflubenzuron, dinoseb, diuron, endothall, EPTC, ethephon, ferbam, fluazifop, glyphosate, haloxyfop, imidacloprid malathion, mancozeb, MCPP, metalaxyl, metalaxyl-M, metolachlor, matolachlor-s, metribuzin, MSMA, naptalam; pendimethalin, permethrin, picloram, propachlor, propanil, sethoxydin, simazine, S-metolachlor, sulfentrazone, sulfosate, temephos, terbufos, triclopyr, trifluralin, triforine, or zineb. In some embodiments, the formulation is in the form of an agriculturally-acceptable powder, dust, granule, liquid, concentrate, suspension, emulsion, spray, gel, or aerosol. In some embodiments, the agriculturally active entity is controllably released from the formulation.

In one embodiment, the PEHAM dendrimer can be, but is not limited to, the following formulation:

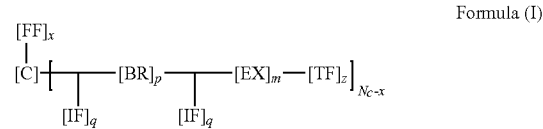

Formula (I)

wherein:
(C) means a core consisting of trimethylolpropane triglycidyl ether (TMPTGE);
(FF) means a focal point functionality component of the core consisting of Et;
x is independently 1;
(BR) means a branch cell, which if p is greater than 1, then (BR) may be the same or a different moiety, selected from the group consisting of diethanolamine (DEA), diethylenetriamine (DETA), and iminodiacetic acid (IDA);
p is the total number of branch cells (BR) in the dendrimer and is an integer derived by the following equation $$p = \text{Total \# of } [BR] = \left(\frac{N_b^1}{N_b} + \frac{N_b^2}{N_b} + \frac{N_b^3}{N_b} + \ldots \frac{N_b^G}{N_b}\right)[N_c] = \left(\sum_{i=0}^{i=G-1} N_b^i\right)[N_c]$$

where: G is number of concentric branch cell shells (generation) surrounding the core which is 1, 2, or 3;
i is final generation G;
$N_b$ is branch cell multiplicity; and
$N_c$ is core multiplicity and is an integer of 4;
(IF) means interior functionality, which is OH;
q is independently 0 or an integer from 1 to 64;
m is independently 0 and (EX) is absent;
z means the number of surface groups from 1 to the theoretical number possible for (C) and (BR) for a given generation G and is derived by the following equation $$z = N_c N_b^G;$$

wherein G, $N_b$ and $N_c$ are defined as above;
(TF) means a terminal functionality, which, if z is greater than 1, then (TF) may be the same or a different moiety selected from the group consisting of an amino, a carboxylate salt, a hydroxyl, and a methoxy;
associated with at least one agriculturally active entity; and
at least one agriculturally-acceptable diluent or carrier; and
wherein the efficacy or duration of activity of the agriculturally active entity is increased.

In one embodiment, the agriculturally active entity is an insecticide, herbicide, fungicide, or plant hormone. In one embodiment, the agriculturally active entity is atrazine, glyphosate, imidacloprid, and trifluralin. The formulation is in the form of an agriculturally-acceptable powder, dust, granule, liquid, concentrate, suspension, emulsion, spray, gel, or aerosol.

In some embodiments, the present invention features a method for treating plants or plant seeds with any of formulation as described herein, said method comprising administering the formulation to the plants, the plant seeds, or soil.

In some embodiments, the formulation increases the solubility of the agriculturally active entity. In some embodiments, the formulation improves adhesion of the agriculturally active entity to surfaces of the plants. In some embodiments, the formulation improves water-fastness of the agriculturally active entity to the plants or plant seeds. In some embodiments, the formulation improves penetration (absorption) of the agriculturally active entity into plant tissues of plants or plant seeds. In some embodiments, the formulation increases soil penetration of the agriculturally active entity. In some embodiments, the formulation reduces soil adhesion of the agriculturally active entity, wherein the agriculturally active entity migrates through the soil to reach plant roots or under soil parts. In some embodiments, the formulation reduces enzymatic degradation of the agriculturally active entity by the plants or plant seeds or microorganisms in the soil.

In some embodiments, the G of any PEHAM dendrimer for this invention is 0, 1, 2 or 3, with 0, 1 and 2 preferred. It is possible to have half generations such as 0.5, 1.5 etc. when the (TF) has a carboxylate or carboxylic groups. These groups are thought of historically as half way to an amine terminal functionality (for PAMAM dendrimers). The (EX) groups can be any of those listed but especially preferred are unsaturated aliphatic and aromatic difunctional or polyfunctional moieties, EA, morpholine, dicarboxylic acids, EPC, IMAE, aryl dimercaptans, dimercaptoalkanes, triazoles, DMI, diazides, diacetylenes, pyrrolidone, pyrrolidone esters, aminoalkyl imidazolines, imidazolidines, poly(alkyleneimidazolidines), mercaptoalkylamines, and hydroxyalkylamines, and more preferred is triazole, piperadine or morpholine. The (TF) groups can be any of the above, but preferably are OH, $CO_2Et$, carboxy salts, $CO_2$—N(tetra alkyl) and $NH_2$. The (BR) groups are those above but preferred are DEA, DEIDA, DETA, IDA, TREN, and TRIS. The (FF) groups are Et and OH. The presence of one or more (IF) groups are preferred, where (IF) is OH.

In some embodiments, the PEHAM dendrimer of Formula (I) can be, but is not limited to, any one of the following formulations:

[(C)=TMPTGE; (FF)=Et; (IF1)=OH; (BR1)=DEA;
 (TF)=OH; G=1];

[(C)=TMPTGE; (FF)=Et; (IF1)=OH; (BR1)=TRIS;
 (TF)=OH; G=1];

[(C)=PETGE; (IF1)=OH; (EX1)=Triazole; (BR1)
 =PETriGE; (IF2)=OH; (BR2)=DEA; (TF)=OH;
 G=2];

[(C)=TMPTGE; (FF)=Et; (IF1)=OH; (BR1)=IDA;
 (TF)=CO2Na; G=1];

[(C)=TMPTGE; (FF)=Et; (IF1)=OH; (BR1)=IDA;
 (TF)=CO2NBu4; G=1];

[(C)=TMPTGE; (FF)=Et; (IF1)=OH; (BR1)=DETA;
 (TF)=Primary NH2; G=1]; or

[(C)=TMPTGE; (FF)=Et; (IF1)=OH; (BR1)=DIA;
 (TF)=Primary NH2; G=1].

A process to prepare the dendritic polymers of Formula (I) can be by ring-opening reaction system which comprises:

A. Reacting an epoxy functional core with an amine functional extender, such as shown below:

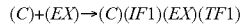

where (C)=an epoxy functional core such as PETGE; (IF1)=Internal hydroxyl (OH); (EX)=Triazole; (TF1)= Amine; and B. Reacting an amine functional extended core reagent (C) (IF1) (EX) (TF1) with an epoxy functional branch cell reagent such as shown below:

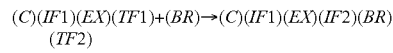

where (C)=PETGE; (IF1)=Internal functionality moiety such as OH; (EX)=an extender moiety such as morpholine; (TF1)=Amine; (BR)=an epoxy functional branch cell reagent such as PETriGE; and (IF2)=Internal functionality moiety such as OH; (TF2)=Amine; and wherein for both Steps A and B
  the addition of an extender (EX) group to a core, the mole ratio of (EX)/(C) is defined as the moles of extender molecules (EX) to the moles of reactive functional groups on the simple core or current generation structure (i.e. $N_c$) where an excess of (EX) is used when full coverage is desired;
  the addition of a branch cell (BR) to a simple core or current generation structure (BR)/(C) is defined as the moles of branch cell molecules (BR) to the moles of reactive functional groups on the simple core or current generation structure (i.e. $N_c$) where an excess of (BR) is used when full coverage is desired; and
  the level of addition of branch cells (BR) or extenders (EX) to a core or current generational product can be controlled by the mole ratio added or by N-SIS.

An orthogonal chemical approach is the 1,3-dipolar cyclo-addition of azides containing (C) and (BR) to alkynes containing (C) and (BR). The alkyne containing (C) may have from 1 to $N_c$ alkyne moieties present and alkyne containing (BR) may have from 1 to $N_b$-1 alkyne moieties. The other reactive groups present in (C) or (BR) can be any of the (BR) groups listed herein before. Azide containing (C) and (BR) are produced by nucleophilic ring-opening of epoxy rings with azide ions. Subsequent reaction of these reactive groups can provide triazole linkages to new (BR) or (TF) moieties using "click" chemistry as described by Michael Malkoch et al., in J. Am. Chem. Soc. 127, 14942-14949 (2005).

WO 2007/149501 teaches a MWA synthesis that exhibits unexpected and dramatic advantages compared to thermal processing. It was observed that MWA produced higher purity dendritic polymer products (i.e., dendrimers/dendrons) under more mild conditions, shorter reaction times (minutes versus days), while requiring only stoichiometric amounts or slight excess of reacting reagents. The dendritic polymer as the starting material or a desired (C) is reacted with a BR or EX to obtain the desired dendritic polymer product. Suitable solvents can be used if the reactant does not also serve as the solvent. The mild conditions for the reaction compared to that of the prior thermal reaction leads to less by-products, fewer steps for purification of the desired dendritic polymer product. The reaction times are significantly reduced compared to the prior thermal process. Thus this MWA synthesis is less expensive to run to make the product desired.

Any of these above processes can be used to make the PEHAM dendrimers of Formula (I).

These Formula (I) dendrimers, which are a selection invention of the PEHAM dendrimers of U.S. Ser. No. 10/594,776, filed 20 Apr. 2005 (published as US 2007/0244296 on Oct. 18, 2007) and U.S. Ser. No. 11/630,044, filed Dec. 21, 2005 (published as US 2007/0298006 on Dec. 27, 2007), are surprisingly effective for use in these agricultural formulations. Their size, higher (TF) for their low G keeps costs lower, easier to make, and conveys desirable properties that were not predictable for such formulations. Such properties include increasing the efficacy of the active agent in various ways, such as by improving solubility of the active agent in the formulation, by improving adhesion and penetration of the active agent to plant surfaces, by improving the water-fastness of the active agent to the plant or seed, by increasing soil penetration of the active agent to reach the plant roots or under soil parts, or by reducing soil adhesion of the active agent to reach the plant roots or under soil parts, or reducing enzymatic degradation of the active agent by the plant or seed or microorganisms in the soil.

The agriculturally active entity that is encapsulated or associated with these dendrimers may be selected from a very large group of possible moieties that meet the desired purpose. Such materials include, but are not limited to in vivo or in vitro or ex vivo use in plants or their seeds, or plant pests, growth hormones, or microorganisms, viruses and any living system, which material can be associated with these PEHAM dendrimers without appreciably disturbing the physical integrity of the dendrimer.

The agriculturally active entity of this present formulation is any entity that is useful for application to plants or their seeds to increase crop yields, reduce competitive plants, stunt or kill weeds, or for the prevention or treatment of pests and which agriculturally active entity can be associated with the PEHAM dendrimer without appreciably disturbing the physical integrity of the PEHAM dendrimer. For example, Fe, Gd, or Mn; hormones; biological response modifiers, such as interleukins, interferons, viruses and viral fragments; pesticides, including antimicrobials, algaecides, arithelmetics, acaricides, insecticides, attractants, repellants; herbicides and/or fungicides, such as abamectin, acephate, acetochlor, acifluorfen, alachlor, atrazine, benefin, benomyl, bentazon, captan, carbofuran, chloropicrin, carbaryl, chlorothalanil, chlorothalonil, chlorpyrifos, chlorsulfuron cyanazine, copper hydroxide, copper sulfate, cyhexatin, cypermithrin, dalapon, 2,4-dichlorophenoxyacetic acid (2,4-D), DCPA, diazinon, dicamba, diclofop methyl, dimethenamid, diflubenzuron, dinoseb, diuron, endothall, EPTC, ethephon, ferbam, fluazifop, glyphosate, haloxyfop, malathion, mancozeb, MCPP, metalaxyl, metalaxyl-M, metolachlor, matolachlor-s, metribuzin, MSMA, naptalam; pendimethalin, permethrin, picloram, propachlor, propanil, sethoxydin, simazine, S-metolachlor, sulfentrazone, sulfosate, temephos, terbufos, triclopyr, trifluralin, triforine, and zineb.

In general, the pesticide and/or growth regulating active substances which may enter into the formulation of this invention as an agriculturally active entity are those listed in any plant-protection manual, for example L'Index Phytosanitaire (published by the Technical Directorate of the Association de Coordination Technique Agricole or A.C.T.A.) or The Pesticide Manual (by the British Crop Protection Council) or The Electronic Pesticide Manual (by the British Crop Protection Council). Some plant growth regulators that can be used as an agriculturally active entity, either alone or in combination with other active substances in the formulations of this invention are: abscisic acid; ACC; ancymidol; aviglycine; benzofluor; benzyladenine; brassinolide; buminafos; butralin; calcium cyanamide; carbaryl; carvone; chlorfluren; chlorflurenol; chlormequat; chlorphonium; chlorpropham; ciobutide; clofencet; clofibric acid; cloxyfonac; 4-CPA; cyanamide; cyclanilide; cycloheximide; cyprosulfamide; 2,4-D; daminozide; 2,4-DB; 2,4-DEP; dichlorflurenol; dichlorprop; dikegulac; dimethipin; endothal; epocholeone; etacelasil; ethephon; ethychlozate; ethylene; fenoprop; fenridazon; flumetralin; fluoridamid; flurenol; flurprimidol; forchlorfenuron; fosamine; gibberellic acid; gibberellins; glyoxime; glyphosine; heptopargil; holosulf; hymexazol; IAA; IBA; inabenfide; isopyrimol; jasmonic acid; karetazan; kinetin; lead arsenate; maleic hydrazide; mefluidide; mepiquat; merphos; methasulfocarb; 1-methylcyclopropene; metoxuron; α-naphthaleneacetic acid; naphthaleneacetamide; 1-naphthol; naphthoxyacetic acid; 2iP; paclobutrazol; pentachlorophenol; piproctanyl; potassium naphthenate; prohexadione; prohydrojasmon; propham; pydanon; sintofen; sodium naphthenate; 2,4,5-T; tetcyclacis; thidiazuron; triapenthenol; tribufos; 2,3,5-triiodobenzoic acid; trinexapac; uniconazole; and zeatin.

Some of the fungicide substances that can be used as an agriculturally active entity, either alone or in combination with others active substances, in the formulation of this invention are: 2-phenylphenol; 8-hydroxyquinoline sulfate; AC 382042; *Ampelomyces quisqualis*; acibenzolar; acypetacs; aldimorph; allyl alcohol; ametoctradin; amisulbrom; ampropylfos; anilazine; aureofungin; azaconazole; azoxystrobin; azithiram; azoxystrobin; *Bacillus subtilis*; barium polysulfide; benalaxyl; benalaxyl-M; benodanil; benomyl; benquinox; bentaluron; benthiavalicarb; benzalkonium chloride; benzamacril; benzamorf; benzohydroxamic acid; bethoxazin; binapacryl; biphenyl; bitertanol; bithionol; bixafen; blasticidin-S; borax; Bordeaux mixture; boscalid; bromuconazole; bupirimate; Burgundy mixture; buthiobate; butylamine; calboxin; calcium polysulfide; captafol; captan; carbamorph; carbendazim; carboxin; carpropamid (KTU 3616); carvone; Cheshunt mixture; CGA 279202; chinomethionat; chlobenthiazone; chloraniformethan; chloranil; chlorfenazole; chlorodinitronaphthalene; chloroneb; chloropicrin; chlorothalonil; chlorquinox; chlozolinate; climbazole; clotrimazole; copper acetate; copper carbonate—basic; copper hydroxide; copper naphthenate; copper oleate; copper oxychloride; copper silicate; copper sulfate; copper sulfate—basic; copper zinc chromate; cresol; cufraneb; cuprobam; cuprous oxide; cyazofamid; cyclafuramid; cycloheximide; cyflufenamid; cymoxanil; cypendazole; cyproconazole; cyprodinil; dazomet; DBCP; debacarb; decafentin; dehydroacetic acid; dichlofluanid; dichlone; dichlorophen; dichlozoline; diclobutrazol; diclocymet; dichlomezine; dicloran; dichlorophen; diclocymet; diethofencarb; diethyl pyrocarbonate; difenoconazole; difenzoquat; difenzoquat metilsulfate; diflumetorim; dimethirimol; dimethomorph; dimoxystrobin; diniconazole; diniconazole-M; dinobuton; dinocap; dinocap-4; dinocap-6; dinocton; dinopenton; dinosulfon; dinoterbon; diphnenylamine; dipyrithione; disulfiram; ditalimfos; ditalimfos; dithianon; DNOC; dodemorph; dodemorph acetate; dodine; Dodine free base; drazoxolon; edifenphos; epoxiconazole (BAS 480F); etaconazole; etem; ethaboxam; ethasulfocarb; ethirimol; ethoxyquin; ethylmercury 2,3-dihydroxypropyl mercaptide; ethylmercury acetate; ethylmercury bromide; ethylmercury chloride; ethylmercury phosphate; (3-ethoxypropyl)mercury bromide; etridiazole; famoxadone; fenamidone; fenaminosulf; fenapanil; fenarimol; fenbuconazole; fenfin; fenfuram; fenhexamid; fenitropan; fenoxanil; fenpiclonil; fenpropidin; fenpropimorph; fentin; fentin acetate; fentin hydroxide; ferbam; ferimzone; fluazinam; fludioxonil; flumetover; flumorph; fluopicolide; fluopyram; fluoroimide; fluotrimazole; fluoxastrobin; fluquinconazole; flusilazole; flusulfamide; flutianil; flutolanil; flutriafol; folpet; formaldehyde; fosetyl; fosetyl-aluminum; fuberidazole; furalaxyl; furametpyr; furcarbanil; furconazole; furconazole-cis; furfural; furmecyclox; furophanate; *Fusarium oxysporum; Gliocladium virens*; glyodin; griseofulvin; guazatine; guazatine acetates; GY-81; halacrinate; hexachlorobenzene; hexachlorobutadiene; hexaconazole; hexylthiofos; hydrargaphen; 8-hydroxyquinoline sulfate; hymexazol; ICIA0858; IKF-916; imazalil; imazalil sulfate; imibenconazole; iminoctadine; Iminoctadine triacetate; iminoctadine tris[Albesilate]; iodomethane; ipconazole; iprobenfos; Iprodione; iprovalicarb; isoprothiolane; isopyrazam; isotianil; isovaledione; kasugamycin; Kasugamycin hydrochloride hydrate; Kresoxim-methyl; mancopper; mancozeb; mandipropamid; maneb; mebenil; mecarbinzid; mepanipyrim; mepronil; meptyldinocap; mercuric chloride; mercuric oxide; mercurous chloride; metalaxyl; metalaxyl-M; metam; metam-sodium; metazoxolon; metconazole; methasulfocarb; methfuroxam; 2-methoxyethylmercury chloride; methyl bromide; methyl isothiocyanate; methylmercury benzoate; methylmercury dicyandiamide; methylmercury pentachlorophenoxide; metiram; metominostrobin (SSF-126); metrafenone; metsulfovax; milneb; MON65500; myclotbutanil; myclobutanil; myclozolin; N-(ethylmercury)-p-toluenesulphonanilide; nabam; naphthenic acid; natamycin; nickel bis (dimethyldithiocarbamate); nitrostyrene; nitrothalisopropyl; nuarimol; OCH; octhilinone; ofurace; oleic acid (fatty acids); orysastrobin; oxadixyl; oxine-copper; oxpoconazole; oxycarboxin; pefurazoate; penconazole; pencycuron; penflufen; pentachlorophenol; pentachlorophenyl laurate; penthiopyrad; perfurazoate; 8-phenyl-mercurioxyquinoline; phenylmercuriurea; phenylmercury acetate; phenylmercury chloride; phenylmercury derivative of pyrocatechol; phenylmercury nitrate; phenylmercury salicylate; 2-phenylphenol; *Phlebiopsis gigantea*; phosdiphen; phthalide; picoxystrobin; piperalin; polycarbamate; polyoxin B; polyoxins; polyoxorim; potassium azide; potassium hydroxyquinoline sulfate; potassium polysulfide; potassium thiocyanate; probenazole; prochloraz; procymidone; propamocarb; propamocarb hydrochloride; propiconazole; propineb; proquinazid; prothiocarb; prothioconazole; pyracarbolid; pyraclostrobin; pyrametostrobin; pyraoxystrobin; pyrazophos; pyribencarb; pyributicarb; pyridinitril; pyrifenox; pyrimethanil; pyroquilon; pyroxychlor; pyroxyfur; quinacetol; quinazamid; quinconazole; quinoxyfen; quintozene; rabenzazole; RH-7281; salicylanilide; sec-butylamine; sedaxane; silthiofam; simeconazole; sodium azide; sodium orthophenylphenoxide; sodium pentachlorophenoxide; sodium 2-phenylphenoxide; sodium pentachlorophenoxide; sodium polysulfide; spiroxamine (KWG 4168); *Streptomyces griseoviridis*; streptomycin; sulfur; sultropen; tar oils; TCMTB; tebuconazole; tebufloquin; tecloftalam; tecnazene; tecoram; tetraconazole; thiabendazole; thiadifluor; thicyofen; thifluzamide; thiochlorfenphim; thiomersal; thiophanate; thiophanate-methyl; thioquinox; thiram; tiadinil; tioxymid; tolclofos-methyl; tolylfluanid; tolylmercury acetate; triadimefon; triadimenol; triamiphos; triarimol; triazbutil; triazoxide; tributyltin oxide; trichlamide; *Trichoderma harzianum*; tricyclazole; tridemorph; trifloxystrobin; triflumizole; triforine; triticonzole; uniconazole; uniconazole-P; validamycin; valifenalate; vinclozolin; zarilamid; zinc naphthenate; zineb; ziram; zoxamide; the compounds having the chemical name methyl (E,E)-2-(2-(1-(1-(2-pyridyl) propyloxyimino)-1-cyclopropylmethyloxy-methyl)phenyl)-3-ethoxypropenoate; and 3-(3,5-dichlorophenyl)-4-chloropyrazole.

Examples of insecticide, acaricide and nematocide active substances which may be used alone or in combination with other active substances, in particular pesticides, used as an agriculturally active entity in the formulations of this invention, are: abamectin; acephate; acetamiprid; acethion; acetoprole; acrinathrin; acrylonitrile; aldicarb; alanycarb; aldoxycarb; aldrin; allethrin [(1R) isomers]; a-cypermethrin; allosamidin; allyxycarb; alpha-cypermethrin; alpha-endosulfan; amidithion; aminocarb; amiton; amitraz; anabasine; athidathion; avermectin B1 and its derivatives; azadirachtin; azamethiphos; azinphos-ethyl; azinphos-methyl; azinphosmethyl; azothoate; *Bacillus thurigiensi*; barium hexafluorosilicate; barthrin; bendiocarb; benfuracarb; bensultap; beta-cyfluthrin; beta-cypermethrin; bifenazate; bifenthrin; bioallathrin; bioallethrin (S-cyclopentenyl isomer); bioethanomethrin; biopermethrin; bioresmethrin; bistrifluron; borax; boric acid; bromfenvinfos; bromocyclen; bromo-DDT; bromophos; bromophos-ethyl; bufencarb; buprofezin; butacarb; butathiofos; butocarboxim; butonate; butoxycarboxim; cadusafos; calcium arsenate; calcium polysulfide; camphechlor; carbanolate; carbaryl; carbofuran; carbon disulfide; carbon tetrachloride; carbophenothion; carbosulfan; cartap; cartap hydrochloride; chlorantraniliprole; chlorbicyclen; chordane; chlordecone; chlordimeform; chlorethoxyfos; chlorfenapyr; chlorfenvirnphos; chlorfluazuron; chlormephos; chloroform; chloropicrin; chlorphoxim; chlorprazophos; chlorpyrifos; chlorpyrifos-methyl; chlorthiophos; chromafenozide; cinerin I; cinerin II; cinerins; cismethrin; cloethocarb; closantel; clothianidin; clothianidin; copper acetoarsenite; copper arsenate; copper naphthenate; copper oleate; coumaphos; Cryolite; Cryomazine; Cyanophos; calcium cyanide; sodium cyanide; coumithoate; crotamiton; crotoxyphos; crufomate; cryolite; cyanofenphos; cyanophos; cyanthoate; cyantraniliprole; cyantraniliprole; cyclethrin; cycloprothrin; cyfluthrin; cyhalothrin; cypermethrin; cyphenothrin [(1R) transisomers]; 13-cyfluthrin; 13-cypermethrin; cyromazine; cythioate; dazomet; DDT; decarbofuran; deltamethrin; demephion; demephion-O; demephion-S; demeton; demeton-methyl; demeton-O; demeton-O-methyl; demeton-S; demeton-S-methyl; demeton-S-methylsulphon; diafenthiuron; dialifos; diatomaceous earth; diazinon; dicapthon; dichlofenthion; 1,2-dichloropropane; dichlorvos; dicofol; dicresyl; dicrotophos; dicyclanil; dieldrin; diflubenzuron; dilor; dimefluthrin; dimefox; dimetan; dimethoate; dimethrin; dimethylvinphos; dimetilan; dimetilan; dinex; dinoprop; dinosam; dinotefuran; diofenolan; dioxabenzofos; dioxacarb; dioxathion; disulfoton; dithicrofos; d-limonene; doramectin; DNOC; DPXJW062 and DP; α-ecdysone; ecdysterone; emamectin; EMPC; empenthrin [(EZ)-(1R) isomers]; endosulfan; ENT 8184; EPN; endothion; endrin; EPN; epofenonane; eprinomectin; esfenvalerate; etaphos; ethiofencarb; ethion; ethoate-methyl; ethoprophos; ethyl formate; ethyl-DDD; ethylene dibromide; ethylene dichloride; ethiprole [having the chemical name 5-amino-3-cyano-1-(2, 6-dichloro-4-trifluoromethylphenyl)-4-ethylsulfinylpyrazole]; ethylene oxide; etofenprox; Etoxazole; Etrimfos; EXD; famphur; fenamiphos; fenazaflor; fenchlorphos; fenethacarb; fenfluthrin; fenitrothion; fenobucarb; fenoxacrim; fenoxycarb; fenpirithrin; fenpropathrin; fensulfothion; fenthion; fenthion-ethyl; fenvalerate; fipronil and the compounds of the arylpyrazole family; flonicamid; flubendiamide; flucofuron; flucycloxuron; flucythrinate; flufenerim; flufenoxuron; flufenprox; flumethrin; fluofenprox; fluvalinate; fonofos; formetanate; formparanate; formetanate hydrochloride; formothion; fosmethilan; fospirate; fosthietan; furathiocarb; furethrin; gamma-cyhalothrin; gamma-HCH; GY-81; halfenprox; halofenozide; HCH; HEOD; heptachlor; heptenophos; heterophos; hexaflumuron; sodium hexafluorosilicate; HHDN; hydramethylnon; hydrogen cyanide; hydroprene; hyquincarb; imidacloprid; imiprothrin; indoxacarb; iodomethane;

IPSP; isazofos; isobenzan; isocarbophos; isodrin; isofenphos; isofenphos-methyl; isoprocarb; isoprothiolane; isothioate; methyl isothiocyanal; isoxathion; ivermectin; jasmolin I; jasmolin II; jodfenphos; juvenile hormone I; juvenile hormone II; juvenile hormone III; kelevan; kinoprene; lambda-cyhalothrin; pentachlorophenyl laurate; lead arsenate; lepimectin; leptophos; lindane; lirimfos; lufenuron; lythidathion; malathion; MB-599; malonoben; mazidox; mecarbam; mecarphon; menazon; mephosfolan; mercurous chloride; mesulfenfos; metaflumizone; methacrifos; methamidophos; methidathion; methiocarb; methocrotophos; methomyl; methoprene; methoxychlor; methoxyfenozide; methyl bromide; methylchloroform; methylene chloride; metofluthrin; metolcarb; metoxadiazone; mevinphos; mexacarbate; milbemectin and its derivatives; milbemycin oxime; mipafox; mirex; monocrotophos; morphothion; moxidectin; naftalofos; naled; naphthalene; nicotine; nifluridide; nitenpyram; nithiazine; nitrilacarb; novaluron; noviflumuron; petroleum oils; tar oils; oleic acid; omethoate; oxamyl; oxydemeton-methyl; oxydeprofos; oxydisulfoton; *Paecilomyces fumosoroseus*; para-dichlorobenzene; parathion; parathion-methyl; penfluron; pentachlorophenol; sodium pentachlorophenoxide; permethrin; phenkapton; phenothrin [(1R)-transisomers]; phenthoate; phorate; phosalone; phosfolan; phosmet; Phosphamidon; piperonyl butoxide; phosphine; aluminum phosphide; magnesium phosphide; zinc phosphide; phosnichlor; phosphamidon; phosphine; phoxim; phoxim-methyl; pirimetaphos; pirimicarb; pirimiphos-ethyl; pirimiphos-methyl; calcium polysulfide; plifenate; potassium arsenite; potassium thiocyanate; pp'-DDT; prallethrin; precocene I; precocene II; precocene III; primidophos; profenfos; profluthrin; promacyl; promecarb; propaphos; propetamphos; propoxur; prothidathion; prothiofos; prothoate; protrifenbute; pyraclofos; pyrafluprole; pyrazophos; pyresmethrin; pyrethrin I; pyrethrin II; pyrethrins (chrysanthemates, pyrethrates, pyrethrum); pyretrozine; pyridaben; pyridalyl; pyridaphenthion; pyrifluquinazon; pyrimidifen; pyrimitate; pyriprole; pyriproxyfen; quassia; quinalphos; quinalphos-methyl; quinothion; rafoxanide; resmethrin; RH-2485; rotenone; RU 15525; ryania; sabadilla; schradan; selamectin; silafluofen; silica gel; sodium arsenite; sodium fluoride; sodium hexafluorosilicate; sodium thiocyanate; sophamide; spinetoram; spinosad; spiromesifen; spirotetramat; sulcofuron; sulcofuron-sodium; sulfluramide; sulfotep; sulfoxaflor; sulfuryl fluoride; sulprofos; ta-fluvalinate; tazimcarb; TDE; tebufenozide; tebufenpyrad; tebupirimfos; teflubenzuron; tefluthrin; temephos; TEPP; terallethrin; terbufos; tetrachloroethane; tetrachlorvinphos; tetramethrin; tetramethrin [(1R) isomers]; tetramethylfluthrin; theta-cypermethrin; 0-cypermethrin; thiacloprid; thiametoxam; thicrofos; thiocarboxime; thiocyclam; thiocyclam hydrogen oxalate; thiodicarb; thiofanox; thiometon; thiosultap; thuringiensin; tolfenpyrad; tralomethrin; transfluthrin; transpermethrin; triarathene; triazamate; triazophos; trichlorfon; trichlormetaphos-3; trichloronat; trifenofos; triflumuron; trimethacarb; triprene; vamidothion; vaniliprole; XDE-105; XMC; xylylcarb; Zeta-cypermethrin; zolaprofos; and ZXI 8901; the compound whose chemical name is 3-acetyl-5-amino-142,6-dichloro-4-(trifluoromethyl)phenyl]-2-methylsulfinylpyrazole.

Some of the herbicide active substances which may be used alone or in combination with other active substances, in particular pesticides, used as an agriculturally active entity in the formulations of this invention, are: 2,3,6-TBA; 2,4-D; 2,4-D-2-ethylhexyl; 2,4-DB; 2,4-DB-butyl; 2,4-DB-dimethyl-ammonium; 2,4-DB-isooctyl; 2,4-DB-potassium; 2,4-DB-sodium; 2,4-D-butotyl (2,4-D-Butotyl (2,4-D-Butoxyethyl Ester)); 2,4-D-butyl; 2,4-D-dimethylammonium; 2,4-D-Diolamine; 2,4-D-isoctyl; 2,4D-isopropyl; 2,4-D-sodium; 2,4-D-trolamine; acetochlor; acifluorfen; aclonifen; acifluorfen-sodium; acrolein; AKH-7088; alachlor; allidochlor; alloxydim; alloxydim-sodium; allyl alcohol; alorac; ametridione; ametryn; amibuzin; amicarbazone; amicarbazone; amidosulfuron; aminocyclopyrachlor; aminopyralid; aminopyralid; amiprofos-methyl; amitrole; ammonium sulfamate; anilofos; anisuron; asulam; asulam-sodium; atraton; atrazine; azafenidin; azimsulfuron; azimsulfuron; aziprotryne; barban; BCPC; beflubutamid; benazolin; benazolin-ethyl; bencarbazone; bencarbazone; benfluralin; benfuresate; benoxacor; bensulfuron; bensulfuron-methyl; bensulide; bentazone; bentazone-sodium; benofenap; benzadox; benzfendizone; benzipram; benzobicyclon; benzofenap; benzofluor; benzoylprop; benzthiazuron; benzthiazuron; bicyclopyrone; bifenox; bilanofos; bilanafos-sodium; bispyribac; bispyribac-sodium; borax; bromacil; bromobonil; bromobutide; brompyrazon; bromofenoxim; bromoxynil; bromoxynil-heptanoate; bromoxynil-octanoate; bromoxynil-potassium; butachlor; butafenacil; butamifos; butenachlor; buthidazole; buthiuron; butralin; butroxydim; buturon; butylate; cacodylic acid; cafenstrole; calcium chlorate; calcium cyanamide; cambendichlor; carbasulam; carbasulam; carbetamide; carboxazole; carboxazole; carfentrazone; carfentrazone-ethyl; CDEA; CEPC; chlomethoxyfen; chloramben; chloranocryl; chlorazifop; chlorazine; chlorbromuron; chlorbufam; chloreturon; chlorfenac; chlorfenprop; chlorflurazole; chlorflurenol; chloridazon; chlorimuron; chlorimuron-ethyl; chloroacetic acid; chlornitrofen; chloropon; chlorotoluron; chloroxuron; chloroxynil; chlorprocarb; chlorpropham; chlorsulfuron; chlorthal; chlorthal-dimethyl; chlorthiamid; cinidon-ethyl; cinmethylin; cinosulfuron; cisanilide; clethodim; cliodinate; clodinafop; clofop; clodinafoppropargyl; clomazone; clomeprop; clomeprop; cloprop; cloproxydim; clopyralid; clopyralidolamine; cloquintocet; cloquintocet-mexyl; cloransulam; chloransulam-methyl; CMA; copper sulfate; CPA; CPA-dimethylammonium; CPA-isoctyl; CPA-thioethyl; 4-CPA; 4-CPB; CPMF; 4-CPP; CPPC; credazine; cresol; cumyluron; cyanamide; cyanatryn; cyanazine; cycloate; cyclosulfamuron; cycloxydim; cycluron; cyhalofop; cyhalofop-butyl; cyperquat; cyprazine; cyprazole; cypromid; 2,4-D; 3,4-DA; daimuron; dalapon; dalapon-sodium; dazomet; desmeduipham; 2,4-DB; 3,4-DB; 2,4-DEB; delachlor; 2,4-DEP; desmedipham; desmetryn; di-allate; dicamba; dicambadimethylammonium; dicamba-potassium; dicambasodium; dicambatrolamine; dichlobenil; dichloralurea; dichlormid; dichlormate; dichlorprop; dichlorprop-butotyl (dichlorprop-butotyl (dichlorpropbutoxyethyl ester)); dichlorpropdimethylammonium; dichlorprop-isoctyl; dichlorprop-P; dichlorprop-potassium; diclofop; diclofop-methyl; diclosulam; diclosulam; diethamquat; diethatyl; difenopenten; difenoxuron; difenzoquat; difenzoquat metilsulfate; diflufenican; diflufenican; diflufenzopyr (BAS 654 00 H); dimefuron; dimepiperate; dimethachlor; dimethametryn; dimethenamid; dimethenamid-P; dimethipin; dimethylarsinic acid; dimexano; dimidazon; dinitramine; dinofenate; dinoprop; dinosam; dinoseb; dinoterb; dinoterbacetate; dinoterb-ammonium; dinoterb-diolamine; diphenamid; dipropetryn; diquat; diquat dibromide; disul; dithiopyr; diuron; DMPA; DNOC; 3,4-DP; DSMA; EBEP; eglinazine; endothal; epronaz; epronaz; EPTC; erbon; esprocarb; ethalfluralin; ethametsulfuron; ethametsulfuron-methyl; ethidimuron; ethiolate; ethofumesate; ethoxyfen; ethoxysulfuron; etinofen; etnipromid; etnipromid; etnipromid; etobenzanid; EXD; fenasulam; fenasulam; fenasulam;

fenchlorazole-ethyl; fenclorim; fenoprop; fenoxaprop; fenoxaprop-P; fenoxaprop-P-ethyl; fenoxasulfone; fenteracol; fenthiaprop; fenthiaprop; fentrazamide; fenuron; fenuron-TCA; ferrous sulfate; flamprop; flamprop-M; flamprop-M-isopropyl; flampropM-methyl; flazasulfuron; florasulam; florasulam; fluazifop; fluazifop-butyl; fluazifop-P; fluazifop-P-butyl; fluazolate; flucarbazone; flucarbazone; flucetosulfuron; fluchloralin; flufenacet (BAS FOE 5043); flufenican; flufenican; flufenpyr; flumetsulam; flumezin; flumiclorac; flumiclorac-pentyl; flumioxazin; flumipropyn; fluometuron; fluorodifen; fluoroglycofen; fluroglycofen-ethyl; fluoromidine; fluoronitrofen; fluothiuron; flupaxam; flupoxam; flupropacil; flupropanate; flupropanate-sodium; flupyrsulfuron; flupyrsulfuron-methylsodium; flurazole; flurenol; flurenol-butyl; fluridone; flurochloridone; fluroxypyr; fluroxypyr-2-butoxy-1-methylethyl; fluroxypyr-methyl; flurtamone; fluthiacet; fluthioacetmethyl; fluxofenim; fomesafen; fomesafen-sodium; foramsulfuron; fosamine; fosamine-ammonium; furilazole; furyloxyfen; glyphosate; glufosinate; glufosinate-ammonium; glufosinate-P; glyphosateammonium; glyphosate-isopropylammonium; glyphosatesodium; glyphosate-trimesium; halosafen; halosafen; halosulfuron; halosulfuron-methyl; haloxydine; haloxyfop; haloxyfop-P; haloxyfop-P-methyl; haloxyfopetotyl; haloxyfop-methyl; hexachloroacetone; hexaflurate; hexazinone; hilanafos; imazacluin; imazamethabenz; imazamox; imazapic; imazapyr; imazapyr-isopropylammonium; imazaquin; imazaquin-ammonium; imazemethabenzmethyl; imazethapyr; imazethapyr-ammonium; imazosulfuron; imizapic (AC 263,222); indanofan; indaziflam; iodobonil; iodomethane; iodosulfuron; ioxynil; ioxynil octanoate; ioxynil-sodium; ipazine; ipfencarbazone; ipfencarbazone; iprymidam; isocarbamid; isocil; isomethiozin; isonoruron; isopolinate; isopropalin; isoproturon; isouron; isoxaben; isoxachlortole; isoxaflutole; isoxapyrifop; karbutilate; lactofen; laxynel octanoate; laxynil-sodium; lenacil; linuron; MAA; MAMA; MCPA; MCPA-butotyl; MCPA-dimethylammonium; MCPA-isoctyl; MCPA-potassium; MCPA-sodium; MCPA-thioethyl; MCPB; MCPB-ethyl; MCPB-sodium; mecoprop; mecoprop-P; medinoterb; mefenacet; mefenpyr-diethyl; mefluidide; mesoprazine; mesosulfuron; mesulfuron-methyl; mesotrione; metam; metamifop; metamifop; metamitron; metam-sodium; metezachlor; methalpropalin; methazole; metazosulfuron; metflurazon; methabenzthiazuron; methiobencarb; methiozolin; methiuron; methometon; methoprotryne; methyl bromide; methyl isothiocyanate; methylarsonic acid; methyldymron; metobenzuron; metobromuron; metolachlor; metosulam; metoxuron; metribuzin; metsulfuron; molinate; monalide; monisouron; monisouron; monochloroacetic acid; monolinuron; monuron; morfamquat; MPB-sodium; MSMA; napropamide; naptalam; naptalam-sodium; neburon; nicosulfuron; nonanoic acid; nipyraclofen; nitralin; nitrofen; nitrofluorfen; norflurazon; noruron; OCH; oleic acid (fatty acids); orbencarb; ortho-dichlorobenzene; ortho-sulfamuron; oryzalin; oxabetrinil; oxadiargyl; oxapyrazon; oxasulfuron; oxaziclomefone; oxodiazon; oxyfluorfen; parafluron; paraquat; paraquat dichloride; pebulate; pendimethalin; penoxsulam; penoxsulam; pentachlorophenol; pentachlorophenyl laurate; pentanochlor; pentoxazone; petroleum oils; perfluidone; pethoxamid; phenisopham; phenmedipham; phenmedipham-ethyl; phenobenzuron; phenylmercury acetate; picloram; picloram-potassium; picolinafen; picolinafen; pinoxaden; piperophos; potassium arsenite; potassium azide; potassium cyanate; pretilachlor; primisulfuron; primisulfuron-methyl; procyazine; prodiamine; profluazol; profluralin; profoxydim; proglinazine; prometon; prometryn; propachlor; propanil; propaquizafop; propazine; propham; propisochlor; propoxycarbazone; propyrisulfuron; propyzamide; prosulfalin; prosulfocarb; prosulfuron; pyraflufen-ethyl; proxan; prynachlor; pydanon; pyraclonil; pyraflufen; pyrasulfotole; pyrazolynate; pyrazasulfuron; pyrazosulfuron; pyrazoxyfen; pyrazolynate; pyrazosulfuron-ethyl; pyrazoxyfen; pyribenzoxim; pyributicarb; pyriclor; pyridafol; pyridate; pyriftalid; pyriminobac; pyriminobac-methyl; pyrimisulfan; pyrithiobac; pyrithiobac-sodium; pyroxasulfone; pyroxasulfone; pyroxsulam; pyroxsulam; pyroxsulam; quinclorac; quinmerac; quinoclamine; quinofolamine; quinonamid; quizalofop; quizalofop-ethyl; quizalofop-P; quizalofop-P-ethyl; quizalofop-P-tefuryl; rimsulfuron; rhodethanil; saflufenacil; saflufenacil; sebuthylazine; secbumeton; sethoxydim; siduron; simazine; simeton; simetryn; SMA; S-metolachlor; sodium arsenite; sodium azide; sodium chlorate; sodium chloroacetate; sodium pentachlorophenoxide; sodium-dimethylarsinate; sulcotrione; sulfallate; sulfentrazone; sulfometuron; sulfometuron-methyl; sulfosulfuron; sulfuric acid; sulglycapin; swep; tars; TCA-sodium; tebutam; tebuthiuron; tepraloxydim; tepraluxydim (BAS 620H); terbacil; terbucarb; terbuchlor; terbumeton; terbuthylazine; terbutryn; tetrafluron; thenylchlor; thiazafluron; thiazopyr; thidiazimin; thidiazuron; thidiazuron; thiencarbazone; thifensulfuron; thifensulfuron-methyl; thiobencarb; tiocarbazil; tioclorim; topramezone; topramezone; tralkoxydim; triallate; triasulfuron; triaziflam; tribenuron; tribenuron-methyl; tribenuron-methyl; tricamba; trichloroacetic acid; triclopyr; triclopyr-butotyl; triclopyr-triethylammonium; tridiphane; trietazine; trifloxysulfuron; trifluralin; triflusulfuron; triflusulfuron-methyl; trifop; trifopsime; trihydroxytriazine; trimeturon; tripropindan; tritac; tritosulfuron; 2,4,5-T; 2,4,5-TB; 2,3,6-TBA; TCA; tebutam; tebuthiuron; tefuryltrione; tembotrione; vernolate: YRC 2388; and xylachlor.

The preferred agriculturally active entities are those that are commercially available and require the use of these dendrimers such as to solubilize them or enable fewer applications to be effective or prevent environmental issues. These include, but are not limited to, glyphosate or trifluralin.

The PEHAM dendritic polymers of Formula (I) can be useful as: surface conjugated or surface associated carriers (such as possible from their shape variants of ellipsoids, spheres, rods, random hyperbranched, dendrigrafts, core-shell tecto dendrimers) which can be further modified by the variety of surface groups (TF) present; encapsulated carriers (whether the agriculturally active entity is associated with the interior (IF) or simply entrapped) for use in a time release agriculturally active formulation, having cleavable linkages in the structure of the dendritic polymer for time release and pH or other desired changes once applied, solubility differences between the interior and surface of the dendritic polymer, quantity of agriculturally active entity possible per PEHAM dendritic polymer because of generation or shape; and precision in their size enables use as molecular size standards, calibrating agents, and pore-forming templates for penetration of the plant such as the leaves or seed such as its coating.

The agriculturally active entity is associated with the interior, surface or both the interior and surface of these PEHAM dendrimers and the groups may be the same or different. As used herein, "associated with" means that the agriculturally active entity(s) can be physically encapsulated or entrapped within the interior of the dendrimer, dispersed partially or fully throughout the dendrimer, or attached or linked to the dendrimer or any combination thereof, whereby the attachment or linkage is by means of covalent bonding, hydrogen bonding, adsorption, absorption, metallic bonding, van der Walls forces or ionic bonding, or any combination thereof. The association of the agriculturally active entity(s) and the dendrimer(s) may optionally employ connectors and/or spacers or chelating agents to facilitate the preparation or use of these formulations. Suitable connecting groups are groups which link a targeting director (i.e., T) to the dendrimer (i.e., D) without significantly impairing the effectiveness of the director or the effectiveness of the agriculturally active entity(s) present in the combined dendrimer and agriculturally active entity. These connecting groups may be cleavable or non-cleavable and are typically used in order to avoid steric hindrance between the target director and the dendrimer; preferably the connecting groups are stable (i.e., non-cleavable) unless the site of delivery would have the ability to cleave the linker present (e.g., an acid-cleavable linker for release at the cell surface or in the endosomal compartment). Since the size, shape and functional group density of these dendrimers can be rigorously controlled, there are many ways in which the agriculturally active entity can be associated with the dendrimer. For example, (a) there can be covalent, coulombic, hydrophobic, or chelation type association between the agriculturally active entity(s) and entities, typically functional groups, located at or near the surface of the dendrimer; (b) there can be covalent, coulombic, hydrophobic, or chelation type association between the agriculturally active entity(s) and moieties located within the interior of the dendrimer; (c) the dendrimer can be prepared to have an interior which is predominantly hollow (i.e., solvent filled void space) allowing for physical entrapment of the agriculturally active entity within the interior (void volume), wherein the release of the agriculturally active entity can optionally be controlled by congesting the surface of the dendrimer with diffusion controlling moieties, (d) where the dendrimer has internal functionality groups (IF) present which can also associate with the agriculturally active entity, possesses a cleavable (IF) which may allow for controlled (i.e., pH dependent) exiting from the dendrimer interior or (e) various combinations of the aforementioned phenomena can be employed.

The formulation of this invention comprises at least one PEHAM dendrimer associated with at least one agriculturally active entity. Both of these components can have more than one type present; thus more than one PEHAM dendrimer and more than one agriculturally active entity can be present in a formulation.

The formulation often has at least one agriculturally-acceptable diluent or carrier present. Which agriculturally-acceptable diluent or carrier is used depends on the end use or climatic and/or edaphic conditions. Some of these diluents or carriers are any solid or liquid additives corresponding to the usual formulation techniques which are acceptable for uses for agriculture and can be formulated as liquids, sprays, oils, emulsions, suspensions, granules, powders, dusts, and other customary formulations.

Other customary additives may also be present such as adjuvants, anticaking agents; colorants, thickeners, surfactants, antifoaming compounds, detergents such as alkaline-earth metal salts, dispersants, alkalinizing agents such as bases, bonding agents, emulsifiers, oxidizing agents such as free radical scavengers or catalytic destroyers of hydroperoxides, anticorrosive agents, attractants and/or food substances for the preparation of insecticide baits in particular. These additives may be present in the formulations according to the invention in quantities of between 0 and 75% by weight of said formulations.

Also according to the needs, the nature of the diseases to be treated, of the insect and/or animal pests and/or of the weed plants to be controlled, destroyed or eradicated, the levels of infestation of these pests, the climatic and/or edaphic conditions, the formulations according to this invention may contain one or more agriculturally active entity of the type including fungicides and/or insecticides and/or acaricides and/or rodenticides and/or nematocides and/or insect and/or animal pest repellents and/or agents regulating the development of plants and/or insects and/or one or more herbicide active substances.

This formulation is used in a method for treating plants or seeds with such a formulation as described above, preferably with an adjuvant and/or carrier for ease of application, for improving adhesion of the agriculturally active entity to plant surfaces, improving rain-fastness of the agriculturally active entity to the plant or seed, protection of the agriculturally active entity from UV damage by use of the formulation, protection of the plant or seed from UV damage by use of the formulation, increasing soil penetration of the agriculturally active entity or reducing soil adhesion of the agriculturally active entity such that it can reach the plant roots or under soil parts, or reducing enzymatic degradation of the agriculturally active entity by the plant or seed or microorganisms in the soil. These methods enable reduction in loss of the agriculturally active entity into the environment such as water runoff, lower the amount of application required of the agriculturally active entity agriculturally active entity while maintaining the effectiveness of the agriculturally active entity, and permit better dispersion and reduced viscosity of the formulation so that the agriculturally active entity is more efficiently and effectively use.

While not wishing to be bound by theory, it is believed that PEHAM dendrimers provide the increased solubilization of the agriculturally active entity, and/or reduced viscosity and/or better dispersion by a variety of methods, such as absorbing the UV photons by the dendritic macromolecule to reduce photodegradation of the agriculturally active entity, increase the solubility by encapsulating the less soluble agriculturally active entity where the dendrimer surface is more highly soluble in the desired environment, using surface chemistry of the PEHAM dendrimer it can penetrate the soil, roots, leaves and seeds such as the coating to reach the cells or treat the pests such that rain-run off of the agriculturally active entity is reduced. When the surface groups on the dendrimer are modified as the (TF) or by the agriculturally active entity, the adhesion to the surface of leaves, seeds and other surfaces is provided.

While not wishing to be bound by theory, it is believed that the PEHAM dendrimers of Formula (I) either associate with the agriculturally active entity or act as an excipient that enhances the named properties of the formulation.

Equipment and Methods

Size Exclusion Chromatography (SEC)

A methanolic solution of Sephadex™ (Pharmacia) purified dendrimer was evaporated and reconstituted with the mobile phase used in the SEC experiment (1 mg/mL concentration). All the samples were prepared fresh and used immediately for SEC.

Dendrimers were analyzed qualitatively by the SEC system (Waters 1515) operated in an isocratic mode with refractive index detector (Waters 2400 and Waters 717 Plus Auto Sampler). The analysis was performed at RT on two serially aligned TSK gel columns (Supelco), G3000PW and G2500PW, particle size 10 µm, 30 cm×7.5 mm. The mobile phase of acetate buffer (0.5M) was pumped at a flow rate of 1 mL/min. The elution volume of dendrimer was observed to be 11-16 mL, according to the generation of dendrimer.

High Pressure/Performance Liquid Chromatography (HPLC)

High pressure liquid chromatography (HPLC) was carried out using a Perkin Elmer™ Series 200 apparatus equipped with refractive index and ultraviolet light detectors and a Waters Symmetry® $C_{18}$ (5 µm) column (4.6 mm diameter, 150 mm length). A typical separation protocol was comprised of 0.1% aqueous acetic acid and acetonitrile (75:25% v/v) as the eluant and UV light at λ=480 nm as the detector.

Thin Layer Chromatography (TLC)

Thin Layer Chromatography was used to monitor the progress of chemical reactions. One drop of material, generally 0.05M to 0.4M solution in organic solvent, is added to a silica gel plate and placed into a solvent chamber and allowed to develop for generally 10-15 mins. After the solvent has been eluted, the TLC plate is generally dried and then stained (as described below). Because the silica gel is a polar polymer support, less polar molecules will travel farther up the plate. "$R_f$" value is used to identify how far material has traveled on a TLC plate. Changing solvent conditions will subsequently change the $R_f$ value. This $R_f$ is measured by the ratio of the length the product traveled to the length the solvent traveled.

Materials: TLC plates used were either (1) "Thin Layer Chromatography Plates—Whatman®" PK6F Silica Gel Glass backed, size 20×20 cm, layer thickness: 250 µm or (2) "Thin Layer Chromatography Plate Plastic sheets—EM Science" Alumina backed, Size 20×20 cm, layer thickness 200 µm.

Staining conditions were: (1) Ninhydrin: A solution is made with 1.5 g of ninhydrin, 5 mL of acetic acid, and 500 mL of 95% ethanol. The plate is submerged in the ninhydrin solution, dried and heated with a heat gun until a color change occurs (pink or purple spots indicate the presence of amine). (2) Iodine Chamber: 2-3 g of $I_2$ is placed in a closed container. The TLC plate is placed in the chamber for 15 mins. and product spots will be stained brown. (3) $KMnO_4$ Stain: A solution is prepared with 1.5 g of $KMnO_4$, 10 g of $K_2CO_3$, 2.5 mL of 5% NaOH, and 150 mL of water. The TLC plate is submerged in $KMnO_4$ solution and product spots turn yellow. (4) UV examination: An ultraviolet (UV) lamp is used to illuminate spots of product. Short wave (254 nm) and long wave (365 nm) are both used for product identification.

MALDI-TOF Mass Spectrometry

Mass spectra were obtained on a Bruker Autoflex™ LRF MALDI-TOF mass spectrometer with Pulsed Ion Extraction. Mass ranges below 20 kDa were acquired in the reflector mode using a 19 kV sample voltage and 20 kV reflector voltage. Polyethylene oxide was used for calibration. Higher mass ranges were acquired in the linear mode using a 20 kV sample voltage. The higher mass ranges were calibrated with bovine serum albumin.

Typically, samples were prepared by combining a 1 µL aliquot of a 5 mg/mL solution of the analyte with 10 µL of matrix solution. Unless otherwise noted, the matrix solution was 10 mg/mL of 2,5-dihydroxybenzoic acid in 3:7 acetonitrile:water. Aliquots (2 µL) of the sample/matrix solution were spotted on the target plate and allowed to air dry at RT.

Ultrafiltration Separation (UF)

A typical ultrafiltration separation protocol was as follows: A mixture of product and undesired compounds was dissolved in the appropriate volume of a solvent for this mixture (e.g., 125 mL of MeOH) and ultrafiltered on a tangential flow UF device containing 3K cut-off regenerated cellulose membranes at a pressure of 20 psi (137.9 kPa) at 25° C. The retentate volume as marked in the flask was maintained at 100-125 mL during the UF collection of 1500 mL permeate (~5 hours). The first liter of permeate was stripped of volatiles on a rotary evaporator, followed by high vacuum evacuation to give the purified product. Depending on the specific separation problem, the cut-off size of the membrane (e.g., 3K, 2K or 1K) and the volume of permeate and retentate varied.

Sephadex™ Separation

The product is dissolved in the minimum amount of a solvent (water, PBS, or MeOH) and purified through Sephadex™ LH-20 (Pharmacia) in the solvent. After eluting the void volume of the column, fractions are collected in about 2-20 mL aliquots, depending on the respective separation concerned. TLC, using an appropriate solvent as described before, is used to identify fractions containing similar product mixtures. Similar fractions are combined and solvent evaporated to give solid product.

Nuclear Magnetic Resonance (NMR)—$^1$H and $^{13}$C

Sample Preparation:

To 50-100 mg of a dry sample was added 800-900 µL of a deuterated solvent to dissolve. Typical reference standards are used, i.e., trimethylsilane. Typical solvents are $CDCl_3$, $CD_3OD$, $D_2O$, DMSO-$d_6$, and acetone-$d_6$. The dissolved sample was transferred to an NMR tube to a height of ~5.5 cm in the tube.

Equipment: (1) 300 MHz NMR data were obtained on a 300 MHz 2-channel Varian™ Mercury Plus NMR spectrometer system using an Automation Triple Resonance Broadband (ATB) probe, H/X (where X is tunable from $^{15}$N to $^{31}$P). Data acquisition was obtained on a Sun Blade™ 150 computer with a Solaris™ 9 operating system. The software used was VNMR v6.1C. (2) 500 MHz NMR data were obtained on a 500 MHz 3-channel Varian™ Inova 500 MHz NMR spectrometer system using a Switchable probe, H/X (X is tunable from $^{15}$N to $^{31}$P). Data acquisition was obtained on a Sun Blade™ 150 computer with a Solaris™ 9 operating system. The software used was VNMR v6.1C.

Infrared Spectrometry (IR or FTIR)

Infrared spectral data were obtained on a Nicolet Fourier™ Transform Infrared Spectrometer, Model G Series Omnic, System 20 DXB. Samples were run neat using potassium bromide salt plates (Aldrich).

Ultraviolet/Visible Spectrometry (UV/VIS)

UV-vis spectral data were obtained on a Perkin Elmer™ Lambda 2 UV/VIS Spectrophotometer using a light wavelength with high absorption by the respective sample, for example 480 or 320 nm.

Materials

Trifluralin is commonly used in pre-emergence control of many annual grasses and broad-leaves. It has an aqueous solubility of 0.22 mg/L at pH 7, thus making it difficult to use. For these reasons it serves as a representative test compound in some examples. Using dendrimer technology of this invention, water soluble solutions of trifluralin dendrimers can be prepared, which in turn help in determining the efficacy of trifluralin in soil but also its soil penetration through which a prolonged effect could be achieved. Thus should trifluralin water solubility be increased in this manner, its application to soil through a water based formulation would help by inhibiting germination of selective seeds.

Imidacloprid is a systemic insecticide with translaminar activity with contact and stomach action. Aqueous solubility of Imidacloprid being quite low (0.61 g/L) hinders its use to attack certain pests at required concentrations. An increase in its water solubility with the help of dendrimers could help deliver higher concentrations of Imidacloprid to kill insects.

The invention will be further clarified by a consideration of the following examples, which are intended to be purely exemplary of the present invention.

EXAMPLE 1

Reaction of Pentaerythritol Tetraglycidylether 1 with Tris(2-Aminoethyl)Amine (TREN) 2 to Produce Primary Amine Surface [(C)=PETGE; (IF1)=OH; (BR1)=TREN; (TF)=Primary NH$_2$; G=1]

To a 50-mL round bottom flask containing a stir bar was added TREN 2 (16.0 g, 109 mmol, 10 equiv. per epoxide) and 4 mL of MeOH and cooled to ~25° C. To this stirred mixture was added dropwise a solution of PETGE 1 (1.0 g, 2.78 mmol, 11.1 mmol epoxide) in 2 mL of MeOH. This mixture was stirred for 24 h at 25° C. under a N$_2$ atmosphere. Volatile material was distilled by rotary evaporation to give a crude residue that was bulb-to-bulb distilled using a Kugelrohr apparatus at 200-230° C. at high vacuum to give 2.4 g residue. MALDI-TOF mass spectrum of this material showed a clean spectrum for the desired 4:1 adduct at a mass of 967 amu [M+Na]$^+$ and a smaller signal for the 3:1 adduct at 799 amu [M+Na]$^+$. TLC (50% NH$_4$OH in MeOH) showed the absence of TREN. $^{13}$C NMR spectrum showed the expected peaks for a clean product 3 (2.4 g, 92% yield). Its spectra are as follows:

$^{13}$C NMR: (125 MHz, CDCl$_3$) δ 39.63, 35.36, 47.30, 52.64, 54.01, 57.24, 68.10, 70.33, 74.64; and MALDI-TOF MS: C$_{42}$H$_{101}$N$_{16}$O$_8$; Calc. 944.3. found 967 [M+Na]$^+$ amu.

The following Scheme 1 illustrates this reaction.

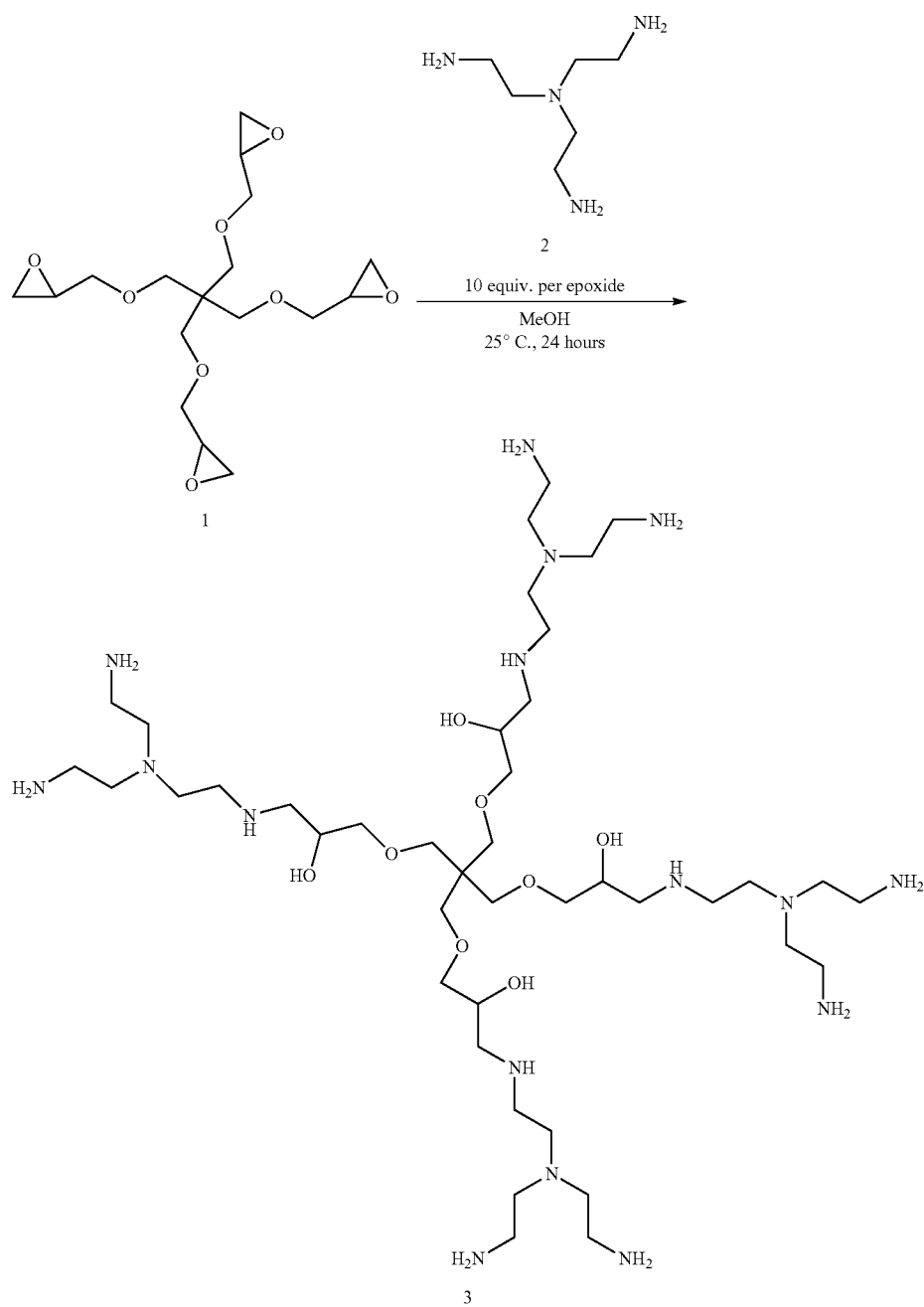

Scheme 1

EXAMPLE 2

Ring-Opening Using a Dihydroxyl Amino Branch Cell Reagent: Hydroxyl Terminated PEHAM Dendrimer (G=1) from Trimethylolpropane Triglycidyl Ether and Diethanolamine [(C)=TMPTGE; (FF)= Et; (IF1)=OH; (BR1)=DEA; (TF)=OH; G=1]

DEA 5 (7.82 g, 74.47 mmol) (Aldrich) and 120 mL of dry MeOH (Aldrich), both without further purification, were placed in an oven dried 250-mL single necked round bottom flask. The flask was equipped with stir bar and septum. TMPTGE 4 (5 g, 16.55 mmol) was dissolved in 40 mL of dry MeOH and added dropwise to the above stirring solution through a pressure equalizing funnel over a period of 1 h at RT. The funnel was replaced with a refluxing condenser and heated at 60° C. for 60 h under a $N_2$ atmosphere. Solvent was removed with a rotary evaporator under reduced pressure to give a colorless transparent liquid. The entire reaction mixture was transferred into a 100-mL single necked round bottom flask. Excess DEA 5 was separated by Kugelrohr distillation under reduced pressure at 180-190° C. The product, 6 (9.76 g; 95.53% yield) was recovered as a transparent viscous liquid. Its spectra are as follows:

$^1$H NMR: (300 MHz, $CD_3OD$): δ 0.87 (t, J=7.50 Hz, 3H, $CH_3$), 1.43 (q, $CH_2$, J=7.20 Hz, 2H), 2.52-2.79 (m, 18H), 3.32 (s, 3H, 3×OH), 3.50 (s, 6H), 3.40 (d, J=5.10 Hz, 6H), 3.54-3.67 (m, 12H), 3.93 (sextet, J=5.10 Hz, 3H), 4.85 (s, 6H, 6×OH); and $^{13}$C NMR: (75 MHz, $CD_3OD$): δ 6.93, 22.76, 43.43, 57.42, 58.51, 59.47, 68.32, 71.56, 73.72; and IR (Neat): $\lambda_{max}$ 3354, 2939, 2817, 1454, 1408, 1367, 1321, 1280, 1111, 1081, 1070, 871, 778 cm$^{-1}$; and MALDI-TOF MS: $C_{27}H_{59}N_3O_{12}$ Calc. 617. found 641 (M$^+$Na) amu.

The following Scheme 2 illustrates this reaction:

EXAMPLE 3

Reaction of Pentaerythritol Tetraglycidylether with Diethyliminodiacetate (DEIDA) [(C)=PETGE; (IF1)=OH; (BR1)=DEIDA; (TF)=Ethyl ester; G=1.5]

To a solution of DEIDA, 7 (5.67 g, 30 mmol) (Aldrich) in 35 mL of EtOH (Aldrich) was added a solution of PETGE, 1 (1.8 g, 5 mmol, 20 epoxy mmol) in 20 mL of EtOH (Aldrich) dropwise over a period of 30 min through an addition funnel. The flask was arranged with a refluxing condenser, $N_2$ gas inlet and placed in a pre-heated oil bath at 60° C. After heating for 1 day, MALDI-TOF MS analysis showed the calculated mass for the perfect structure and the three-substituted products. Heating was continued for 36 h, then the solvent was removed on a rotary evaporator, giving a light brown colored liquid. Excess of DEIDA was distilled off by Kugelrohr distillation apparatus at 175° C. to give a viscous liquid, which was identified as the desired product, 8 (4.99 g, 89.4%). Its spectra are as follows:

$^1$H NMR (300 MHz, $CD_3OD$): δ 1.24-1.29 (24H, t, J=7.20 Hz), 3.03-3.09 (4H, dd, J=3.60 Hz), 2.78-2.85 (4H, bt, J=9.0 Hz), 3.41 (12H, s), 3.45 (8H, s), 3.61 (8H, d, J=5.40 Hz), 4.14-4.21 (16H, q, J=6.60 Hz), 4.61-4.67 (4H, sextet, J=4.20 Hz); and $^{13}$C NMR (75 MHz, $CD_3OD$): δ 13.41, 13.45, 45.89, 49.79, 53.65, 55.77, 56.21, 57.97, 60.57, 60.69, 68.71, 69.79, 69.93, 71.31, 73.55, 78.43, 78.46, 168.62, 170.26, 172.30; and IR (Neat): $\lambda_{max}$ 3457, 2980, 2934, 2904, 2868, 1741, 1675, 1460, 1378, 1250, 1198, 1163, 1106, 1065, 1029, 927, 860, 819, 732 cm$^{-1}$; and MALDI-TOF MS: $C_{49}H_{88}N_4O_{24}$ Calc. 1117.2. found 1117.7 [M]$^+$, 1139.7 [M+Na]$^+$ amu.

The following Scheme 3 illustrates this reaction.

Scheme 2

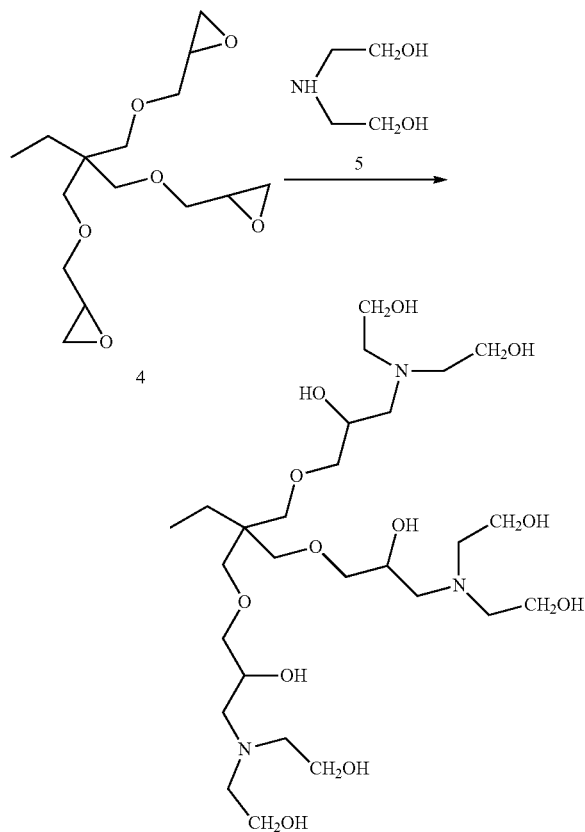

Scheme 3

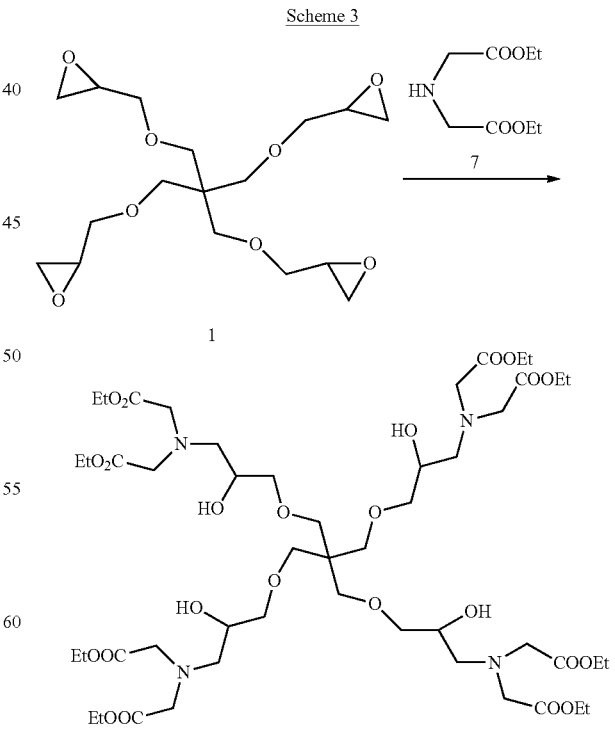

EXAMPLE 4

Ester Derivatives from Primary Amines

A. Synthesis of Pentaerythritol Tetraglycidyl Ether from Pentaerythritol and Epichlorohydrin (EPI) [(C)=PETGE; (TF)=Epoxy]

This process was performed according to Mitsuo et al., Synthesis, 487 (1993). Pentaerythritol 9 (13.6 g, 400 mmol) and 100 mL DMSO were taken in a 1-L 3-necked round bottom flask and then KOH (52.7 g, 800 mmol, 2 equiv. per OH) added all at once. The reaction mixture was stirred vigorously with a mechanical stirrer and cooled to 15-20° C. with an ice bath. EPI 10 (110.4 g or 93.55 mL, 1.2 mol, 3 equiv. per OH) in a pressure-equalizing funnel was added dropwise over a period of 150 min. The temperature was maintained at 15-20° C. during the addition of EPI 10. The color of the reaction mixture turned from colorless to pale yellow. After completing the addition, the reaction mixture was allowed to warm to RT and stirring continued overnight. Progress of the reaction was monitored by TLC. After 3 h, TLC indicated spots for PETGE 1 and pentaerythritol triglycidyl ether 11. By continuing reaction, triglycidyl ether 11 was expected to be converted into product 1; however, some dimerization of 1 was observed, which gave product 12.

Reaction mixture was filtered through a Büchner funnel and solids were washed with 100 mL of DCM. Volatile fractions of DCM were removed on a rotary evaporator. The crude reaction mixture was treated with saturated brine (2×100 mL) and extracted with diethyl ether (2×100 mL). The combined ethereal layers were dried over $Na_2SO_4$ and concentrated on a rotary evaporator to give a dark yellow/light brown liquid. Crude was divided into two equal portions and subjected to column chromatography over silica gel. Silica gel (300 g) was loaded onto column (25 cm height×5.5 cm width). After eluting 500 mL of solvents, fractions were collected in 40 mL. First off fractions were EPI 10 followed by PETGE 1 ($R_f$=0.62), then dimer 12 ($R_f$=0.44), and finally triglycidyl ether 11 ($R_f$=0.33). Isolated pure PETGE 1 yields were 45-60% (some amount will be contaminated with other side products). Spectral analysis was in agreement with reported data for 1 and analysis on products 11 & 12 were also satisfactory.

The following Scheme 4 illustrates this reaction.

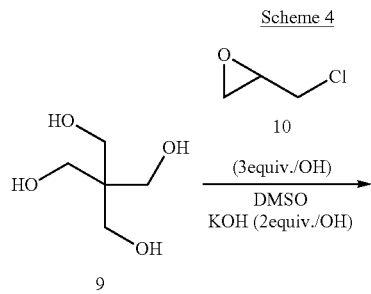

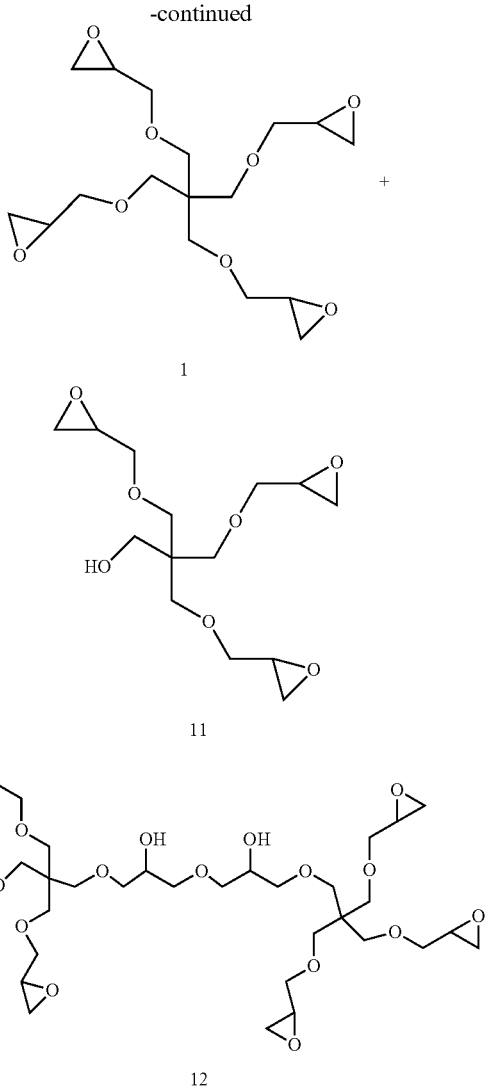

B. Protecting the Primary Amines of Diethylenetriamine and Using to Secondary Amine to Cap the Tetrafunctional Epoxide: Two Primary Amines [(C)=PETGE; (IF1)=OH; (BR1)=DIA; (TF)=Primary $NH_2$; G=1]

DETA 13 (6.56 g, 63.6 mmol) (Acros) and 125 mL of 4-methyl-2-pentanone 14 (Aldrich) were put into a 250-mL round bottom flask, equipped with a Dean-Stark trap, and heated to 140° C. under argon atmosphere. After the theoretical amount of water (2.2 mL) was azeotroped out, the reaction was cooled to RT. The weight of the mixture was 77.37 g, containing 63.6 mmol of secondary amine 15. The mixture (12.16 g) was transferred to a 50-mL round bottom flask. Solvent was removed by rotary evaporation to give an oil. To this oil was added a solution of PETGE 1 (360 mg, 1.0 mmol) (made by Example 4A) in 5.5 mL of dry MeOH. The reaction was heated to 75° C. for 23 h. The solvent was removed to provide 16 and 25 mL of 2-propanol and 3.0 mL of water were added to the residue. The mixture was heated to 50° C. for 2 h. The solvent was removed using a rotary evaporator. Excess DETA 13 was removed by Kugelrohr distillation (150° C.) to give the product 17 as a slightly yellow sticky oil that has the following spectra: MALDI-TOF: Calc. 773. found 795.784 ($M^+Na$) amu.

The following Scheme 5 illustrates this above reaction:
Scheme 5
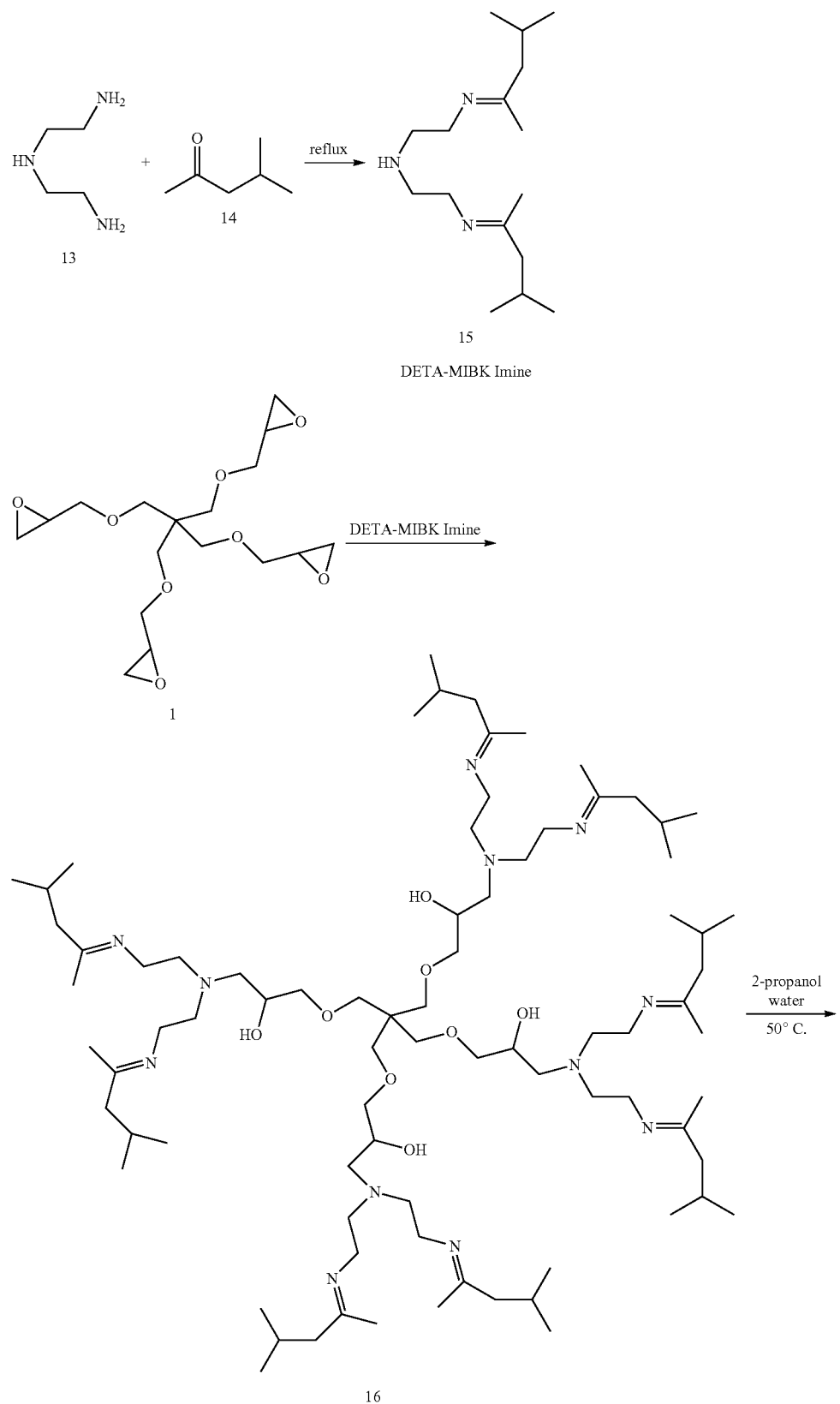

-continued

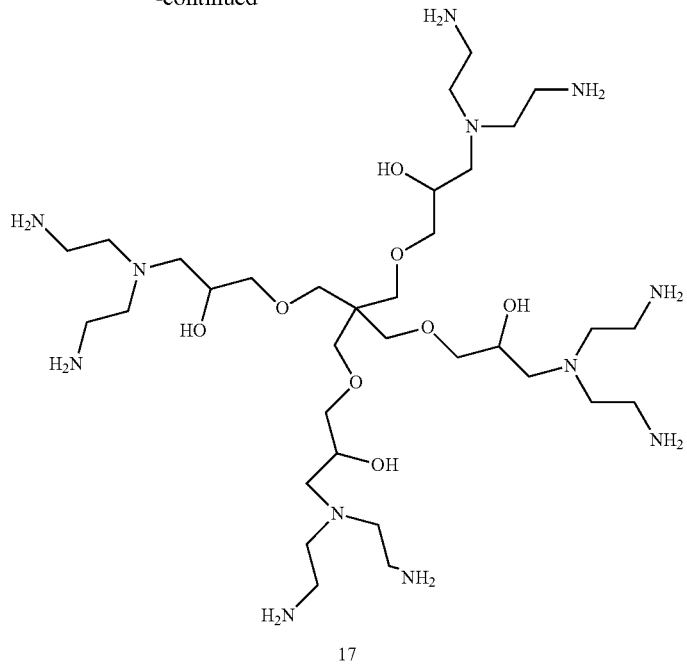

17

C. [(C)=PETGE; (IF1)=OH; (BR1)=DETA; (BR2) In Situ=Methylacrylate; (TF)=Methyl Ester; G=2.5]

A solution of the octa amine 17 (made by Example 4B) in MeOH was added to the solution of methyl acrylate 18 (Acros) in MeOH dropwise at 0° C. (1.5 equiv. per NH).

After the addition, the reaction was allowed to warm to RT. The mixture was then heated to 40° C. for 24 h. Then the solvent was removed to give the product 19 as an yellow oil, having the following spectra: MALDI-TOF: Calc. 2146. found 2169.662 ($M^+Na$) amu.

Scheme 6 illustrates this reaction:

Scheme 6

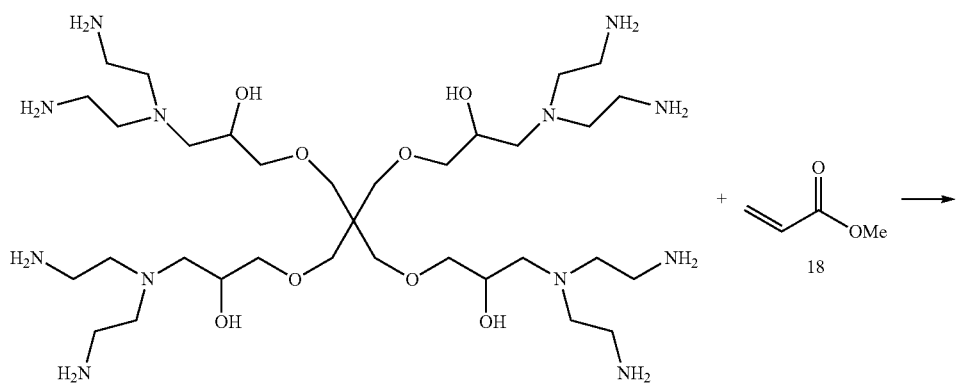

17

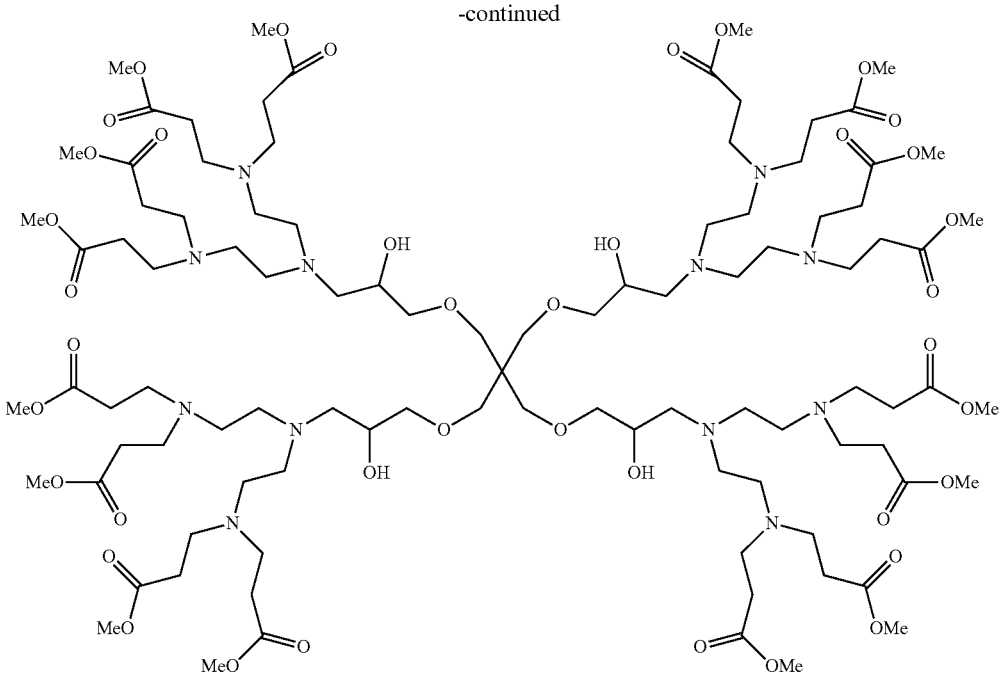

19

EXAMPLE 5

Ring-Opening Using a Preformed Tris(Hydroxymethylamine) (TRIS) Branch Cell Reagent: Nona-Hydroxyl Surface Dendrimer, G=1, from TMPTGE and TRIS [(C)=TMPTGE; (FF)=Et; (IF1)=OH; (BR1)=TRIS; (TF)=OH; G=1]

TMPTGE 4 (2.66 g, 8.8 mmol) and 50 mL of MeOH were placed in an oven dried 100-mL round bottom flask. The flask was equipped with a stir bar and stopper. TRIS 20 (4.79 g, 39.6 mmol) (Fisher Scientific) was added to the above stirring reaction mixture in one portion at RT. The flask was arranged with a refluxing condenser and heated at 60° C. for 60 h under a $N_2$ atmosphere. TRIS 20 dissolves completely after heating for about 15 min The reaction mixture was cooled to RT and transferred into a 500-mL Erlenmeyer flask. Then first 120 mL of chloroform was added, followed by slow addition of 300 mL of hexanes under constant stirring using a spatula. Formation of a white precipitate was observed during the hexanes addition. The mixture was mixed thoroughly once again and allowed to stand at RT overnight. The precipitate was observed as solid flakes on the walls and bottom of the flask. The solution was mixed gently to separate the solid from the glass, followed by filtration of the mixture through a Büchner funnel, giving the desired product 21 (1.7 g). On the bottom of the flask a colorless paste remained, even after separating the solid. This paste weighed 5.2 g ($^1$H and $^{13}$C NMR showed signals for dendrimer 21 along with trace amounts of TRIS 20). The paste was dissolved in 5 mL of MeOH, followed by rinsing the flask with MeOH (2×2 mL). The methanol solution was loaded onto a Sephadex™ LH-20 column. After eluting 600 mL of MeOH, fractions were collected in 15 mL aliquots. The desired dendrimer 21 was found in fractions 18-47; whereas, TRIS 20 was found in fractions 48-58. Fractions 18-47 were combined and the solvent was evaporated on a rotary evaporator under reduced pressure to give a hygroscopic solid (4.2 g; 71.82%), (G=1) PEHAM dendrimer 21. Evaporation of solvents from 48-58 gave TRIS 20 (0.592 g) as a colorless solid. Its spectra are as follows:

$^1$H NMR: (300 MHz, CD$_3$OD): δ 0.86 (t, J=7.20 Hz, 3H), 1.42 (q, J=6.90 Hz, 2H), 2.64 (dd, J=7.80 & 8.10 Hz, 3H), 2.78 (dd, J=3.60 & 3.60 Hz, 3H), 3.34 (s, 6H), 3.35 (s, 6H), 3.41 (d, 5.10 Hz, 6H), 3.48 (s, 1H, OH), 3.50 (s, 1H, OH), 3.53 (d, J=3.00 Hz, 12H), 3.58 (s, 1H, OH), 3.67 (bt, J=3.00 Hz3H, 3×NH), 3.79 (sextet, J=3.60 Hz, 3H), 4.81 (s, 9H, 9×OH); and $^{13}$C NMR: (75 MHz, CD$_3$OD): δ 6.91, 22.72, 43.41, 44.34, 59.83, 61.49, 70.07, 71.57, 74.27; and IR (Neat): $\lambda_{max}$ 3354, 2919, 2873, 1460, 1424, 1408, 1367, 1296, 1234, 1106, 1029, 866, 773 cm$^{-1}$; and MALDI-TOF MS: $C_{27}H_{59}N_3O_{15}$ Calc. 665. found 689 (M$^+$Na) amu.

The following Scheme 7 illustrates this reaction:

Scheme 7

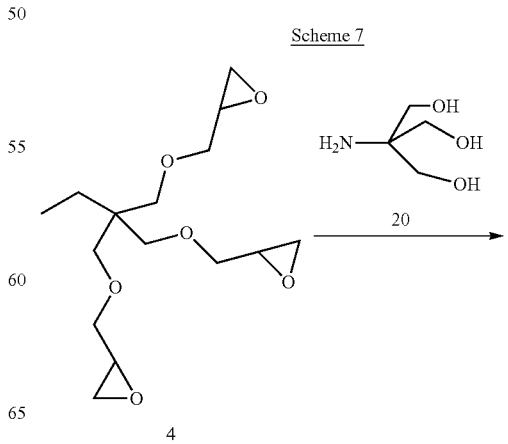

4

-continued

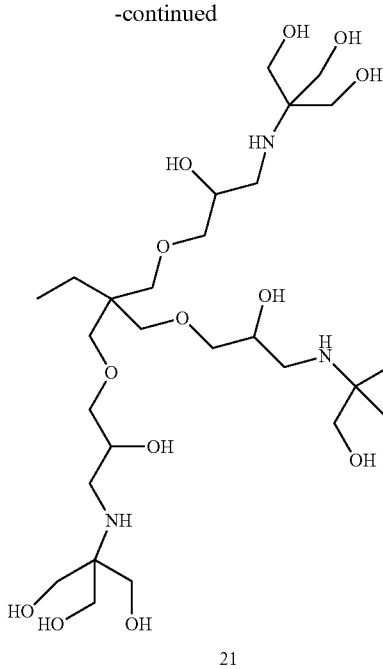

21

EXAMPLE 6

Reaction of Pentaerythritol Tetraglycidylether (PETGE) with Tris(Hydroxymethyl)Aminomethane (TRIS) [(C)=PETGE; (IF1)=OH; (BR1)=TRIS; (TF)=OH; G=1]

In a 250-mL round bottom flask, PETGE 1 (3.16 g, 8.78 mmol) was dissolved into 70 mL of MeOH under mechanical stirring. The solution was placed into a 60° C. oil bath, and TRIS 20 (6.41 g, 52.8 mmol, 1.50 equiv./epoxide) (Fisher Scientific) was added via a powder funnel. The flask was then arranged with a reflux condenser and allowed to react for 48 h. The reaction was monitored by TLC (3:1 $CH_2Cl_2$:MeOH) and no PETGE 1 was observed ($R_f$=0.80) after that time. The mixture was diluted with 120 mL of chloroform, then 300 mL of hexanes were added slowly under stirring. A white precipitate formed and the mixture was allowed to stand for 16 h. The solution was filtered through a Büchner funnel to yield a clear, white paste at the bottom of the flask. The paste was dried under vacuum to yield 6.98 g of crude product 22. The product was re-dissolved into 40 mL of MeOH and 60 mL of chloroform and remaining TRIS 20 was separated by crystallization from 300 mL of hexanes. The mixture was filtered and the remaining semisolid dried under high vacuum for 24 h to yield 5.35 g product 22 (72.0% yield, 7.43 g theoretical mass). For further purification, the material was loaded onto a 36"×4" (91 cm×10 cm) LH-20 Sephadex™ column. After the void volume of 575 mL was collected, 48 fractions each of 12 mL of MeOH were collected and analyzed by TLC (7:3 MeOH:$NH_4OH$). 2.29 g (31% yield) of purified product 22 was recovered. Its spectra are as follows:

$^1H$ NMR (500 MHz, $D_2O$): δ 2.644 (1H, q, J=4.88 Hz), 2.76 (1H, q, J=3.625), 3.34 (2H, s) 3.44 (2H, d, J=9.0 Hz), 3.54 (2H, q, J=6.75 Hz), 3.79 (1H, s), 4.80 (4H, s); and $^{13}C$ NMR (75 MHz, $D_2O$): δ 45.43, 46.91, 49.85, 61.01, 62.69, 71.14, 75.43, 79.42; and MALDI-TOF: $C_{33}H_{72}N4O_{20}$ Calc. 845. found 867 [M+Na]$^+$ amu.

The following Scheme 8 illustrates this reaction.

Scheme 8

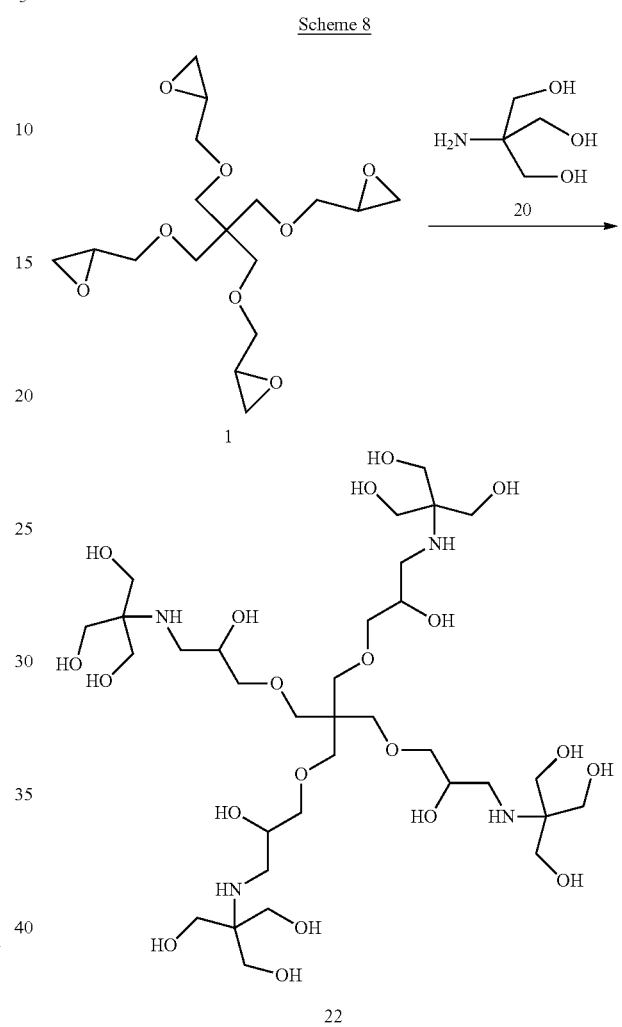

22

EXAMPLE 7

A. Reaction of Pentaerythritol Triallyl Ether (PE-TriAE) with m-Chloroperbenzoic Acid (m-CPBA) [(C)=PETriGE; (FF)=OH; (TF)=Epoxide]

A 100-mL round bottom flask was charged with PETriAE 23 (2.56 g, 10.0 mmol, 30 olefin mmol) (Aldrich) and 50 mL chloroform (Fisher Scientific). To this solution was added under mechanical stirring m-CPBA 24 (8.84 g, 36.0 mmol) (Acros Organics) in portions at RT. The mixture was stirred for 3 days, then first washed with 3% aqueous sodium metabisulfite ($Na_2S_2O_5$) solution (3×100 mL) (Aldrich), followed by 3% aqueous sodium hydrogen carbonate ($NaHCO_3$) solution (3×100 mL). The organic layer was dried over sodium sulfate, concentrated by rotary evaporation to give pale yellow colored liquid 25 (2.58 g, 84.8% yield). Its spectra are as follows:

$^1H$ NMR (300 MHz, $CDCl_3$): δ 2.57 (q, J=2.70 Hz, 3H), 2.76 (t, J=4.50 Hz, 4H), 3.07-3.12 (m, 3H), 3.33 (dd, J=1.50

& 1.20 Hz, 2H), 3.37 (dd, J=1.50 & 1.20 Hz, 2H), 3.51 (q, J=9.00 Hz, 6H), 3.66 (s, H), 3.69 (d, J=2.70 Hz, 2H), 3.73 (d, J=2.40 Hz, 2H); and $^{13}$C NMR (75 MHz, CDCl$_3$): δ 44.34, 45.51, 50.97, 65.33, 71.61, 71.67, 71.73, 72.18, 72.20, 72.23; and IR (Neat): 3507, 3056, 2999, 2922, 2870, 1476, 1450, 1424, 1336, 1248, 1160, 1098, 1051, 953, 901, 855, 834, 751 cm$^{-1}$; and MALDI-TOF MS: C$_{14}$H$_{24}$O$_7$; Calc. 304.3. found 327.05 [M+Na]$^+$ amu.

The following Scheme 9 illustrates this reaction.

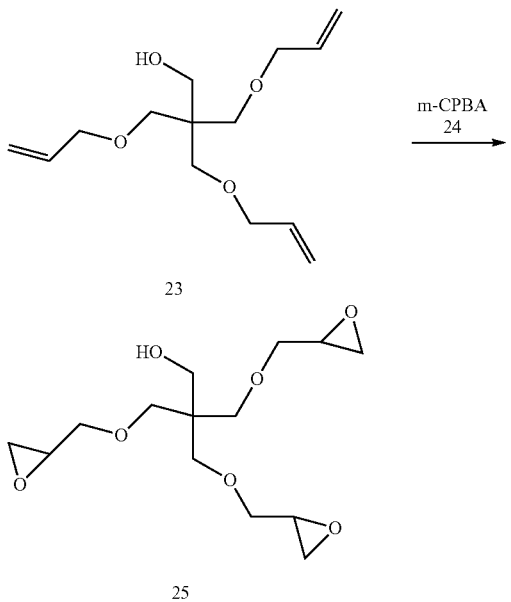

Scheme 9

B. Reaction of Pentaerythritol Triglycidyl Ether (PETriGE) with Propargyl Bromide
[(C)=Pentaerythritol Triglycidyl Ether (PETriGE); (FF)=Alkyne; (TF)=Epoxide]

To a 250-mL oven-dried round bottom flask was added PETriGE product 25 (made by Example 7A) and 120 mL dry DMF (Aldrich). The reaction flask was flushed with N$_2$ gas, closed with a septum and cooled to 0° C. with an ice bath. To this solution was added, under mechanical stirring, sodium hydride (1.35 g, 33.8 mmol, 60% dispersion in mineral oil) (Aldrich) in portions over a period of 20 mins. After additional stirring at 0° C. for 40 mins, propargyl bromide 26 (3.73 mL, 90% wt % in toluene) was added. Cooling continued for 90 mins, and then the mixture was allowed to gradually warm to RT. The mixture was stirred overnight at this temperature. The reaction mixture was then cooled to 10° C. using an ice bath, diluted with 70 mL water, extracted with ethyl acetate (3×70 mL), and washed with saturated brine solution (2×50 mL). The combined extracts were dried over sodium sulfate and concentrated by rotary evaporation to give a dark brown colored liquid, which was purified through column chromatography on silica gel, using initially ethyl acetate in hexanes (20:80% v/v), which was gradually changed to ethyl acetate in hexanes (40:60% v/v). Fractions giving a TLC (ethyl acetate: hexanes 1:1) spot at R$_f$=0.31 were combined and found to be the pure propargylated pentaerythritol triglycidyl ether 27 (3.79 g, 82% yield). Its spectra are as follows:

$^1$H NMR (300 MHz, CDCl$_3$): δ 2.43 (t, J=2.10 Hz, 1H), 2.61 (q, J=2.70 Hz, 3H), 2.79 (t, J=4.20 Hz, 3H), 3.13 (sextet, J=3.00 Hz, 3H), 3.37 (d, J=6.00 Hz, 1H), 3.41 (d, J=5.70 Hz, 1H), 3.51 (d, J=3.90 Hz, 6H), 3.54 (s, 2H), 3.70 (d, J=3.00 Hz, 2H), 3.74 (d, J=2.70 Hz, 2H), 4.13 (dd, J=2.10 & 0.30 Hz, 2H); and $^{13}$C NMR (75 MHz, CDCl$_3$): δ 44.44, 45.69, 51.06, 58.84, 69.05, 70.15, 72.24, 74.34, 80.25; and IR (Neat): 3267, 3057, 2991, 2924, 2878, 2755, 1480, 1434, 1367, 1337, 1260, 1168, 1096, 1014, 963, 906, 840, 758, 666 cm$^{-1}$.

The following Scheme 10 illustrates this reaction.

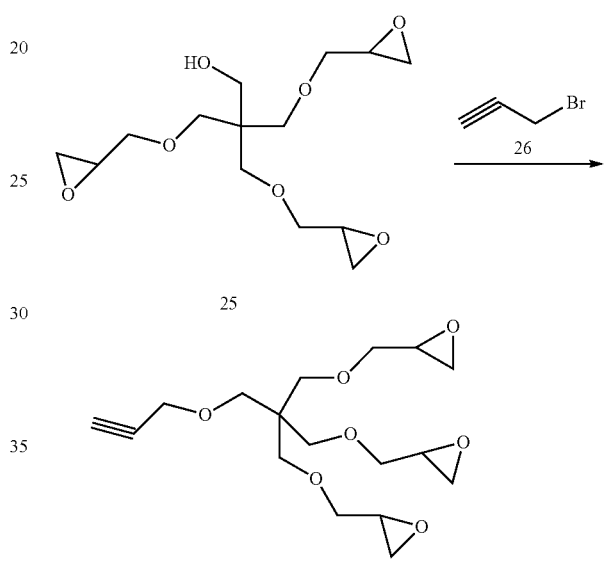

Scheme 10

C: Synthesis of Pentaerythritol Tetraglycidyl Ether from Pentaerythritol Using Allylbromide and m-Chloroperoxy Benzoic Acid (m-CPBA)
[(C)=PETGE; (TF)=Epoxy]

Pentaerythritol 9 (15.03 g, 110 mmol) (Acros Organics) and 250 mL of THF were mixed in a 1-L round bottom flask. KOH (85.93 g 1.35 mol 3.0 equiv. per OH), and tetrabutyl ammonium bromide (TBAB) (0.460 g, 1.23% mol) (Acros Organics) were added via powder funnel, followed by addition of allyl bromide 28 (106.6 g, 1.35 mol, 3.0 equiv. per OH) via a 125-mL addition funnel over 10 mins. The reaction was then immediately placed into an oil bath at 70° C. for 24 hours. The reaction was monitored by TLC (10:1 hexanes:ethyl acetate), showing the product spot at R$_f$=0.4 and no spots for tri-, di-, or mono-allyl-substituted pentaerythritol. The reaction mixture was vacuum-filtered through a 150-mL coarse glass-fritted Büchner funnel. The organic layer was diluted with diethyl ether (2×250 mL). The organic layer was washed with 5% K$_2$CO$_3$ (5×300 mL) and dried over MgSO$_4$. Volatiles were removed by a rotary evaporator (40° C. bath temperature) to yield the pentaerythritol tetraallyl ether 29 (PETAE) (30.07 g; 92% yield); and has the following spectra:

IR (Neat): $v_{max}$ 3080, 2867, 1646, 1478, 1422, 1350, 1264, 1137, 992, 922 cm$^{-1}$; and $^{13}$C NMR: (75 MHz, CDCL$_3$): δ 45.33, 69.25, 72.15, 115.95, 135.16; and $^1$H NMR: (300 MHz, CDCL$_3$): δ 3.39 (4H, s), 3.84 (4H, q, J=2.3 Hz), 5.04 (2H, q, J=13.8 Hz), 5.80 (1H, septuplet, J=7.78 Hz).

PETAE 29 (3.29 g, 11.0 mmol) and 50 mL of chloroform were added to a 500-mL round bottom flask equipped with a magnetic stir bar. Then m-CPBA 24 (70%) (12.51 g, 51.0 mmol, 1.14 equiv. per alkene) (Acros Organics) was added over 10 mins. via an addition funnel. The reaction flask became warm within 30 mins. of the peracid addition. The reaction was stirred for 72 hours at 22° C., then diluted with 100 mL DCM and transferred to a 500-mL separatory funnel. The organic layer was washed with 3% Na$_2$S$_2$O$_5$ (3×150 mL) and 3% NaHCO$_3$ (3×150 mL). The organic layer was dried with Na$_2$SO$_4$, filtered and volatile materials were removed by a rotary evaporator (40° C. bath temperature). TLC (7:3 toluene:acetone) on silica showed one spot at R$_f$=0.48. Further drying of the product overnight at high vacuum yielded PETGE 1 as a clear colorless viscous liquid (3.86 g; 92% yield); and has the following spectra:

IR (Neat): $v_{max}$ 3055, 2997, 2876, 1724, 1480, 1340, 1258, 1163, 1018, 908, 845, 799, 760 cm$^{-1}$; and $^{13}$C NMR (75 MHz, CDCl$_3$): δ 43.96, 45.54 50.62, 69.80, 71.90; and $^1$H NMR: (300 MHz, CDCl$_3$): δ 2.55 (1H, q, J=2.05 Hz), 2.72 (1H, t, J=2.33 Hz), 3.09 (1H, q, J=3.06 Hz) 3.32 (1H, q, J=4.43 Hz), 3.45 (2H, d, J=1.65 Hz), 3.64 (1H, q, J=3.675 Hz); and MALDI-TOF: 383 [M+Na]$^+$ amu.

These reactions are represented in Scheme 11.

Scheme 11

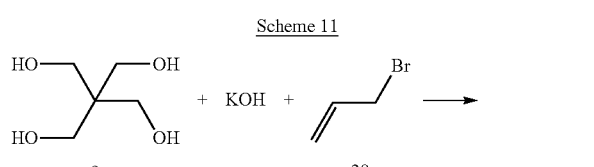

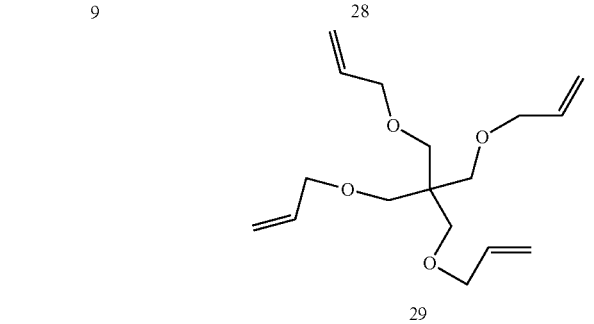

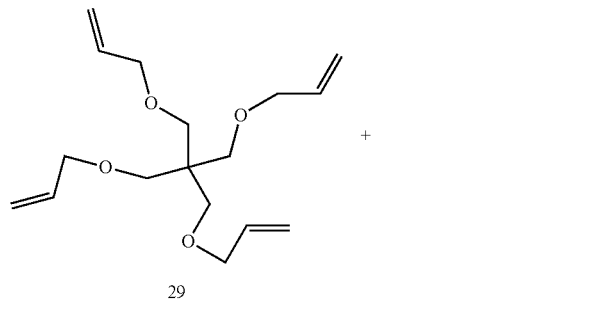

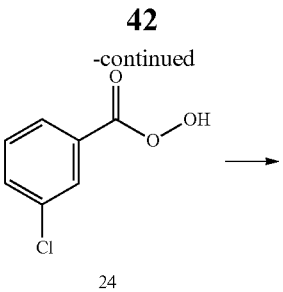

24

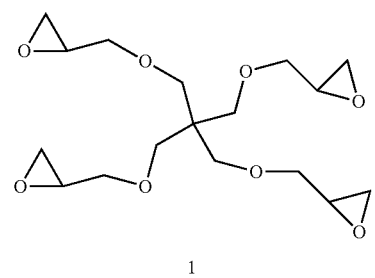

1

D. Reaction of PETGE with Sodium Azide; Modified Core [(C)=Pentaerythritol Tetraazide (PETAZ); (IF)=OH; (TF)=Azide]

A 50-mL round bottom flask was charged with PETGE 1 (3.6 g, 10 mmol) (made by Example 7C), 27 mL DMF and 3 mL water. To this solution was added sodium azide (7.8 g, 120 mmol, 3 equiv. per epoxide), followed by ammonium chloride (6.36 g, 3 equiv.). The reaction flask was equipped with a stir bar and refluxing condenser and heated at 50° C. overnight. Progress of the reaction was monitored by TLC. After this time, the reaction mixture was allowed to cool to RT, then solid materials were filtered off through a Büchner funnel, and the solids were washed with ethyl acetate (1×50 mL). The filtrate was diluted with 70 mL water and extracted with ethyl acetate (3×50 mL). The combined organic layers were washed with saturated brine, dried over sodium sulfate and filtered through a silica gel bed. The filtrate was concentrated by rotary evaporation to give colorless liquid 30 (5.1 g, 95% yield). Its spectra are as follows:

$^1$H NMR (300 MHz, CDCl$_3$): δ 3.04 (bs, 4H, OH), 3.33 (t, J=5.70 Hz, 8H), 3.47 (s, 8H), 3.49 (t, J=2.40 Hz, 8H), 3.93 (pentate, J=5.10 Hz, 4H); and $^{13}$C NMR (75 MHz, CDCl$_3$): δ 45.75, 53.52, 69.68, 71.09, 73.12; and MALDI-TOF MS: $C_{17}H_{32}N_{12}O_8$; Calc. 532.5. found 555.3 [M+Na]$^+$ amu.

The following Scheme 12 illustrates this reaction.

E. Reaction of Propargyl Pentaerythritol Triglycidyl Ether with Pentaerythritol Tetraazide (PETAZ) to Produce PEHAM Dendrimer G=1 with a Four-Arm Core and Epoxide Surface [(C)=PETGE; (IF1)=OH; (EX1)=Triazole; (BR1)=PETriGE; (TF)=Epoxide; G=1]

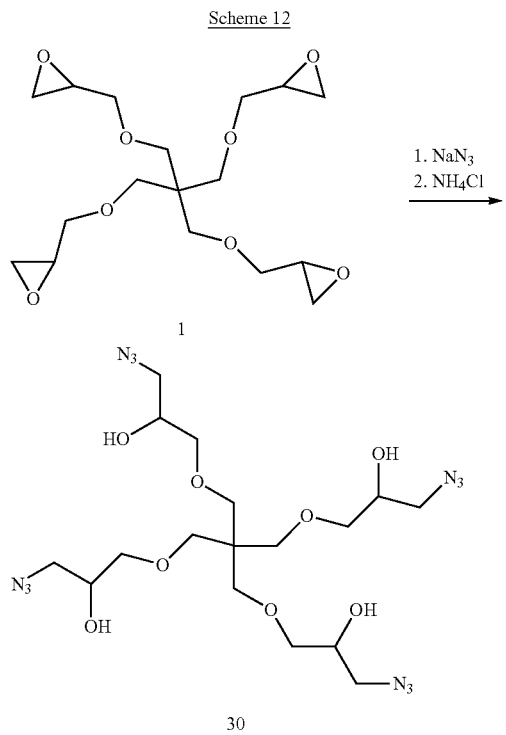

To an oven-dried 50-mL round bottom flask was added propargyl pentaerythritol triglycidyl ether 27 (0.39 g, 1.14 mmol, 1.05 equiv. per $N_3$; made from Example 7B), pentaerythritol tetraazide 30 (0.144 g, 0.271 mmol; made from Example 7D), 1.2 g of t-butanol and 1.2 g of water. The flask was equipped with a stir bar and sealed with a stopper. To this mixture was added sodium ascorbate (0.026 g, 0.114 mmol, 0.10 equiv.), followed by copper(II)sulfate pentahydrate ($CuSO_4 \cdot 5H_2O$) (0.014 g, 0.057 mmol, 0.05 equiv.). The progress of the reaction was monitored by TLC. After stirring for 3 days at RT, the reaction was found to be completed. Product 31 was used for the next reaction in Example 7F without isolation because of the high reactivity of the epoxide groups.

The following Scheme 13 illustrates this reaction.

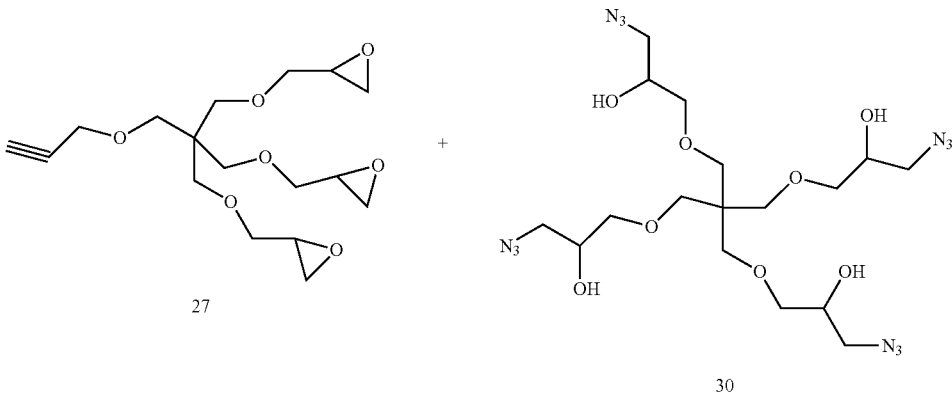

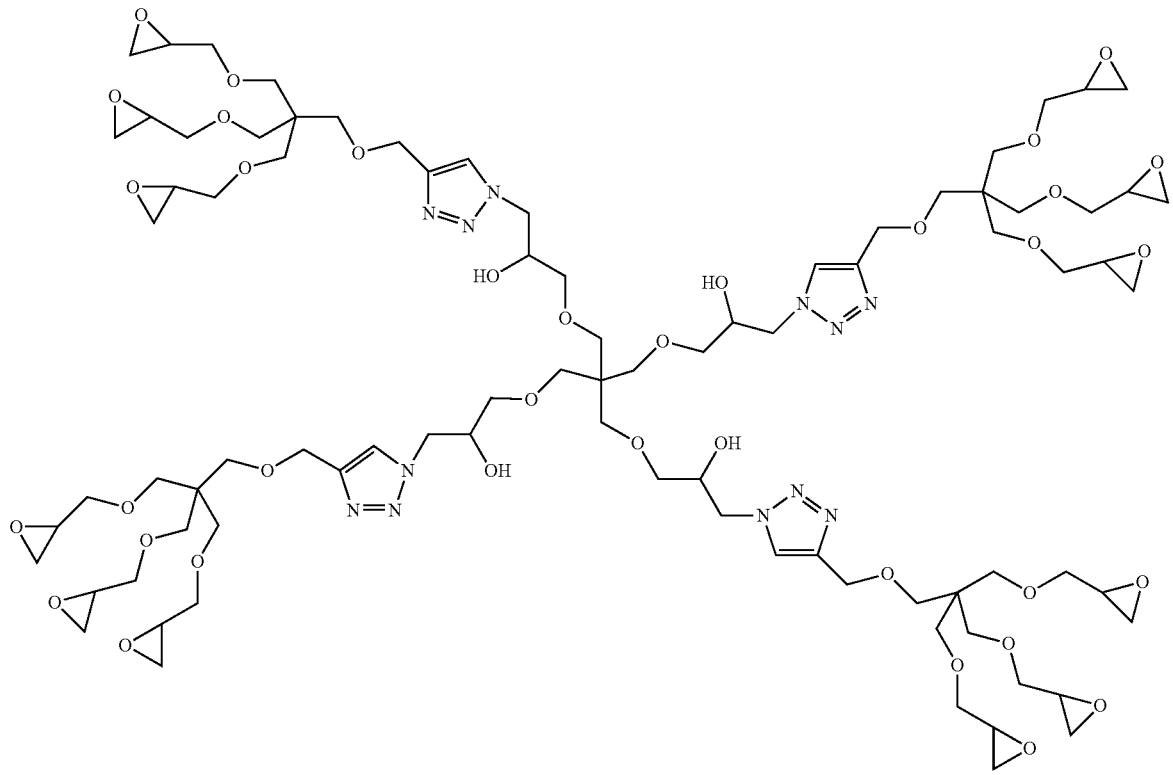

31

F. Reaction of the Product from Example 7E with Diethanolamine (DEA) to Produce PEHAM Dendrimer G=2 with a Four-Arm Core and Hydroxyl Surface [(C)=PETGE; (IF1)=OH; (EX1)=Triazole; (BR1)=PETriGE; (IF2)=OH; (BR2)=DEA; (TF)=OH; G=2]

Crude product 31 was quenched with DEA 5 (1.07 g, 10.26 mmol, 3 equiv. per epoxide) (Aldrich) in 3 mL of t-butanol. The reaction mixture was stirred at RT for 1 day, then heated at 45° C. for 3 days. After cooling to RT, the reaction mixture was diluted with 300 mL of MeOH, and a few undissolved inorganic solids were filtered off. The filtrate was further purified by UF through a 1K size exclusion membrane. After collecting 900 mL of permeate, the retentate was withdrawn from the UF and the UF washed with MeOH (3×50 mL). The solvent was removed by rotary evaporation to give a tan colored liquid, which was dried under high vacuum to give the desired G=2 dendrimer 32 as a foam-like solid (850 mg, 99% yield). Its spectra are as follows:

$^1$H NMR (300 MHz, CD$_3$OD): δ 2.49-2.80 (m, H), 3.40-3.50 (m, H), 3.52-3.70 (m, H), 3.81 (bs, H), 4.10-4.20 (m, H), 4.38-4.50 (m, H), 4.588 (bs, H), 7.99 (s, 4H); and $^{13}$C NMR (75 MHz, CD$_3$OD): δ 29.99, 45.51, 45.68, 53.39, 57.47, 58.46, 59.63, 64.32, 68.44, 69.03, 69.35, 70.12, 72.85, 73.84, 125.04, 144.82.

The following Scheme 14 illustrates this reaction.

Scheme 14

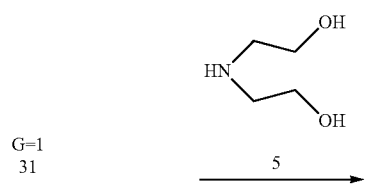

G=1
31
5

-continued

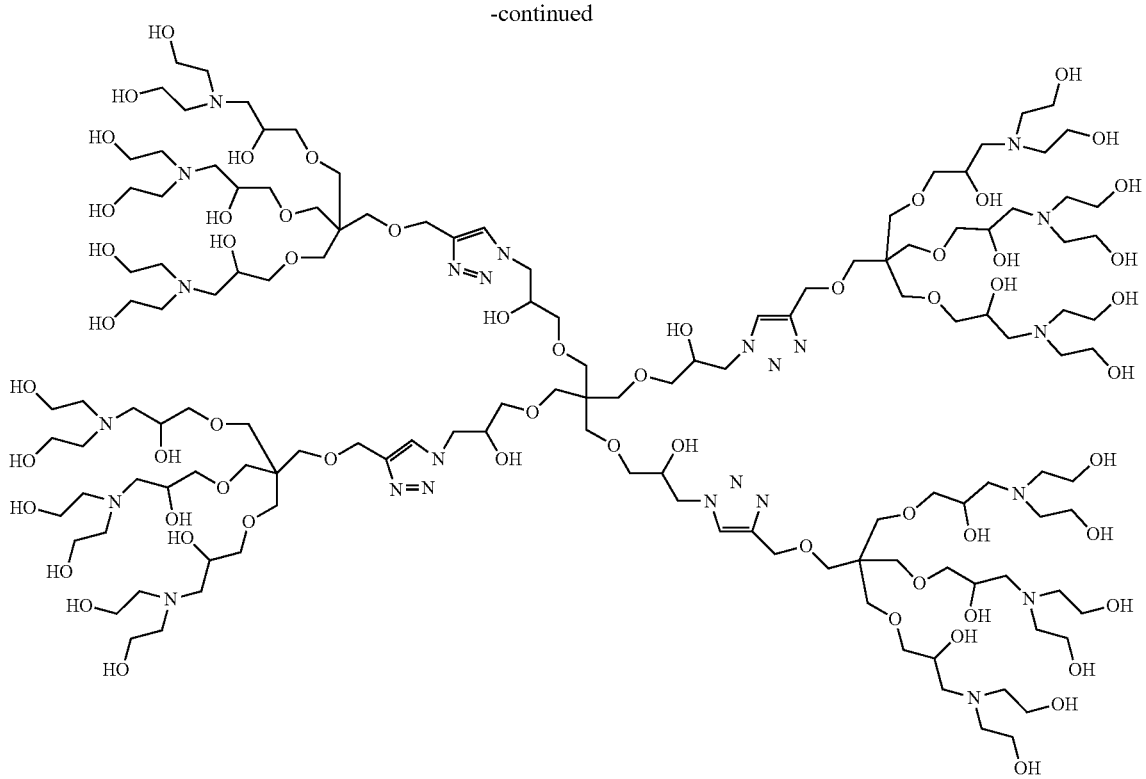

G=2
32

EXAMPLE 8

A. Ring-Opening Using an Diester Amino Branch Cell Reagent Precursor: Ester Terminated PEHAM Dendrimer, G=1, from Trimethylolpropane Triglycidyl Ether (TMPTGE) and Diethyl Iminodiacetate (DEIDA) [(C)=TMPTGE; (FF)=Et; (IF1)=OH; (BR1)=DEIDA; (TF)=Ethyl ester; G=1.5]

DEIDA 7 (14.07 g, 74.47 mmol) (Aldrich) and 120 mL of dry MeOH were placed in an oven dried 250-mL single necked round bottom flask. The flask was equipped with a stir bar and septum. TMPTGE 4 (5.0 g, 16.55 mmol) (Aldrich) was dissolved in 40 mL of dry MeOH and then added to the above stirring solution through a pressure equalizing funnel dropwise over a period of 1 h at RT. The funnel was replaced with refluxing condenser and the flask heated at 60° C. for 60 h under a $N_2$ atmosphere. The solvent was removed on a rotary evaporator under reduced pressure, which gave a colorless transparent liquid. The entire reaction mixture was transferred into a 100-mL single necked round bottom flask. Excess of DEIDA 7 was removed by Kugelrohr distillation under reduced pressure at 150-160° C. Undistilled product 33 (12.59 g; 87.5% yield) was recovered as a pale yellow color, viscous liquid. Compound 33 is stored in ethyl alcohol at 0° C. Its spectra are as follows:

$^1$H NMR: (300 MHz, CD$_3$OD): δ 4.65 (sextet, J=4.20 Hz, 3H), 4.16 (m, 12H), 3.59 (s, 12H), 3.36 (s, 6H), 3.30 (s, 6H), 3.05 (dd, J=3.60 Hz, 3H), 2.95 (dd, J=3.90 Hz, 2H), 2.81 (dt, J=1.80 Hz & 9.90 Hz, 3H), 2.67 (dd, J=8.40 & 8.10 Hz, 2H), 1.37 (q, J=7.50 Hz, 2H), 1.26 (t, J=7.20 Hz, 6H, 2×CH$_3$), 1.25 (J=7.20 Hz, 12H, 6×CH$_3$), 0.85 (t, J=7.50 Hz, 3H, CH$_3$); and $^{13}$C NMR: (75 MHz, CD$_3$OD): δ 6.81, 13.36, 13.40, 22.66, 43.48, 49.85, 53.62, 55.76, 56.21, 58.00, 60.55, 60.68, 68.72, 71.17, 71.33, 71.50, 73.40, 78.43, 78.48, 168.67, 170.25, 172.31; and IR (Neat): $\lambda_{max}$ 2980, 2934, 2904, 2868, 1741, 1460, 1408, 1378, 1342, 1250, 1198, 1111, 1065, 1024, 983, 927, 860, 784 cm$^{-1}$; and MALDI-TOF MS: C$_{39}$H$_{71}$N$_3$O$_{18}$ Calc. 869. found 893 (M+Na) and 847, 801, 779, 775 amu. (The mass spectrum shows a typical fragmentation pattern for elimination of OC$_2$H$_5$ group.)

The following Scheme 15 illustrates this reaction:

Scheme 15

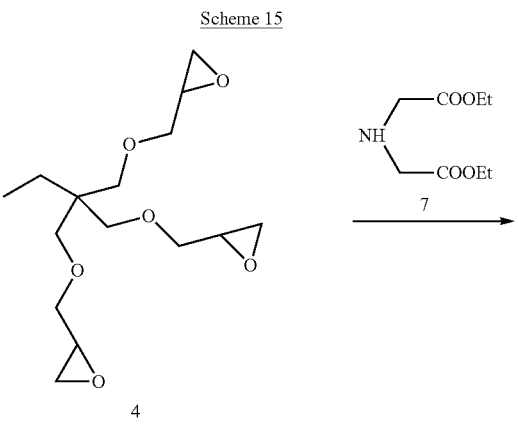

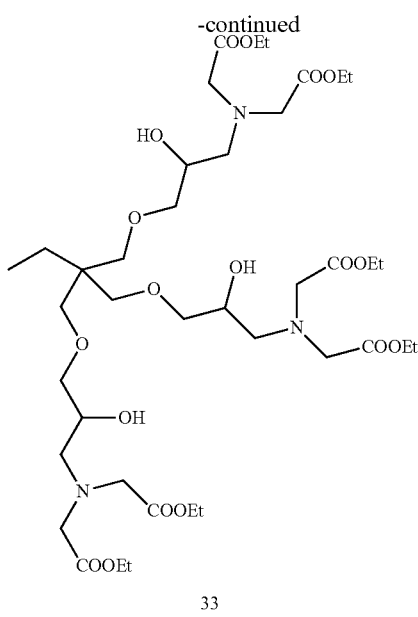

33

B. Reaction of the Product from Trimethylolpropane Triglycidylether Reacting with Diethyliminodiacetate (DEIDA) with Tris(2-Aminoethyl)Amine (TREN) to Produce PEHAM Dendrimer G=2 with a Three-Arm Core and Primary Amine Surface [(C)= TMPTGE; (FF)=Et; (IF1)=OH; (BR1)= DEIDA; (BR2)=TREN; (TF)=Primary NH$_2$; G=2]

A 100-mL round bottom flask was charged with TREN 2 (17.05 g, 116.82 mmol, 60 NH$_2$ equiv. per ester) and 40 mL of MeOH (Fisher Scientific) and a magnetic stir bar. After the exothermic mixing reaction had stopped, (20 min), a solution of G=1 ester 33 (0.846 g, 0.97 mmol, 5.84 ester mmol; made from Example 8A) in 10 mL of MeOH was added dropwise over a period of 1 h at RT. The mixture was then placed in an oil-bath and heated at 50° C. for 3 days. Progress of the reaction was monitored by IR spectroscopy, i.e., the disappearance of the ester vibration at 1740 cm$^{-1}$ and the appearance of the amide vibration at 1567 cm$^{-1}$. MALDI-TOF MS analysis indicated the mass for the desired G=2.0 product 34 accompanied by looped compounds at 1348 [M+Na]$^+$ and 1201 [M+Na]$^+$ (one and two loops). The reaction mixture was diluted with 700 mL of MeOH and subjected to UF using a 1K size exclusion membrane. After collecting 1.8 liters of permeate, the retentate was withdrawn from the UF and the solvent removed by rotary evaporation, giving a pale yellow colored, viscous liquid, which was further dried under high vacuum to give the desired G=2 dendrimer 34 (1.41 g, 98.94% yield). Its spectra are as follows:

$^1$H NMR (300 MHz, CD$_3$OD): δ 0.86 (3H, bt), 1.38 (2H, bs), 2.32-2.60 (H, m), 2.67-2.76 (H, m), 3.29-3.34 (H, m), 3.82 (3H, bs); and $^{13}$C NMR (125 MHz, CD$_3$OD): δ 8.14, 24.06, 38.57, 38.63, 39.98, 40.16, 44.59, 54.00, 55.09, 55.28, 57.21, 58.02, 60.19, 63.05, 63.28, 69.38, 69.94, 72.52, 72.96, 75.00, 173.76, 173.86, 174.03; and IR (Neat): ν$_{max}$ 3298, 2934, 2842, 1659, 1572, 1536, 1470, 1388, 1357, 1311, 1116, 973, 819 cm$^{-1}$; and MALDI-TOF MS: C$_{63}$H$_{143}$N$_{27}$O$_{12}$ Calc. 1470.9843. found 1494.2270 [M+Na]$^+$, 1348.022 [M+Na]$^+$ (one looped), 1201.0970 [M+Na]$^+$ (two looped) amu.

The following Scheme 16 illustrates this reaction.

Scheme 16

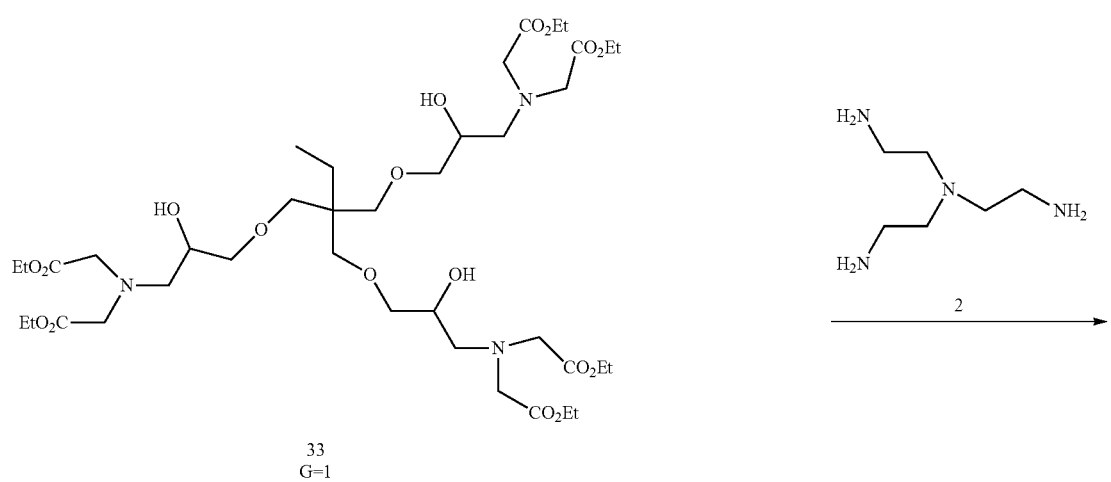

33
G=1

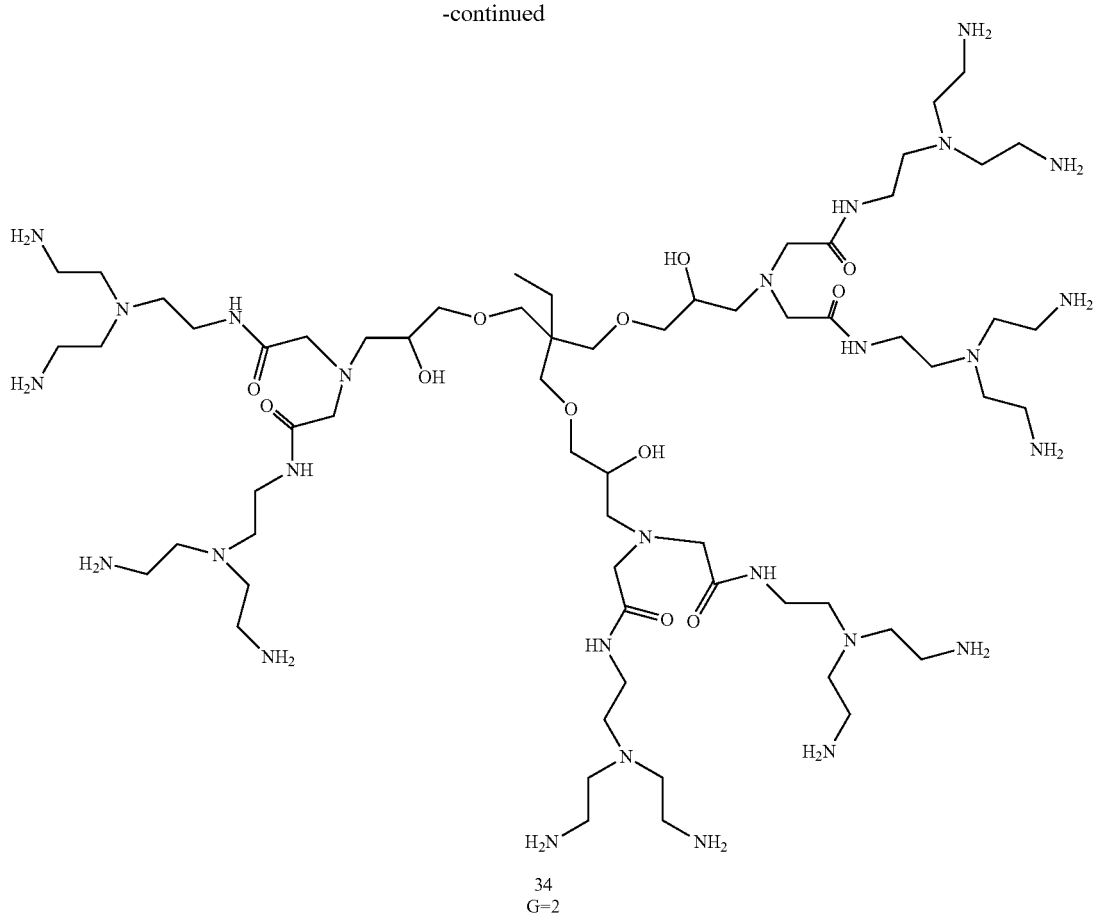

34
G=2

EXAMPLE 9

Reaction of the Product from Pentaerythritol Tetraglycidylether Reacting with Diethyliminodiacetate (DEIDA) with Tris(2-Aminoethyl)Amine (TREN) to Produce PEHAM Dendrimer G=2 with a Four-Arm Core and Primary Amine Surface for DNA Compaction and Antibacterial Activity [(C)= PETGE; (IF1)=OH; (BR1)=DEIDA; (BR2)= TREN; (TF)=Primary NH$_2$; G=2]

A 250-mL round bottom flask was charged with TREN 2 (52.26 g, 358.0 mmol, 120 NH$_2$ equiv. per ester), 50 mL of MeOH (Fisher Scientific) and a stir bar. After the exothermic mixing reaction had stopped (30 min), a solution of G=1 ester 8 (1.25 g, 1.12 mmol, 8.95 ester mmol; made from Example 3) in 10 mL of MeOH was added dropwise over a period of 1 h at RT, and the mixture stirred for overnight. MALDI-TOF MS analysis showed the expected mass peak for the desired product as well as mass peaks for by-products with one and two loops. An IR spectrum was recorded and showed the presence of the amide vibration at 1575 cm$^{-1}$ and the absence of the ester vibration at 1740 cm$^{-1}$. Stirring was continued for additional 36 h. Then the reaction mixture was diluted to 5% w/w solution in MeOH and subjected to UF using a 1K size exclusion membrane. After collecting 3.5 liters of permeate, the retentate was withdrawn from the UF, the solvent was removed by rotary evaporation, and the remaining product dried under high vacuum to give a pale yellow colored, foamy solid 35 (2.02 g, 94% yield). Its spectra are as follows:

$^1$H NMR (500 MHz, CD$_3$OD): δ 2.49-2.59 (H, m), 2.62 (H, bt), 2.66 (H, s), 2.68 (H, s), 2.69 (H, s), 2.70 (H, s), 2.73-2.82 (H, m), 3.29-3.47 (H, m), 3.82 (H, bs); and $^{13}$C NMR (125 MHz, CD$_3$OD): δ 38.64, 40.19, 48.48, 49.85, 53.94, 55.10, 55.29, 57.66, 58.10, 60.23, 63.06, 69.33, 71.41, 75.11, 173.70, 173.80, 173.97; and IR (Neat): ν$_{max}$ 3313, 3078, 2934, 2868, 1649, 1557, 1541, 1475, 1449, 1362, 1306, 1163, 1101, 978, 818 cm$^{-1}$; and MALDI-TOF MS: C$_{81}$H$_{184}$N$_{36}$O$_{16}$; Calc. 1918.6. found 1941.8 [M+Na]$^+$ amu.

The following Scheme 17 illustrates this reaction.
Scheme 17
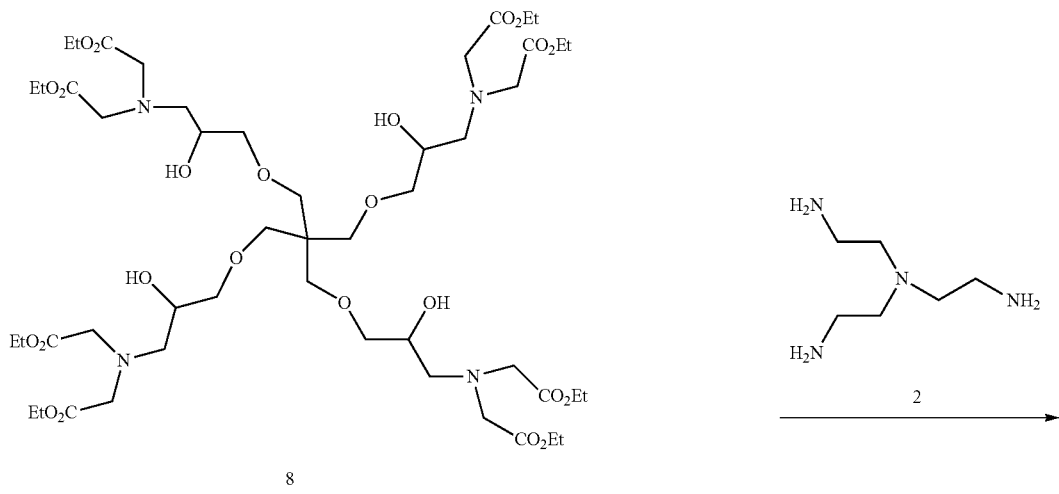
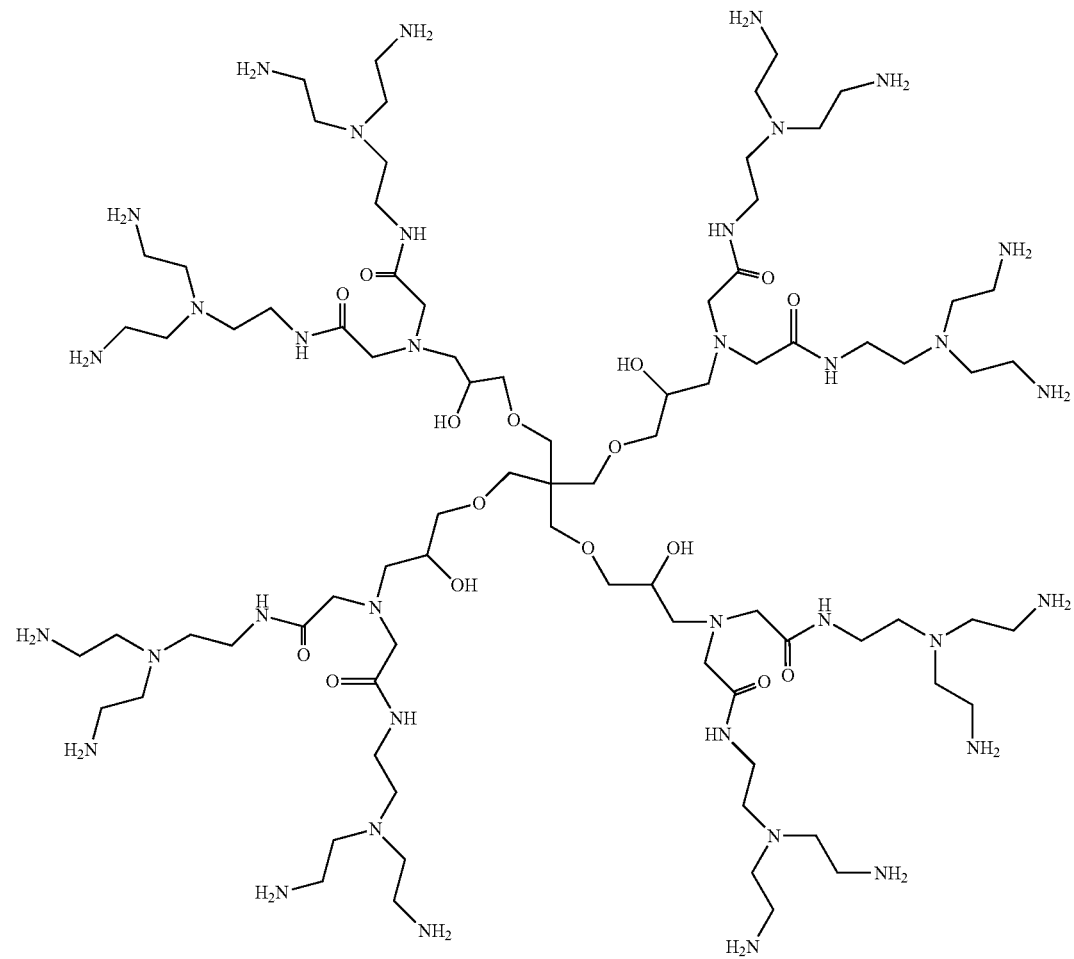
35
G=2

EXAMPLE 10

Reaction of the Product from Trimethylolpropane Glycidyl Ether (TMPTGE) with Iminodiacetic Acid Disodium Salt (IDADS) [(C)=TMPTGE; (FF)=Et; (IF1)=OH; (BR1)=IDA; (TF)=$CO_2Na$; G=1]

Into a 1000 mL, glass, round bottom flask 39 g of NaOH (pellets) was dissolved in 100 mL of $H_2O$. To the stirring solution was added IDADS 36 (91.5 g, 0.69 mol) was added and stirred vigorously until complete dissolution. A solution of TMPTGE 4 (65.77, 0.22 mol) in 100 mL of MeOH was added to the mixture slowly over a period of 20 mins. and rinsed with a further 100 mL of MeOH. The reaction was left to stir for 24 h at 80° C. The reaction is then dried using 40-100 mm Hg at 60° C. until the product becomes a solid and further dried to a constant weight using a high vacuum apparatus to yield a white solid 37 (160 g, 88% yield). Its spectra are as follows:

$^1$H NMR (300 MHz, $D_2O$): δ 0.8 (m, 3H), 1.31 (m, 2H), 3.25-4.1 (br, 30H), 4.2 (m, 3H).

The following Scheme 18 illustrates this reaction.

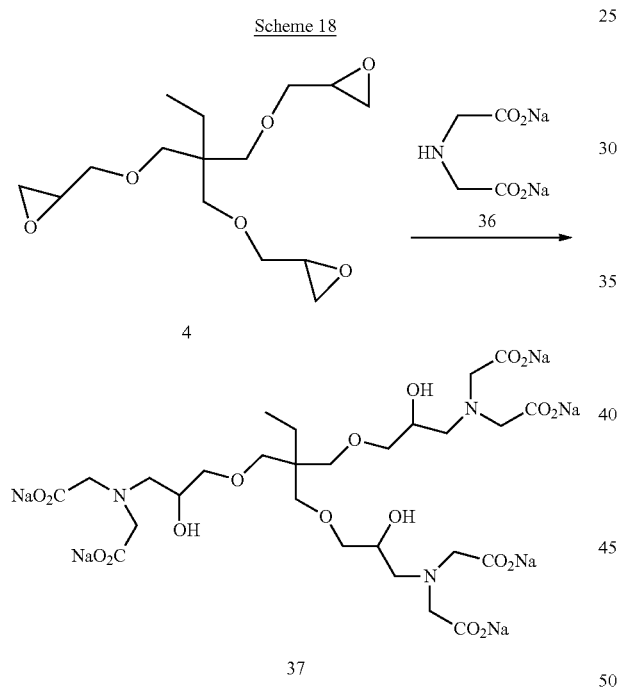

EXAMPLE 11

Reaction of the Product from Trimethylolpropane Glycidyl Ether (TMPTGE) with Iminodiacetic Acid (IDA) [(C)=TMPTGE; (FF)=Et; (IF1)=OH; (BR1)=IDA; (TF)=$CO_2H$; G=1]

To a 100 mL solution of MeOH was added IDA 36 (91.5 g, 0.69 mol) was added and stirred vigorously until complete dissolution. A solution of TMPTGE 4 (65.77, 0.22 mol) in 100 mL of MeOH was added to the mixture slowly over a period of 20 mins. and rinsed with a further 100 mL of MeOH. The reaction was left to stir for 24 h at 80° C. The reaction is then dried using 40-100 mm Hg at 60° C. until the product becomes a solid and further dried to a constant weight using a high vacuum apparatus to yield a white solid 38 (160 g, 88% yield). Its spectra are as follows:

$^1$H NMR (300 MHz, $D_2O$): δ 0.8 (m, 3H), 1.31 (m, 2H), 3.25-4.1 (br, 30H), 4.2 (m, 3H)

The following Scheme 19 illustrates this reaction.

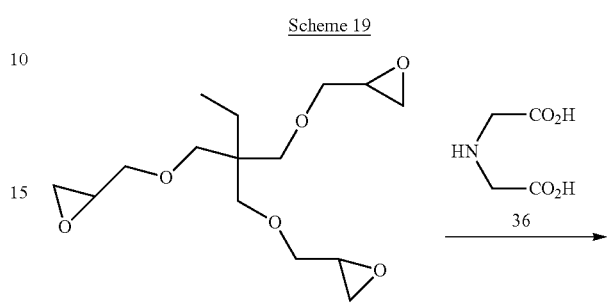

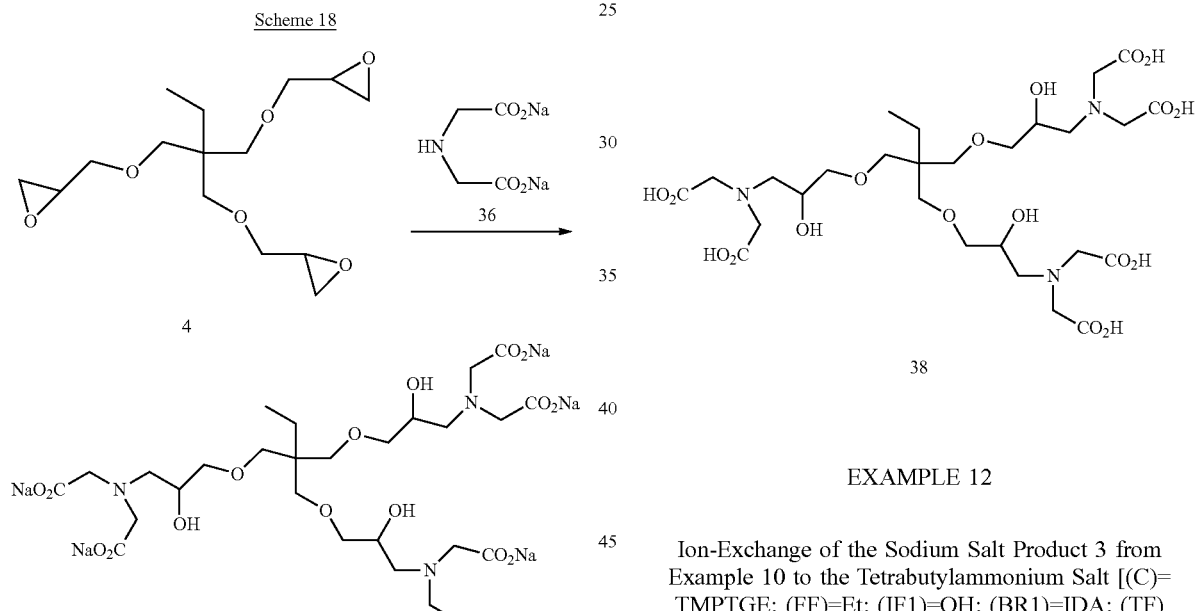

EXAMPLE 12

Ion-Exchange of the Sodium Salt Product 3 from Example 10 to the Tetrabutylammonium Salt [(C)=TMPTGE; (FF)=Et; (IF1)=OH; (BR1)=IDA; (TF)=$CO_2NBu_4$; G=1]

Compound 37 (from Example 10) (2 g, 2.4 mmol) was dissolved in 5 mL of water and passed through an ion-exchange resin (IRC-50) as the H form. The resulting process was repeated four times (2 g of material through an ion-exchange; total mass of 8 g) gave the product 39 with pH of 3. The combined fractions were freeze dried to give a white solid 39 (6.39 g, 84% yield). 2 g of compound 39 were dissolved in water (40 mL) and titrated to pH 8 using approximately 5 mL of the 0.86M tetrabutyl ammonium hydroxide. The titration process was repeated once again with 3.75 g of compound 40. The solutions were combined and freeze dried to yield a white solid 40 (7.95 g). Its spectra are as follows:

$^1$H NMR (300 MHz, $D_2O$): δ 0.7-0.95 (m, 27H), 1.31 (m, 18H), 1.6 (m, 16H), 3.1-3.85 (br, 46H), 4.13 (m, 3H)

The following Scheme 20 illustrates this reaction.

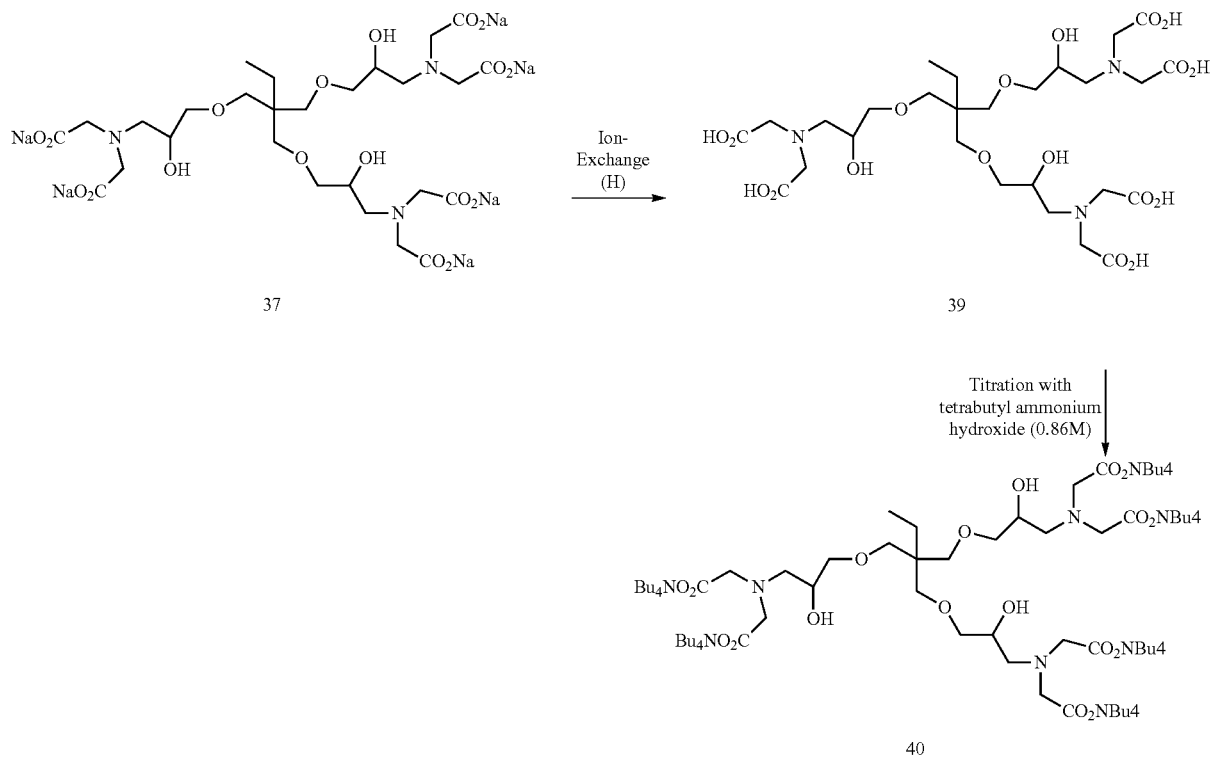

Scheme 20

EXAMPLE 13

Reaction of the Product from Trimethylolpropane Glycidyl Ether (TMPTGE) with Dibenzylamine (DBA) [(C)=TMPTGE; (FF)=Et; (IF1)=OH; (BR1)= DBA; (TF)=Benzyl; G=1]

To a 10 mL solution of MeOH was added dibenzylamine 41 (1.18 g, 6.0 mmol) and stirred. A solution of TMPTGE 4 (500 mg, 1.66 mmol) in 10 mL of MeOH was added to the mixture slowly and left to stir for 24 h at 45° C. The reaction was monitored by LCMS which indicated the reaction had gone to completion. A sample from the reaction mixture was purified by HPLC on a C18 XTerra column, 0.1% TFA with 5-60% ACN gradient. The reaction solvent was removed under reduced pressure and the remaining material 42 was left in its crude form (1.53 g). Its spectra are as follows:

$^1$H NMR (300 MHz, MeOD): δ 0.65 (t, 3H), 1.05 (q, 2H), 2.98 (br s, 6H), 3.05-3.3 (br, 12H), 4.09 (m, 3H), 4.47 (m, 12H), 7.5 (ArH, 30H), and LCMS (hydrophilic): Rf (min) 9.8, (ESI+ve) found 894.31 [M+H]$^+$ calc for $C_{57}H_{72}N_3O_6$.

The following Scheme 21 illustrates this reaction.

Scheme 21

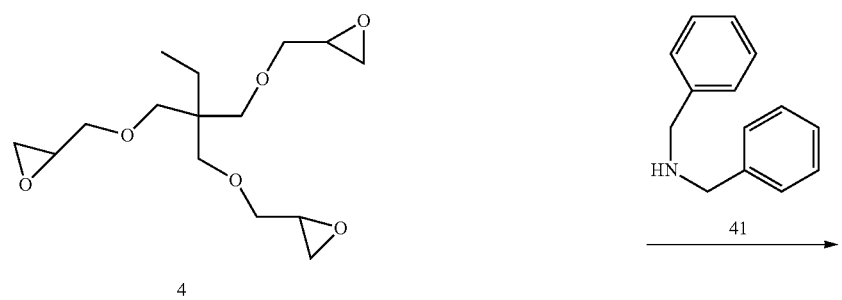

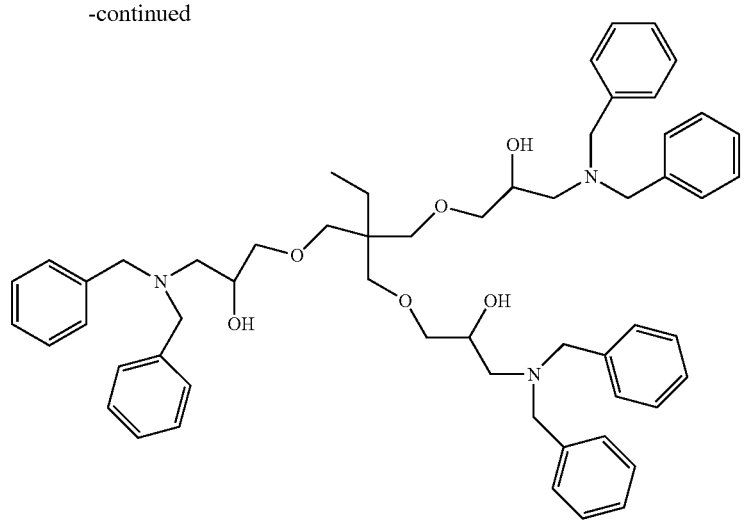

42

EXAMPLE 14

Protecting the Primary Amines of Diethylenetriamine and Using the Secondary Amine to Cap the Trifunctional Epoxide [(C)=TMPTGE; (IF1)=OH; (BR1)=DETA; (TF)=Primary NH$_2$; G=1]

DETA 13 (260.75 g, 2.5 mol) and MIBK 43 (1110 g, 11.1 mol) were put into a 2 L round bottom flask, equipped with a Barrett trap and water-cooled reflux condenser and heated to 110° C. under N$_2$ atmosphere. As the water was azeotroped out, the reaction temperature was increased to 110° C. and distillation was continued until no more water was collecting at the bottom of the Barrett trap. The reaction mixture was cooled to RT under N$_2$. The last traces of MIBK 43 were removed by rotary evaporation to the desired compound 44 as a clear, orange liquid which was continued through to the next step.

The imine protected DETA 44 (806 g, 3 mol) was mixed with isopropanol (100 mL) and left to stir, finally warmed to 60-70° C. under N$_2$. TMPTGE 4 (302, 1 mol) dissolved in isopropanol (200 mL) and added slowly (1.5-2 hours) to the warm DETA-MIBK 44 solution to provide 45. The flask was rinsed with isopropanol (50 mL) and added to the reaction mixture. The reaction mixture was left to stir at 80° C. for 48 h. DI water (300 mL) was added and left to stir for another 16 h at 80° C. The reaction temperature was increased to 110° C. and the water was azeotroped out. This step was reaped twice with 600 mL of DI water. The reaction mixture was cooled to RT and 700 mL of water was added. The solution was extracted with hexane (3×300 mL), which were then discarded. The aqueous solution was filtered through a coarse filter and the solvent removed under reduced pressure. The material was then subjected to a Kugelrohr distillation (205° C. and 5 mm Hg) to yield the product 46 as a viscous, clear, orange, semi solid (498 g, 81.6%). Its spectra are as follows:

$^1$H NMR (300 MHz, MeOD): δ 0.86 (m, 3H), 1.14 (m, 2H), 2.4-2.9 (br, 20H), 3.2-3.75 (br, 16H), 3.85 (br s, 3H); and ESI+ve found 612.16 [M+H]$^+$ calc for $C_{27}H_{66}N_9O_6$.

The following Scheme 22 illustrates this reaction.

Scheme 22

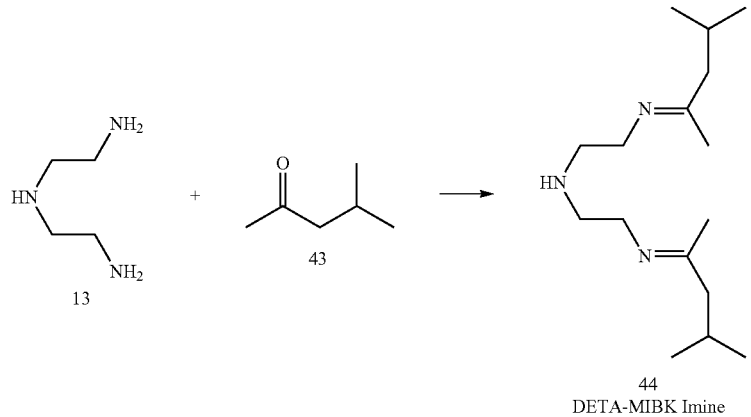

44
DETA-MIBK Imine

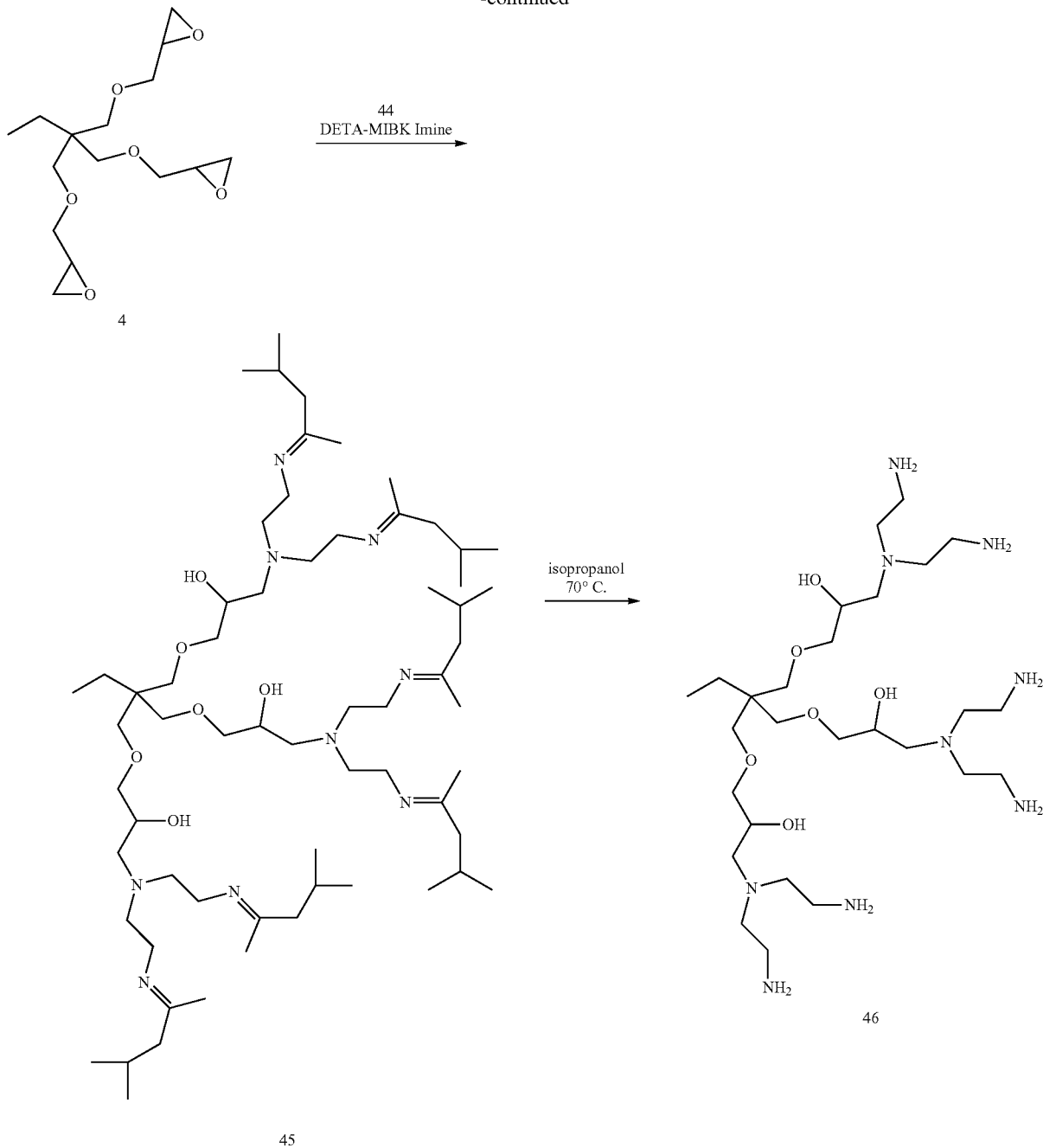

EXAMPLE 15

Ring-Opening Using a Dimethoxy Amino Branch Cell Reagent: Methoxy Terminated PEHAM Dendrimer (G=1) from Trimethylolpropane Triglycidyl Ether and Bis(2-Methoxyethyl)Amine [(C)= TMPTGE; (FF)=Et; (IF1)=OH; (BR1)=DEA; (TF)= OMe; G=1]

Bis(2-methoxyethyl)amine 47 123 g, 119 mmol) (Aldrich) and 800 mL of dry MeOH (Aldrich), both without further purification, were placed in an oven dried 2 L single necked round bottom flask. The flask was equipped with stir bar and septum. TMPTGE 4 (120 g, 39 mmol) was dissolved in 400 mL of dry MeOH and added dropwise to the above stirring solution through a pressure equalizing funnel over a period of 1 h at RT. The funnel was replaced with a refluxing condenser and heated at 60° C. for 60 h under a $N_2$ atmosphere. Solvent was removed with a rotary evaporator under reduced pressure to give a colorless transparent liquid. The entire reaction mixture was transferred into a 1 L single necked round bottom flask. Excess Bis(2-methoxyethyl) amine 47 was separated by Kugelrohr distillation under reduced pressure at 120° C. The product, 48 (230 g; 95% yield) was recovered as a transparent viscous liquid. Its spectra are as follows:

$^1$H NMR: (300 MHz, CD$_3$OD): δ 0.87 (t, J=7.50 Hz, 3H, CH$_3$), 1.43 (q, CH$_2$, J=7.20 Hz, 2H), 2.52-2.79 (m, 18H), 3.32 (s, 3H, 3×OH), 3.50 (s, 6H), 3.40 (d, J=5.10 Hz, 6H), 3.54-3.67 (m, 12H), 3.93 (sextet, J=5.10 Hz, 3H), 4.85 (s, 18H, 6×OMe); and $^{13}$C NMR: (75 MHz, CD$_3$OD): δ 6.93, 22.76, 43.43, 57.42, 58.51, 59.47, 68.32, 71.56, 73.72; and IR (Neat): $\lambda_{max}$ 3354, 2939, 2817, 1454, 1408, 1367, 1321, 1280, 1111, 1081, 1070, 871, 778 cm$^{-1}$; and MALDI-TOF MS: C$_{27}$H$_{59}$N$_3$O$_{12}$ Calc. 701.

The following Scheme 23 illustrates this reaction:

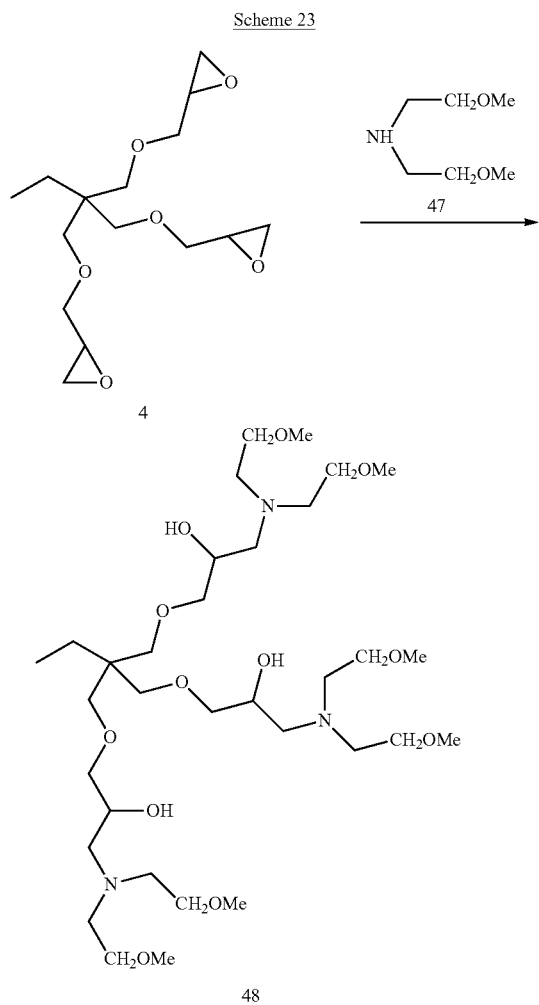

EXAMPLE 16

Formulation of a PEHAM Dendrimer of Formula (I) with an Agriculturally Active Entity where the Solubility of the Active Entity is Increased To a 10% w/w solution of agrochemical active dissolved in a suitable volatile organic solvent, (e.g., MeOH, DCM, EtOH, acetone or other appropriate solvent) was added a 10% w/w solution of dendrimer in either water or the same organic solvent as above. The mixture was left to stir for 2-4 h after which time the volatile organic solvent was then removed under reduced pressure to provide a 1:1 mixture of the active and dendrimer. This oily solution was then dissolved in water and filtered. Analysis of active content in the aqueous solution by HPLC or GC assay provided an estimate of the solubility increase due to the addition of the dendrimer.

Using the general method above for trifluralin (an agrochemical known to have extremely poor aqueous solubility), it was demonstrated that two different dendrimers showed a significant increase in its aqueous solubility. Non-limiting results are shown in Table 1.

TABLE 1

| Active | Solubility assessment by GC assay | Increase in Aqueous Solubility | Sample Appearance |
| --- | --- | --- | --- |
| trifluralin | 0.22 mg/L at pH 7 | Control none | — |
| trifluralin + Example 2 G1 TMPTGE, OH | 0.35 g/L at pH 7 | 1,000 fold | Light yellow, slightly turbid |
| trifluralin + Example 14 G1 TMPTGE, NH$_2$ | 5.43 g/L at pH 7 | 25,000 fold | Clear, yellow solution |

EXAMPLE 17

Formulation of a PEHAM Dendrimer of Formula (I) with an Agriculturally Active Entity where the Solubility of the Active is Increased and Efficacy is Maintained or Increased Concentrated aqueous solutions of trifluralin were made to measure if these solutions retained or increased their herbicide activity. Three different methods were used to prepare three different samples in order to compare the amount of trifluralin retained in aqueous solution and its effect on seed germination.

Preparation of Formulations

Each solution was prepared as follows; 0.1 g of trifluralin was dissolved in 0.9 g of EtOH and 0.1 g of dendrimer of Example 14 was dissolved in 0.9 g of EtOH. These solutions were mixed and left to stir for 4 h resulting in 2 g of 10% w/w of dendrimer and 10% w/w of trifluralin complex. These solutions were then treated using one of the following three methods.

Sample 1:

The 2 g of solution of 10% w/w of dendrimer and 10% w/w of trifluralin complex (prepared above) was subjected to rotary evaporation to remove the EtOH. Pale yellowish crystals started to form in the round bottom flask. The resulting yellow mixture containing the 1:1 trifluralin and dendrimer complex was suspended in water and a few drops of EtOH were added. Undissolved trifluralin was removed by vacuum filtration, which resulted in a bright yellow solution, which theoretically contained 95 mg of trifluralin. The actual concentration of the trifluralin was determined by GC using the AOAC-CIPAC method 1975, Trifluralin Technical183/TC/M/.

Sample 2:

A 2 g sample of 10% w/w of dendrimer of Example 14 and 10% w/w of trifluralin complex (prepared above) was diluted with approximately 38 mL of water. Most of the EtOH was removed on a rotary evaporator, resulting in a 1:1 trifluralin and dendrimer complex in approximately 32 mL of water. Some needle like crystals were observed in the sample and, after vacuum filtration, resulted in a slightly cloudy, yellow filtrate, which theoretically contained 95 mg of trifluralin. The actual concentration of the trifluralin was determined by GC using the AOAC-CIPAC method 1975, Trifluralin Technical183/TC/M/.

Sample 3:

A 2 g sample of 10% w/w of dendrimer of Example 14 and 10% w/w of trifluralin complex (prepared above) was taken and the EtOH was removed by evaporation on a rotary evaporator. The resulting 1:1 trifluralin and dendrimer complex was suspended in approximately 40 mL of water. Filtration of sample resulted in a bright yellow filtrate, which theoretically contained 95 mg of trifluralin. The actual concentration of the trifluralin was determined by GC using the AOAC-CIPAC method 1975, Trifluralin Technical183/TC/M/.

Commercial EC: A positive control of trifluralin was prepared using 0.209 g of 480 g/L of commercial emulsified concentrate of trifluralin in approximately 40 mL of water. This sample contained 89 mg of trifluralin. This sample is an emulsified concentrate (EC) and so it is not really dissolved in aqueous solutions like the dendrimer samples above. This sample was included as a positive control for efficacy determination.

Water: water was used as a negative control.

TABLE 2

Quantities of trifluralin from the samples prepared above

| Sample | Theoretical amount of trifluralin in sample (mg) | Actual trifluralin concentration determined by GC (ppm) | Increase in aqueous solubility of trifluralin* Fold increase |
|---|---|---|---|
| Sample 1 | 95 | 1 | 5x |
| Sample 2 | 95 | 25 | 114x |
| Sample 3 | 95 | 3 | 14x |
| Commercial EC | 89 | N/D | N/A |
| water | 0 | 0 | N/A |

*aqueous solubility of trifluralin is 0.22 mg/L at pH 7

Testing Efficacy of Formulations

From the sample above the entire solution was added to potting mix with equal number of annual rye grass seeds sown. The potting mix was spread onto trays and left for a week to germinate. Assessment after this time showed the following results:

TABLE 3

Efficacy of trifluralin formulations.

| Sample | Concentration of Trifluralin (ppm) | No. of seeds sown | No. of seeds germinated |
|---|---|---|---|
| Sample 1 | 1 | 50 | 15 |
| Sample 2 | 25 | 50 | 0 |
| Sample 3 | 3 | 50 | 5 |
| Commercial EC | 2225 (Theoretically) | 50 | 0 |
| water | 0 | 50 | 20 |

These results indicate that the dendrimer has provided a significant increase in the aqueous solubility of the trifluralin sample (up to 114 fold for sample 2). It can be proposed that due to the presence of EtOH in sample 2, a greater amount of trifluralin has been retained in this sample in comparison to samples 1 and 3. This results in higher levels of inhibiting seed germination. Analysis of sample 2 was found to contain 25 ppm of trifluralin (<6 μg of trifluralin) in the seed germination trial. The low amount of trifluralin in Sample 2 was still efficacious providing strong evidence that not only does the dendrimer increase the aqueous solubility of the trifluralin, it has also provided a significant increase in the efficacy resulting in a surprisingly low level of trifluralin/dendrimer required to obtain high levels of control.

EXAMPLE 18

Formulation of a PEHAM Dendrimer of Formula (I) with an Agriculturally Active Entity where the Solubility of the Active is Increased and Efficacy is Maintained or Increased This experiment assessed water solubility of Imidacloprid in conjunction with dendrimers and observed the bio-efficacy of Imidacloprid-dendrimer mixtures on cockroaches compared to Imidacloprid alone.

Preparation of Formulations

Standard aqueous solutions were prepared by adding Imidacloprid to aqueous solutions of dendrimer of Example 2 whereby the final concentrations are shown in the table below.

TABLE 4

| Sample No. | Concentration of Imidacloprid solutions (g/L) | Imidacloprid and dendrimer ratio | Appearance |
|---|---|---|---|
| 1 | 0.5 | 1:1 | Clear solution |
| 2 | 0.25 | 1:1 | Clear solution |
| 3 | 0.1 | 1:1 | Clear solution |
| 4 | 0.5 | 1:0.5 | Clear solution |
| 5 | 0.25 | 1:0.5 | Clear solution |
| 6 | 0.1 | 1:0.5 | Clear solution |
| 7 | 0.5 | 1:0 | Clear solution |
| 8 | 0.25 | 1:0 | Clear solution |
| 9 | 0.1 | 1:0 | Clear solution |
| 10 | 5.0 | 1:1 | White suspension |
| 11 | 5.0 | 1:0 | White unsuspended particles |
| 12 | 21.5 | 1:1 | White suspension |
| 13 | 21.5 | 1:0 | White unsuspended particles |
| 14 | 40 | 1:1 | White concentrated suspension |
| 15 | 0 | 0:1 | Clear solution |
| 16 | Control | | |

The aqueous solubility of Imidacloprid is quite low and as a result it is difficult keep the active in solution. Use of dendrimer at 1:1 ratio with Imidacloprid has sufficed this problem enabling the formation of stable homogeneous suspensions or dispersions of the active at significantly higher levels.

Testing Efficacy of Formulations

Filter papers of 10 cm were saturated with 3 mL of the above samples which were added to a Petri dish. Care was taken to ensure that the filter paper was not too wet as that would hinder cockroach movement. To each Petri dish was added ten to twelve small cockroaches of a similar age and the effect after 24 h was assessed. These trials were carried out in duplicates along with water control (sample 17) and a dendrimer control (sample 16).

TABLE 5

Cockroaches at 0.5, 0.25, 0.1, 5.0, 21.5, 25, 40 g/L Imidacloprid concentration

| Sample No. | Imidacloprid: Dendrimer | Imidacloprid Conc. (g/L) | Observations after 24 hours |
|---|---|---|---|
| 1a | 1:1 | 0.5 | 9 alive and moving, 1 alive but immobile |
| 1b | 1:1 | 0.5 | 9 alive and moving, 1 alive but immobile |
| 2a | 1:1 | 0.25 | 7 alive and moving, 3 alive but immobile |
| 2b | 1:1 | 0.25 | 5 alive and moving, 5 alive but immobile |
| 3a | 1:1 | 0.1 | 9 alive and moving, 1 squashed |
| 3b | 1:1 | 0.1 | 6 alive and moving, 4 alive but immobile |
| 4a | 1:0.5 | 0.5 | 10 alive and moving, 1 alive but immobile |
| 4b | 1:0.5 | 0.5 | 10 alive and moving, 1 alive but immobile |
| 5a | 1:0.5 | 0.25 | 10 alive and moving, 1 squashed |
| 5b | 1:0.5 | 0.25 | 8 alive and moving, 2 alive but immobile, 1 squashed |
| 6a | 1:0.5 | 0.1 | 8 alive and moving, 3 alive but immobile |
| 6b | 1:0.5 | 0.1 | 7 alive and moving, 2 alive but immobile, 1 squashed |
| 7a | 1:0 | 0.5 | 5 alive and moving, 1 dead, 1 squashed, 3 alive but immobile |
| 7b | 1:0 | 0.5 | 6 alive and moving, 1 squashed, 3 alive but immobile |
| 8a | 1:0 | 0.25 | 9 alive and moving, 1 alive but immobile |
| 8b | 1:0 | 0.25 | 9 alive and moving, 1 alive but immobile |
| 9a | 1:0 | 0.1 | 9 alive and moving, 1 alive but immobile |
| 9b | 1:0 | 0.1 | 8 alive and moving, 2 alive but immobile |
| 10a | 1:1 | 5.0 | 9 dead, 1 alive but immobile |
| 10b | 1:1 | 5.0 | 1 actively moving, 1 alive but immobile, 9 dead |
| 11a | 1:0 | 5.0 | All dead |
| 11b | 1:0 | 5.0 | 3 alive but immobile, 7 dead |
| 12a | 1:1 | 21.5 | All dead |
| 12b | 1:1 | 21.5 | All dead |
| 13a | 1:0 | 21.5 | All dead |
| 13b | 1:0 | 21.5 | All dead |
| 14a | 1:1 | 40 | N/D |
| 14b | 1:1 | 40 | N/D |
| 15 | Dendrimer Control | 0 | All alive |
| 16a | Control | 0 | 8 alive and moving, 1 dead, 1 squashed |
| 16b | Control | 0 | 9 alive and moving, 1 dead |
| 16c | Control | 0 | 10 alive |
| 16d | Control | 0 | 9 alive, 1 dead |

These tests confirmed that the dendrimer itself (sample 16) does not contribute to toxicity of the cockroaches. At a sublethal dose (samples 1-9, below 5 g/L) all cockroaches survived; however, some were a little less active when compared to the cockroaches in the water control region (sample 17). This result suggests that at these concentrations the dendrimer is not of any help in improving toxicity of Imidacloprid to cockroaches. However, at 5 g/L and above of Imidacloprid (samples 10-13), use of the dendrimer enables stable suspension of the active to be achieve and each of these samples show high levels of efficacy.

However, the use of dendrimer enables significantly high levels of Imidacloprid to be dispersed in aqueous solution. While the dendrimer provides no increase in efficacy itself, it does allow significantly higher levels of Imidacloprid to be formulated in aqueous solutions which in turn enables higher levels of activity than otherwise achievable.

EXAMPLE 19

Formulation of a PEHAM Dendrimer of Formula (I) with an Agriculturally Active Entity where the Solubility of the Active Entity is Increased To a 10% w/w solution of agrochemical active dissolved in suitable volatile water miscible organic solvent, e.g. MeOH, EtOH, acetonitrile or acetone is added a 10% w/w solution of a PEHAM dendrimer in water. The mixture is left to stir for 2-4 h. After this time the level of aqueous solution is adjusted to ensure the volatile organic component is less than 10% of the total volume. The sample is frozen in a dry ice acetone bath and the solvent removed by lyophilization to yield an amorphous solid. The amorphous solid is dissolved in water and filtered to yield the stock solution. Analysis of active content in the aqueous solution by HPLC or GC assay provides an estimate of the solubility increase due to the addition of the dendrimer. The PEHAM dendrimer of Examples 2 and 14 were tested and obtained results similar to those of Example 16.

EXAMPLE 20

Improvement in Leaf Penetration and Efficacy of Agriculturally Active Glyphosate in the Presence of PEHAM Dendrimers Sample Preparation:

A matrix of 5 mL standard solutions was prepared using either one of two commercial products—GrowChoice® (based on the glyphosate IPA-salt) and Touchdown® (based on the potassium salt), each at a typical field-use rate of 10 mL/L or 5 mL/L (1% or 0.5%), as well as a total of five PEHAM dendrimers, each prepared to give a final concentration of 0.05% or 0.1% (these are typical concentrations for adjuvants that might be included in the tank-mix). Two control solutions of the same rate of GrowChoice® and Touchdown®, without any dendrimer solution, were also prepared.

TABLE 6

| | Sample Number (% of dendrimer in final solution) | | | | |
|---|---|---|---|---|---|
| Active (percentage, volume) | #1 G1-OH Example 2 | #2 G1-NH2 Example 14 | #3 G1-CO$_2$Na Example 10 | #4 G1-CO$_2$NBu$_4$ Example 12 | #5 G2-OH Example 7 |
| GrowChoice A (1%, 0.05 ml). | 1A (0.05%) | 2A (0.05%) | 3A (0.05%) | 4A (0.05%) | 5A (0.05%) |
| GrowChoice B (1%, 0.05 ml). | 1B (0.1%). | 2B (0.1%). | 3B (0.1%). | 4B (0.1%). | 5B (0.1%). |

TABLE 6-continued

| Active (percentage, volume) | Sample Number (% of dendrimer in final solution) | | | | |
|---|---|---|---|---|---|
| | #1 G1-OH Example 2 | #2 G1-NH2 Example 14 | #3 G1-CO$_2$Na Example 10 | #4 G1-CO$_2$NBu$_4$ Example 12 | #5 G2-OH Example 7 |
| Touchdown C (1%, 0.05 ml). | 1C (0.05%) | 2C (0.05%) | 3C (0.05%) | 4C (0.05%) | 5C (0.05%) |
| Touchdown D (1%, 0.05 ml) | 1D (0.1%). | 2D (0.1%). | 3D (0.1%). | 4D (0.1%). | 5D (0.1%). |
| GrowChoice E (0.5%, 0.025 ml) | 1E,. (0.05%) | 2E (0.05%) | 3E (0.05%) | 4E (0.05%) | 5E (0.05%) |
| Touchdown F (0.5%, 0.025 ml) | 1F (0.05%) | 2F (0.05%) | 3F (0.05%) | 4F (0.05%) | 5F (0.05%) |
| GrowChoice A (1%, 0.05 ml). | GC control | | | | |
| Touchdown C (1%, 0.05 ml). | TD control | | | | |

Biological Assessment: Using Thistle Plants in a Green House

A single 5 μl droplet of each prepared formulation above was applied by micro-syringe onto the adaxial (upper) surface of the third leaf, to the side of the midrib. Assessments of the plants' health were made at 5 days. The trial is on-going for assessment at 14 and 21 day intervals. Table 7 below shows the plants after 5 days (2=Touchdown control, 11=solution 4C).

TABLE 7

| Treatment | Solution | Present leaf stage | Nominal plant diameter.cm | % damage |
|---|---|---|---|---|
| 1 | GrowChoice control | 9 | 22 | 5 |
| 2 | Touchdown control | 8 | 22 | 5 |
| 3 | 1A | 9 | 24 | 10 |
| 4 | 2A | 9 | 26 | 5 |
| 5 | 3A | 9 | 27 | 0 |
| 6 | 4A | 8 | 25 | 0 |
| 7 | 5A | 8 | 27 | 5 |
| 8 | 1C | 9 | 23 | 0 |
| 9 | 2C | 8 | 21 | 5 |
| 10 | 3C | 9 | 24 | 5 |
| 11 | 4C | 8 | 28 | 10 |
| 12 | 5C | 9 | 27 | 5 |

Preliminary indications at 5 days from these results are that solutions 1A and 4C show marginally greater "brown-out" of the centre than the other solutions (scored at 10% vs. 5% for the controls). While not wishing to be bound by theory, it is believed that with the present dendrimer formulation a higher percentage of damage occurs (i.e. the dendrimer is making the active more efficacious) probably by helping draw more of the active into the plant, killing the plant faster or higher activity for lower dose.

Summary of Observed Results:

1. It was virtually impossible to identify the original application site for the two control solutions.
2. There was evidence of necrotic damage at the application site for solutions 5, 6, 7 and 10, 11, 12.
3. The % damage scores above are primarily an assessment of the extent of "brown-out" on the emerging new growth.
4. Treatment groups 3 and 11 which incorporate PEHAM dendrimer show significantly higher percent damage, which is a clear indication that the dendrimer-glyphosate solutions penetrate the leaf surface and provide greater efficacy.

EXAMPLE 21

Improvement in Plant/Seed Penetration and Efficacy of Agriculturally Active Glyphosate when Increasing Concentration of PEHAM Dendrimers The experiment tested whether the addition of dendrimers at various concentrations increased penetration into plant tissue and thus improved the rate of kill utilizing the herbicide glyphosate IPA (GrowChoice® 450 g/L present as the isopropylamine salt). Oats were selected for assessment of glyphosate efficacy because there is less genetic variation. All dosing was carried out at sublethal doses in order to witness a dose effect which is enhanced with dendrimer. A standard dose in the positive control would result in death of the oats and would be presumably replicated in the dendrimer treatments.

Plant Propagation

*Avena sativa* (cv. Echidna) was sown in 10 cm diameter pots filled with potting mix (AS 3743). Enough seeds were planted to ensure a minimum of seven seedlings per treatment group. Seeds were germinated in a temperature-controlled greenhouse (14° C.-25° C.) for 7 days. One week after seedling emergence, seedlings were thinned for uniform size to one seedling per pot and left outdoors for 25 days prior to spray application. This allowed a close simulation to field conditions. Seedlings were treated at 3-4 leaf stage. Herbicide was then applied, see below, and after the application the pots were returned to the greenhouse and kept until assessment.

Spray Mixture Preparation

A 10% v/v sample of Example 2, G1-OH dendrimer was prepared. This dendrimer pre-mix was added to a spray tank before addition of glyphosate. After the addition of glyphosate, spray mixtures were agitated for two min to ensure thorough mixing.

Herbicide Application

The herbicide, glyphosate IPA (GrowChoice® 450 g/L present as the isopropylamine salt), was applied using an enclosed laboratory track-sprayer fitted with three 110° flat fan nozzles (Teejet XR11001-VS) spaced at 50 cm intervals across the boom. The boom moved along a fixed track at 6 km/h, sprayed at a water volume of 64 L/ha with a pressure of 200 kPa. The plants were sprayed with 4 rates of a glyphosate IPA product in a total spray volume of 64 L/ha. A total of 5 concentrations of the Example 2 G1-OH dendrimer (0.01, 0.05, 0.1, 0.2 & 0.5% v/v) were evaluated for enhancement of herbicidal effect at each of the rates of glyphosate tested (35, 70, 140 & 280 g ai/ha).

Assessments

After 10 days the treated plants were assessed for % brownout. After 14 days the plants were harvested by cutting foliage off at the base immediately prior to weighing on a Sartorius Basic electronic balance (range 0-4100 g).

Statistical Analyses

An ARM 7, from Gylling Data Management Inc. statistical package was used to analyze the data with a two way factorial design using dendrimer concentration and glyphosate rate. For the mean of each treatment a 5% least significant difference (LSD) was calculated. The greatest herbicidal effect is denoted with alpha code "a" when significantly different to other treatments, which are coded "b", "c", "d" etc. with decreasing herbicidal effect.

Results

The results of the fresh weight showed no significant difference between the increasing dendrimer concentrations and the control. However, significant differences were observed in the % brownout. The table below shows the results of the % brown out.

TABLE 8

Mean % Brownout for seven replicates per dosing group

| Glyphosate Rate (g ai/ha) | Dendrimer concentration (% v/v) | | | | | | Mean glyphosate rate |
|---|---|---|---|---|---|---|---|
| | 0 | 0.01 | 0.05 | 0.1 | 0.2 | 0.5 | |
| 0 | 0 | | | | | | 0 |
| 35 | 0 j | 0 j | 1.4 ij | 2.9 hij | 6.4 ghi | 5.7 hi | 2.7 d |
| 70 | 5.7 hi | 11.4 f | 7.1 gh | 12.9 f | 13.6 ef | 18.6 de | 11.6 c |
| 140 | 18.6 de | 20.0 cd | 18.6 de | 31.4 b | 24.3 c | 30.0 b | 23.8 b |
| 280 | 37.1 a | 38.3 a | 37.1 a | 38.3 a | 38.6 a | 40.0 a | 38.2 a |
| Mean dendrimer concentration | 15.4 b | 17.4 b | 16.1 b | 21.4 a | 20.7 a | 23.6 a | |

Factorial Analysis of Variance

For the statistical analysis it was determined that there is no significant difference at $P>0.05$, a significant difference at $0.05 \geq P \geq 0.01$, and finally a highly significant difference at $P<0.01$ with a 95% confidence level. The statistical analysis shows there is a highly significant difference between the increasing dendrimer concentrations, a highly significant difference between the increasing glyphosate rate of application and a significant difference between these two factors (dendrimer concentration and glyphosate rate).

TABLE 9

FAOV table - 10DAT

| | FPr | LSD(P = 0.05) |
|---|---|---|
| Dendrimer Concentration | 0.0001 | 2.7 |
| Glyphosate Rate | 0.0001 | 2.1 |
| Dendrimer Concentration × Glyphosate Rate | 0.0192 | 5.2 |

Glyphosate Rate

As expected, as the glyphosate rate is increased, the % brownout is increased on average across all dendrimer concentrations.

Dendrimer Concentration at Different Glyphosate Rates

There was a significant interaction between the two factors. When glyphosate was applied at the upper end of the sublethal doses 280 g ai/ha, no significant difference between any of the dendrimer concentrations was observed.

When glyphosate was applied at 140 g ai/ha, increasing amounts of dendrimer showed significantly higher % brown out compared to the positive control without dendrimer. In particular groups containing 0.5% & 0.1% G1-OH dendrimer were significantly more efficacious. When glyphosate was applied at 70 g ai/ha, once again higher rates of dendrimer (in particular 0.5% and 0.2% G1-OH) provided significantly more % brownout than the positive control. Finally, when glyphosate was applied at 35 g ai/ha, as per the previous examples higher rates of dendrimer (in particular 0.5% and 0.2% G1-OH) were significantly more efficacious than the mid-range dendrimer samples (0.1 and 0.05% G1-OH), while the 0.01% G1-OH and no dendrimer positive control show no brown out or efficacy at all. Thus, within all glyphosate treatment groups, increasing concentrations of dendrimer resulted in significantly increased % brownout. The dendrimer did enhance the rate of brownout of common oat seedlings at concentrations of 0.1% v/v and above when treated with GrowChoice® 450 g/L glyphosate. See FIG. 1. The rate of brownout is a commercially important factor in particular markets.

EXAMPLE 22

Determination of Improved Leaf Penetration of Agrochemicals in the Presence of PEHAM Dendrimers Using the same formulation procedure outline in Example 14 above, a series of 1:1 mixtures of agrochemicals and PEHAM dendrimers were prepared using $^{14}C$ radiolabeled solutions of agrochemicals [$^{14}C$-labelled atrazine 1 mCi/mmol, and glyphosate-mono(isopropyl ammonium) salt 10-30 mCi/mmol]. The oily mixtures were diluted with water to a level of 1% active for application to plants. Control solutions using the same level of agrochemical but no dendrimer were also prepared. Using a microsprayer, uniform droplets of $^{14}C$-labelled herbicide were applied to a circular area (10 mm diameter) adjacent to the mid-rib of the abaxial surface of the fourth leaf of 21-day-old plants of pea plants. Each treatment group was replicated four times. Samples were left for a set uptake period (1-48 h), then the leaves were removed and the abaxial surface washed successively with MeOH+water (1 mL; 1+1 by volume) followed by MeOH (1 mL) delivered from a syringe each over a 20 second duration. The surface washes were combined and the radioactivity determined by scintillation counting using Lumagel (Lumac) as scintillator. Radiolabel retained in the epicuticular wax was subsequently recovered by washing the leaf disc with chloroform (1 mL). The chloroform was removed in a stream of nitrogen, and radioactivity in the wax extracts and surface washes was then determined by liquid scintillation counting (LSC) after addition of 'Hisafe 3' scintillant (4 mL). The relative levels of radioactivity between samples formed a direct comparison of the amount of active that was washed off. Uptake was defined as that proportion of chemical not recovered in the MeOH washes.

Higher levels of active can be determined by HPLC-UV spectroscopy using a Perkin Elmer™ Lambda 2 UV/VIS Spectrophotometer and Waters HPLC. Atrazine content of dendrimer based formulations was compared with the atrazine control (without dendrimer) for comparative leaf penetration.

While not wishing to be bound by theory, it is believed that the present formulation of active entity with dendrimer shows a higher percentage of the active entity is retained on the leaf.

EXAMPLE 23

Soil Adherence/Soil Penetration Assay of an Agriculturally Active Entity in the Presence of PEHAM Dendrimers As an initial trial, test columns (approximately 8 cm diameter, 10 cm length) of fine sand containing 10% moisture were treated with 10 mL of aqueous active and 1 mL of 5% dendrimer. Control columns containing no dendrimer were also prepared.

The columns were subjected to 1 day of leaching with the solutions containing the active. After this time each column was treated with an additional 10 mL of water to promote movement of active in the soil column. After the three days the columns were split into three horizontal sections and each section is assayed by HPLC or GC for active content so that a vertical profile can be constructed for the soil column. Comparison of the levels of active entity in the water eluent verses the amounts retained in the soil provide an assessment of the relative level of soil adherence versus penetration with and without PEHAM dendrimer.

While not wishing to be bound by theory, it is believed that the present formulations with dendrimer and active entity will increase soil penetration such that the active entity will reach the plant roots or under soil parts of plants.

EXAMPLE 24

Soil Adherence/Soil Penetration Assay of Agriculturally Active Entity in Presence of PEHAM Dendrimers Part A This experiment investigated whether the inclusion of dendrimers influences the soil migration of trifluralin solutions. Trifluralin is extremely resistant to leaching in soil. This trial is based on a technique developed over some years to quantify the leaching of actives in a soil column, in this case sand, using trifluralin combined with a selected dendrimer.

Method

A standard sand soil test rig was constructed. The soil column was contained in a PVC tube which is 8.5 cm in diameter by 7.5 cm high, constructed in a way so that it can be separated into three 2.5 cm. vertical sections. The tube was tightly packed with sand which was adjusted to contain 7.2-7.7% moisture immediately prior to preparation of soil column. Two trials were conducted, both using the trifluralin dendrimer formulation shown in Example 14 above (G1-$NH_2$ 5.43 g/L trifluralin at pH 7). The first trial used 20 mL of the trifluralin and the second used 50 mL. In both cases no supplementary leaching was applied. After the addition of the sample, the columns were left to stand for three days. The column was demounted into the 3 sections and each section was left to dry. The three sections of the column were designated as section 1, section 2 and section 3 numbering from top to bottom section. As trifluralin is a highly colored compound, appearance of the column Sections were visually assessed for color and thus amount of trifluralin.

The dried section of soil was weighed. Each section was extracted in a Soxhlet apparatus for 1.5 h using 50 mL of acetone. The acetone extract was taken and the solvent reduced using a rotary evaporator to approximately 20 mL. The remaining extract was transferred to a volumetric flask and made up to exactly 25 mL using acetone, and the sample was analyzed for trifluralin content by GC using the AOAC-CIPAC method 1975, Trifluralin Technical183/TC/M/. The concentration of trifluralin appears to be increasing with depth in both trials, see Table 10 below.

TABLE 10

Distribution of trifluralin through soil column

| 20 mL | | 50 mL | |
|---|---|---|---|
| Section | Appearance | Section | Appearance |
| 1. Top | L. Yellow | 1. Top | L. Yellow |
| 2. Middle | Darker | 2. Middle | Darker |
| 3. Lower | Darkest | 3. Lower | Darkest |

It is well known that trifluralin is extremely resistant to leaching in soil. These results indicate that the dendrimer significantly assists in leaching trifluralin through a sand column.

Part B

This test investigated whether the inclusion of dendrimers influences the soil migration of Imidacloprid solutions. This trial is based on a technique developed over some years to quantify the leaching of actives in a soil column, in this case sand, using Imidacloprid combined with each of four selected dendrimers.

Method

The standard procedure of Part A was altered to make the influence of dendrimer more obvious by the addition of further leaching water during the test. Soil columns were prepared as outlined above. A 500 ppm saturated aqueous solution of Imidacloprid was added to the top of a soil column and the column was then immediately flushed with 1 mL of a 5% aqueous solution of the respective dendrimer solution.

After 1 day 10 mL of water was added to all the columns; the columns were then left to dry for three days. After this time the columns were dismounted into sections, dried in an ambient air stream and the weight of each section recorded. Each section was extracted in a Soxhlet apparatus for 1.5 h with 50 mL of acetone. The acetone extract was taken and the solvent reduced using a rotary evaporator to approximately 20 mL. The remaining extract was transferred to a volumetric flask and made up to exactly 25 mL using acetone. The sample analyzed for Imidacloprid content by HPLC using the standard method by CIPAC 2001 Imidacloprid Technical 582/TC/M2/-.

TABLE 11

| Sample | Weight of dry sand (g) | Amount of active (mg) | Amount of active per weight of sand (mg/g × 100) | Total amount of active in column (mg) |
|---|---|---|---|---|
| Control - Top | 218.2 | 2.5 | 1.15 | |
| Control - Middle | 230.7 | 2.2 | 0.95 | |

TABLE 11-continued

| Sample | Weight of dry sand (g) | Amount of active (mg) | Amount of active per weight of sand (mg/g × 100) | Total amount of active in column (mg) |
|---|---|---|---|---|
| Control - Lower | 218.9 | 0.4 | 0.18 | 5.1 |
| G1-OH Example 2 Top | 215.7 | 1.4 | 0.65 | |
| G1-OH Example 2 Middle | 232.4 | 1.7 | 0.73 | |
| G1-OH Example 2 Lower | 211.8 | 1.9 | 0.90 | 5.0 |
| G1-$NH_2$ Example 14 Top | 214.8 | 1.2 | 0.56 | |
| G1-$NH_2$ Example 14 Middle | 228.1 | 1.7 | 0.75 | |
| G1-$NH_2$ Example 14 Lower | 206.7 | 1.8 | 0.87 | 4.7 |
| G1-COONa Example 10 Top | 210.8 | 2.3 | 1.09 | |
| G1-COONa Example 10 Middle | 224.6 | 1.2 | 0.53 | |
| G1-COONa Example 10 Lower | 190.5 | 1.15 | 0.60 | 4.65 |
| G1-COON$Bu_4$ Example 12 Top | 195.4 | 1.9 | 0.97 | |
| G1-COON$Bu_4$ Example 12 Middle | 232.7 | 0.9 | 0.39 | |
| G1-COON$Bu_4$ Example 12 Lower | 223.4 | 1.85 | 0.83 | 4.65 |

All columns treated with dendrimer showed a vertical gradation of active not apparent in the control. See FIG. 2. Addition of dendrimer to the solutions, as noted above, increased the aqueous solubility. This effect obviously assists in moving the active through a soil column. Examples 2 and 14 show a more pronounced effect. By utilizing dendrimer formulations the mobility of active through soil has been significantly altered.

EXAMPLE 25

Dendrimer-Copper Complex Formation and Enhanced Leaf Retention/Water Fastness

A stock 1% copper sulfate solution was prepared by dissolving 10 g of copper sulphate in 1 L of water. A series of four solutions were prepared by adding either 0 mg (0.0% w/v), 25 mg (0.1% w/v), 50 mg (1.0% w/v) or 500 mg (10.0% w/v) of PEHAM dendrimer to 5 mL of the stock copper sulfate solution prepared above. These complexes were briefly exposed to ultrasonication, then incubated overnight at 37° C. and 100 rpm in a shaking water bath, and allowed to equilibrate at RT for 1 h. The dendrimer-copper sulfate active suspensions were filtered through a Whatman filter to remove any solid content. The samples were analyzed for copper using standard processes.

The various PEHAM dendrimer-copper sulfate formulations, prepared above, were applied to plant leaves (3-5 weeks old) and incubated for 24 h in a greenhouse. After 24 h, leaves were gently washed with 10 mL of water while collecting all the wash water. The combined wash water was analyzed for copper content by UV spectroscopy using a Perkin Elmer™ Lambda 2 UV/VIS Spectrophotometer. Alternatively low levels of copper can be detected by inductively coupled plasma atomic emission spectroscopy. Copper content of dendrimer based formulations was compared with control (copper alone).

While not wishing to be bound by theory, use of copper with dendrimer in the present formulations has less of the copper washed off the leaf and so a higher percentage of the active copper is retained on the leaf. The copper is used as a fungicide on grapes. Thus, less application (amount and frequency) of the copper is desired for the environment while still providing protection as a fungicide for the grapes.

EXAMPLE 26

Determining the Solubility of a Range of Agricultural Chemical, Active Constituents in Water Containing Selected PEHAM Dendrimers Four PEHAM dendrimers, each at 10 g/L and 100 g/L in water, were used for evaluation. A 15 g of each dendrimer was dissolved in distilled water and made accurately to 150 mL volume. Determination of pH was then made using a calibrated pH meter and electrode.

Preparation of Saturated Active Constituent Solutions

To prepare saturated solutions of active constituent in 100 g/L dendrimer solutions, 10 mL of each 100 g/L dendrimer solution was placed into a 50 mL test tube and 0.2 g of active constituent was then also added. The test tube was then briefly shaken to disperse the contents, before being placed in an ultrasonic water bath, and subjected to sonication for 30 mins at 500° C. The test tube and contents were then cooled to 200° C. and then a 2.0 mL aliquot was taken and filtered through a 0.45 µm PTFE membrane filter.

To prepare saturated solutions of active constituent in 10 g/L dendrimer solutions, 1.0 mL of each 100 g/L dendrimer solution was placed into a 50 mL test tube and a 9.0 mL aliquot of distilled water added and 0.2 g of active constituent was then also added. The test tube was then briefly shaken to disperse the contents, before being placed in an ultrasonic water bath, and subjected to sonication for 30 mins at 500° C. The test tube and contents were then cooled to 200° C. and then a 2.0 mL aliquot was taken and filtered through a 0.45 µm PTFE membrane filter For each active constituent, 10 dendrimer solutions at 100 g/L and 10 dendrimer solutions at 10 g/L resulted in 20 solutions. Each prepared and filtered solution was examined in a light box for Tyndall Scattering (light scattering by particles in a colloid or particles in a fine suspension). A visual observation was made and recorded for each solution. Ten active constituents that were selected to cover a range of water solubility were treated according to the method described here. A total of 200 filtered solutions were prepared.

HPLC Analysis of Saturated Active Constituent in Dendrimer Solutions

High Performance Liquid Chromatography was used to analyse each active constituent in each dendrimer solution. Each saturated active constituent solution was freshly prepared for immediate analysis or frozen at <−15° C. where analysis could not take place within 2 hours of preparation. The following are details of the HPLC equipment used. For each active constituent a set of 4 calibration solutions was prepared 0 to 25 ppm. A sequence of injections comparing the peak area of the calibration solutions and the dendrimer solutions was then undertaken. The dendrimer solutions were diluted as required to maintain their respective peak area response within the calibration range. The active constituent concentration (ppm) in the dendrimer solution was determined by calculation: RF×SA×DF, where RF=Response Factor (concentration of calibration solution per unit of peak area, SA=Sample Peak Area (peak area of the sample solution), and DF=Dilution Factor (dilution of the sample solution). HPLC conditions were varied to ensure the optimum detection and separation of each active constituent from excipients.

TABLE 12a

Ratio of Active Ingredient in Dendrimer Solution (ppm) to Active Ingredient in Water (ppm) for 10 g/L loading

| 10 g/L loading | Bifen-thrin | Pendime-thalin | Propa-quizafop | Thidia-zuron | 6-BAP | Penco-nazole | Mcylo-butanil | Cloma-zone | Thia-methoxam | Flumet-sulam |
|---|---|---|---|---|---|---|---|---|---|---|
| Water | 1 | 1 | 1 | 1 | 1 | 1 | 1 | 1 | 1 | 1 |
| G1-TMPTGE-NH$_2$ | 1 | 172 | 1 | 46 | 10 | 2 | 3 | 1 | 2 | 2 |
| G1-TMPTGE-COONa | 1 | 11 | 1 | 19 | 7 | 2 | 2 | 1 | 2 | 2 |
| G1-TMPTGE-OMe | 9 | 44 | 1 | 5 | 3 | 2 | 2 | 1 | 2 | 1 |
| G1-TMPTGE-OH | 1 | 1 | 1 | 7 | 4 | 2 | 2 | 1 | 2 | 2 |

TABLE 12b

Ratio of Active Ingredient in Dendrimer Solution (ppm) to Active Ingredient in Water (ppm) for 100 g/L loading

| 100 g/L loading | Bifen-thrin | Pendime-thalin | Propa-quizafop | Thidia-zuron | 6-BAP | Penco-nazole | Mcylo-butanil | Cloma-zone | Thia-methoxam | Flumet-sulam |
|---|---|---|---|---|---|---|---|---|---|---|
| Water | 1 | 1 | 1 | 1 | 1 | 1 | 1 | 1 | 1 | 1 |
| G1-TMPTGE-$NH_2$ | 4 | 15 | 1 | 329 | 2740 | 6 | 4 | 1 | 1 | 2 |
| G1-TMPTGE-COONa | 1 | 2 | 1 | 40 | 448 | 3 | 2 | 1 | 1 | 2 |
| G1-TMPTGE-OMe | 1 | 41 | 1 | 17 | 475 | 12 | 3 | 1 | 2 | 2 |
| G1-TMPTGE-OH | 1 | 6 | 1 | 39 | 967 | 43 | 4 | 1 | 2 | 4 |

As used herein, the term "about" refers to plus or minus 10% of the referenced number.

Although the invention has been described with reference to its preferred embodiments, those of ordinary skill in the art may, upon reading and understanding this disclosure, appreciate changes and modifications which may be made which do not depart from the scope and spirit of the invention as described above or claimed hereafter. Various modifications of the invention, in addition to those described herein, will be apparent to those skilled in the art from the foregoing description. Such modifications are also intended to fall within the scope of the appended claims. Each reference cited in the present application is incorporated herein by reference in its entirety.

Although there has been shown and described the preferred embodiment of the present invention, it will be readily apparent to those skilled in the art that modifications may be made thereto which do not exceed the scope of the appended claims. Therefore, the scope of the invention is only to be limited by the following claims. Reference numbers recited in the claims are exemplary and for ease of review by the patent office only, and are not limiting in any way. In some embodiments, the figures presented in this patent application are drawn to scale, including the angles, ratios of dimensions, etc. In some embodiments, the figures are representative only and the claims are not limited by the dimensions of the figures. In some embodiments, descriptions of the inventions described herein using the phrase "comprising" includes embodiments that could be described as "consisting of", and as such the written description requirement for claiming one or more embodiments of the present invention using the phrase "consisting of" is met.

What is claimed is:

1. A formulation comprising:
   0.1% v/v or more of a glyphosate isopropylamine (IPA) salt; and
   a PEHAM dendrimer of the formula:

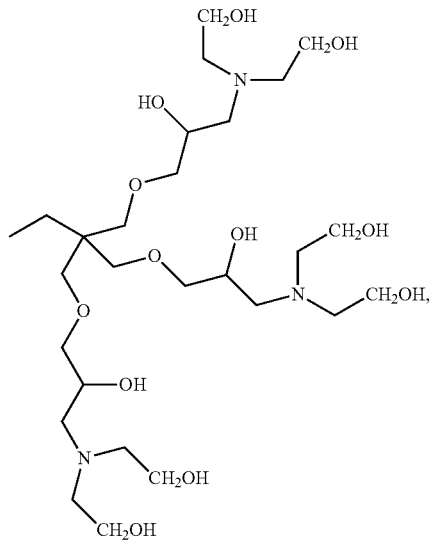 [SMILES: CCC(COCC(O)CN(CCO)CCO)(COCC(O)CN(CCO)CCO)COCC(O)CN(CCO)CCO]

wherein the PEHAM dendrimer is associated with the glyphosate isopropylamine (IPA) salt.

2. The formulation of claim 1, wherein the formulation is in the form of an agriculturally-acceptable liquid, or concentrate.

3. The formulation of claim 1, further comprising an agriculturally-acceptable diluent or carrier.

4. The formulation of claim 1, wherein the formulation is in the form of an agriculturally-acceptable powder, dust or granule.

5. The formulation of claim 1, wherein the formulation is in the form of an agriculturally-acceptable suspension, emulsion, spray, gel, or aerosol.

* * * * *